United States Patent [19]
Ono et al.

[11] Patent Number: 5,658,904
[45] Date of Patent: Aug. 19, 1997

[54] 1,2-ETHANEDIOL DERIVATIVE AND SALT THEREOF AND CEREBRAL FUNCTION-IMPROVING AGENT COMPRISING THE SAME

[75] Inventors: Satoshi Ono, Toyama; Tetsuo Yamafuji; Hisaaki Chaki, both of Toyama-ken; Mutsuko Maekawa, Toyama; Yozo Todo, Toyama; Hirokazu Narita, Toyama, all of Japan

[73] Assignee: Toyama Chemical Co., Ltd., Tokyo, Japan

[21] Appl. No.: 466,830

[22] Filed: Jun. 6, 1995

Related U.S. Application Data

[62] Division of Ser. No. 174,793, Dec. 29, 1993, Pat. No. 5,472,984, which is a division of Ser. No. 940,747, Sep. 8, 1992, Pat. No. 5,280,032, which is a continuation of Ser. No. 566,889, Aug. 14, 1990, abandoned, which is a continuation-in-part of Ser. No. 480,114, Feb. 14, 1990, abandoned.

[30] Foreign Application Priority Data

| Feb. 14, 1989 | [JP] | Japan | 1-032714 |
| Mar. 20, 1989 | [JP] | Japan | 1-068958 |
| Apr. 26, 1989 | [JP] | Japan | 1-106187 |
| Feb. 5, 1990 | [JP] | Japan | 2-24501 |
| Feb. 5, 1990 | [JP] | Japan | 2-24502 |
| Feb. 5, 1990 | [JP] | Japan | 2-24503 |

[51] Int. Cl.$^6$ .................... A61K 31/34; C07D 307/81
[52] U.S. Cl. .................... 514/237.2; 548/179; 548/205; 548/304.4; 548/340.1; 548/486; 548/490; 548/503; 549/75; 549/362; 549/443; 549/467; 549/491; 514/249; 514/253; 514/311; 514/312; 514/351; 514/352; 514/357; 514/367; 514/394; 514/415; 514/418; 514/438; 514/452; 514/463; 514/469; 514/471; 544/124; 544/353; 544/376; 546/158; 546/166; 546/176; 546/300; 546/312; 546/334
[58] Field of Search .................... 549/467, 75, 362, 549/443, 491; 514/469, 237.2, 249, 253, 311, 312, 351, 352, 357, 367, 394, 415, 418, 438, 492, 463; 544/124, 353, 376; 546/158, 166, 176, 300, 312, 334; 548/179, 205, 304.4, 340.1, 486, 490, 503

[56] References Cited

U.S. PATENT DOCUMENTS 4,237,138  12/1980  Campbell et al. ............ 514/260

FOREIGN PATENT DOCUMENTS 30 03 323   8/1980   Germany .

OTHER PUBLICATIONS

Journal of Medicinal Chemistry, vol. 31, No. 3, *Mar. 1988*, pp. 516–520, Simon F. Campbell, et al., "2,4–Diamino–6, 7–Dimethoxyquinazolines. 4. 2–[4–(Substituted Oxyethoxy)Piperidino] Derivatives as Alpha1–Adrenoceptor Antagonists and Antihypertensive Agents".

Carcinogenesis, vol. 9, No. 9, 1988, pp. 1657–1660, Pavel Vodicka, et al., "Identification of Alkylation Products of Styrene Oxide in Single– and Double–Stranded DMa".

The Journal of Organic Chemistry, vol. 51, No. 15, *Jul. 15, 1986*, pp. 2952–2955, Robert C. Moschel, et al., "Hydrolysis and Rearrangementof O6–Substituted Guanosine Products Resulting From Reaction of Guannosine with Styrene Oxide".

Archiv der Pharmazie, vol. 296, No. 1, 1963, pp. 38–47, K. Winterfeld, et al., "Zur Kenntnis Phenyl–Substituierter Oxa–Chinolizidine".

The Journal of Organic Chemistry, vol. 50, No. 20, Oct. 4, 1985, pp. 3942–3943, William R. Baker, "Metalation of 4,5–Diphenyl–2–[2–(Trimethylstannyl)ethyl]oxazole with Titanium Tetra–Chloride. A New Carbon–Carbon Bond Forming Methodology Based on Organotitanium Reagents".

Rencl. Accad. Mat. 40 (Quaranta) [4], 1968, pp. 269–280, Leandro Baiocchi, et al., "Su Alcune Trasposizioni Nella Serie Dell'Indazolo".

*Primary Examiner*—Richard L. Raymond
*Attorney, Agent, or Firm*—Oblon, Spivak, McClelland, Maier & Neustadt, P.C.

[57] ABSTRACT

This invention relates to a 1,2-ethanediol derivative and a salt thereof, a process for producing the same, and a cerebral function-improving agent comprising the same. The cerebral function-improving agent of this invention is useful for treating cerebrovascular dementia, senile dementia, Alzheimer's dementia, sequelae of ischemic encephalopathy and cerebral apoplexy.

10 Claims, No Drawings

1,2-ETHANEDIOL DERIVATIVE AND SALT THEREOF AND CEREBRAL FUNCTION-IMPROVING AGENT COMPRISING THE SAME

This is a Division of application Ser. No. 08/174,793 filed on Dec. 29, 1993 now U.S. Pat. No. 5,472,484, which is a Divisional of Ser. No. 07/940,747 filed on Sep. 8, 1992 now U.S. Pat. No. 5,280,032, which is a Continuation of Ser. No. 07/566,889 filed on Aug. 14, 1990 now abandoned, which is a Continuation-in-Part of Ser. No. 07/480,114 filed on Feb. 14, 1990 now abandoned.

This invention relates to a 1,2-ethanediol derivative and a salt thereof, a process for producing the same, and a cerebral function-improving agent comprising the same. The cerebral function-improving agent of this invention is useful for treating cerebrovascular dementia, senile dementia, Alzheimer's dementia, sequelae of ischemic encephalopathy and cerebral apoplexy.

As 1,2-ethanediol derivatives, there are known, for example, those described in U.S. Pat. No. 2,928,845; J. Pharm. Sci., vol. 50, pp. 769–771 (1961); Farmaco. Ed. Sci., vol. 19, pp. 1056–1065 (1964); etc.

These compounds are in use as a local anesthetic. However, nothing is known as to their use as a cerebral function-improving agent, an antiamnesic agent or a nootropic agent.

WO No. 88/8424 describes that 1,2-ethanediol derivatives can be used for the remedy of Alzheimer's disease and other degenerative neurological disorders. However, no specific description or example of these derivatives is given in the application.

Drugs such as cerebral metabolic enhancers, cerebrovasodilators and the like are currently in use for the remedy of various dementias, particularly dementia of Alzheimer's type and cerebrovascular dementia.

However, no cerebral function-improving agent has been found as yet which is useful for treating cerebrovascular dementia, senile dementia, Alzheimer's dementia, sequelae of ischemic encephalopathy and cerebral apoplexy.

An object of this invention is to provide a novel 1,2-ethanediol derivative and a salt thereof.

Another object of this invention is to provide a process for producing a novel 1,2-ethanediol derivative and a salt thereof.

Still another object of this invention is to provide a novel cerebral function-improving agent which is useful for treating cerebrovascular dementia, senile dementia, Alzheimer's dementia, sequelae of ischemic encephalopathy and cerebral apoplexy and yet has little side effect.

The present inventors have made study in order to solve the above-mentioned problems. As a result, it has been found that a 1,2-ethanediol derivative represented by the following general formula [I] or a salt thereof has an excellent antiamnesic activity and an excellent antihypoxic activity and is very useful as a cerebral function-improving agent:

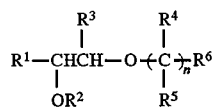

[I]

wherein $R^1$ represents a substituted or unsubstituted phenyl, naphthyl, indanyl, indenyl, tetrahydronaphthyl or heterocyclic group; $R^2$ represents a hydrogen atom, a lower alkyl group or a hydroxyl-protecting group; $R^3$ represents a hydrogen atom or a lower alkyl group; $nR^4$'s and $nR^5$'s are the same as or different from one another and represent hydrogen atoms or lower alkyl groups; $R^6$ represents an ammonio group or a substituted or unsubstituted amino or nitrogen-containing heterocyclic group, the nitrogen-containing heterocyclic group being selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl groups; and n represents 0 or an integer of 1 to 6; wherein the substituent on $R^1$ is selected from the group consisting of halogen atoms, substituted or unsubstituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino and heterocyclic groups and protected amino groups, protected or unprotected hydroxyl groups, nitro group, oxo group and lower alkylenedioxy groups; the substituted lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino or heterocyclic group as the substituent of $R^1$ and the substituted nitrogen-containing heterocyclic group as $R^6$ have each at least one substituent selected from the group consisting of halogen atoms, protected or unprotected hydroxyl groups, protected or unprotected amino groups, protected or unprotected carboxyl groups, unsubstituted lower alkyl groups, lower alkyl groups substituted by a protected or unprotected hydroxyl group, unsubstituted or halogen-substituted aryl groups, unsubstituted or halogen-substituted aroyl groups, unsubstituted lower alkoxy groups, lower alkoxy groups substituted by a lower alkoxy group, lower acyl groups, ar-lower alkyl groups, ar-lower alkenyl groups, heterocyclic groups, heterocyclic-CO— groups, oxo group, lower alkylsulfonyl groups and arylsulfonyl groups; and the substituted amino group as the substituent of $R^1$ and the substituted amino group as $R^6$ have each at least one substituent selected from the group consisting of protected or unprotected hydroxyl groups, unsubstituted lower alkyl groups, lower alkyl groups substituted by a protected or unprotected carboxyl or hydroxyl group, cycloalkyl groups, aryl groups, lower acyl groups, ar-lower alkyl groups, heterocyclic groups, unsubstituted or oxo-substituted heterocyclic-CO— groups, adamantyl group, lower alkylsulfonyl groups and arylsulfonyl groups, provided that there are excluded the compounds in which $R^1$ is a phenyl group which may optionally be substituted by the halogen atom or the lower alkyl, lower alkylenedioxy, lower alkoxy or protected or unprotected hydroxyl group and $R^6$ is —$NR^7R^8$ in which $R^7$ represents an ar-lower alkyl or heterocyclic group and $R^8$ represents a hydrogen atom or a lower alkyl group, or $R^7$ and $R^8$ form, when taken with the N atom,

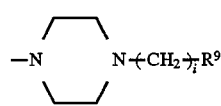

in which $R^9$ represents an aryl or heterocyclic group and i represents 0 or an integer of 1 to 3,

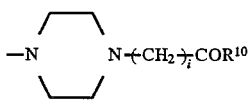

in which $R^{10}$ represents an aryl, heterocyclic or

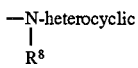

group and $R^8$ and i have the same meanings as defined above,

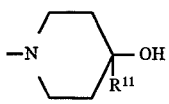

in which $R^{11}$ represents an aryl group,

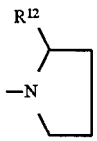

in which $R^{12}$ represents a carboxyl group or a lower alkoxycarbonyl group or

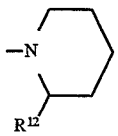

in which $R^{12}$ has the same meaning as defined above and the compounds in which $R^1$ represents an unsubstituted or lower alkyl-substituted phenyl group and $R^6$ represents a di-lower alkylamino group,

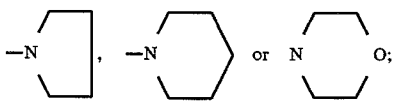

all the above heterocyclic groups being selected from the group consisting of the nitrogen-containing heterocyclic groups mentioned in the definition of $R^6$ and furyl, thienyl, benzothienyl, pyranyl, isobenzofuranyl, oxazolyl, benzofuranyl, indolyl, benzimidazolyl, benzoxazolyl, benzothiazolyl, quinoxalyl, dihydroquinoxalyl, 2,3-dihydrobenzothienyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl and isoquinolyl groups.

Incidentally, the cerebral function-improving agent mentioned herein refers to a cerebral-function-improving agent having not only effects possessed by conventional cerebral-function-improving agents, for example, sequelae of ischemic encephalopathy and cerebral apoplexy but also therapeutic or prophylactic effects for amnesia and dementias (e.g. cerebrovascular dementia, senile dementia and Alzheimer's dementia).

In the present specification, the following terms have the following definitions unless otherwise specified.

The term "halogen atom" means, for example, a fluorine atom, a chlorine atom, a bromine atom and an iodine atom; the term "lower alkyl group" means $C_{1-6}$ alkyl groups such as methyl, ethyl, n-propyl, isopropyl, n-butyl, isobutyl, tert-butyl, pentyl, hexyl and the like; the term "lower alkoxy group" means $C_{1-6}$ alkyl-O— groups; the term "lower alkylthio group" means $C_{1-6}$ alkyl-S— groups; the term "lower alkenyl group" means $C_{2-6}$ alkenyl groups such as vinyl, propenyl, butenyl, pentenyl, hexenyl and the like; the term "lower alkenyloxy group" means $C_{2-6}$ alkenyl-O— groups; the term "cycloalkyl group" means $C_{3-6}$ cycloalkyl groups such as cyclopropyl, cyclobutyl, cyclopentyl, cyclohexyl and the like; the term "aryl group" means phenyl, naphthyl, indanyl and indenyl groups; the term "aryloxy group" means aryl-O-groups; the term "ar-lower alkyl group" means ar-$C_{1-4}$ alkyl groups such as benzyl, diphenylmethyl, trityl, phenethyl and the like; the term "ar-lower alkoxy group" means ar-$C_{1-4}$alkyl-O— groups; the term "ar-lower alkylthio group" means aryl-$C_{1-4}$alkyl-S— groups; the term "lower alkylenedioxy group" means $C_{1-4}$alkylenedioxy groups such as methylenedioxy, ethylenedioxy and the like; the term "lower acyl group" means $C_{1-6}$acyl groups such as formyl, acetyl, butyryl and the like; the term "aroyl group" means aryl-CO— groups; the term "lower alkylsulfonyl group" means $C_{1-6}$alkyl-SO$_2$— groups; the term "arylsulfonyl group" means aryl-SO$_2$— groups; the term "ar-lower alkylsulfonyl group" means aryl-$C_{1-6}$alkyl-SO$_2$— groups; the term "lower alkylsulfonyloxy group" means $C_{1-6}$alkyl-SO$_2$-O— groups; the term "arylsulfonyloxy group" means aryl-SO$_2$-O— groups; the term "lower alkylsulfonylamino group" means $C_{1-6}$alkyl-SO$_2$—NH— groups; the term "arylsulfonylamino group" means aryl-SO$_2$NH— groups; the term "di-lower alkylamino group" means di-$C_{1-6}$alkyl-NH— groups and the term "ammonio group" means tri-lower alkylammonio groups such as trimethylammonio, triethylammonio; the term "lower alkoxycarbonyl group" means $C_{1-6}$alkyl-O—CO— groups and the like.

The protective groups for hydroxyl group, carboxyl group and amino group include those conventional protective groups for hydroxyl group, carboxyl group and amino group which are described in Protective Groups in Organic Synthesis [Theodra W. Green (1981), John Wiley & Sons, Inc.]. In particular, the protective group for hydroxyl group specifically includes, for example, lower alkyl, lower acyl, tetrahydropyranyl and ar-lower alkyl groups such as substituted or unsubstituted benzyl.

The salt of the 1,2-ethanediol derivative represented by the general formula [I] can be any pharmaceutically acceptable salt. It includes, for example, salts with mineral acids such as hydrochloric acid, hydrobromic acid, sulfuric acid, phosphoric acid and the like; salts with carboxylic acids such as formic acid, acetic acid, oxalic acid, fumaric acid, maleic acid, malic acid, tartaric acid, aspartic acid and the like; salts with sulfonic acids such as methanesulfonic acid, benzenesulfonic acid, p-toluenesulfonic acid, naphthalenesulfonic acid and the like; and salts with alkali metals such as sodium, potassium and the like.

When the 1,2-ethanediol derivative of the general formula [I] or its salt has isomers (e.g. optical isomers, geometrical isomers, tautomers), all of these isomers are included in this invention. Also, the hydrate, solvate and all crystal forms of the compound of this invention are included in this invention.

Next, there is described a process for producing a 1,2-ethanediol derivative of the general formula [I] or a salt thereof.

The 1,2-ethanediol derivative of the general formula [I] or its salt can be produced by per se known processes or their appropriate combinations, for example, the following production processes.

Production Process 1
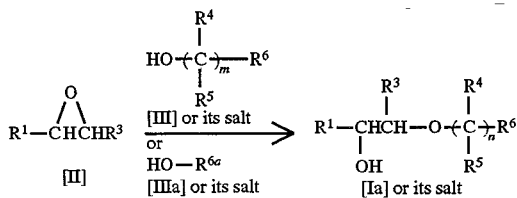
Production Process 2
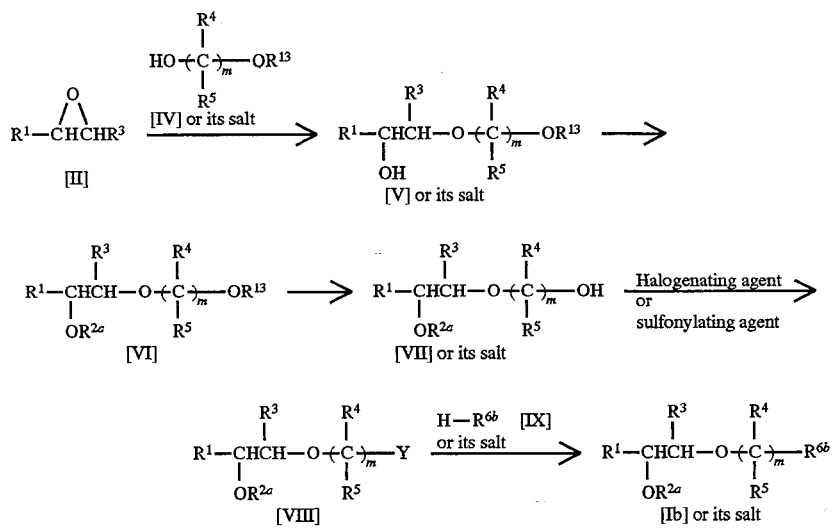
Production Process 3
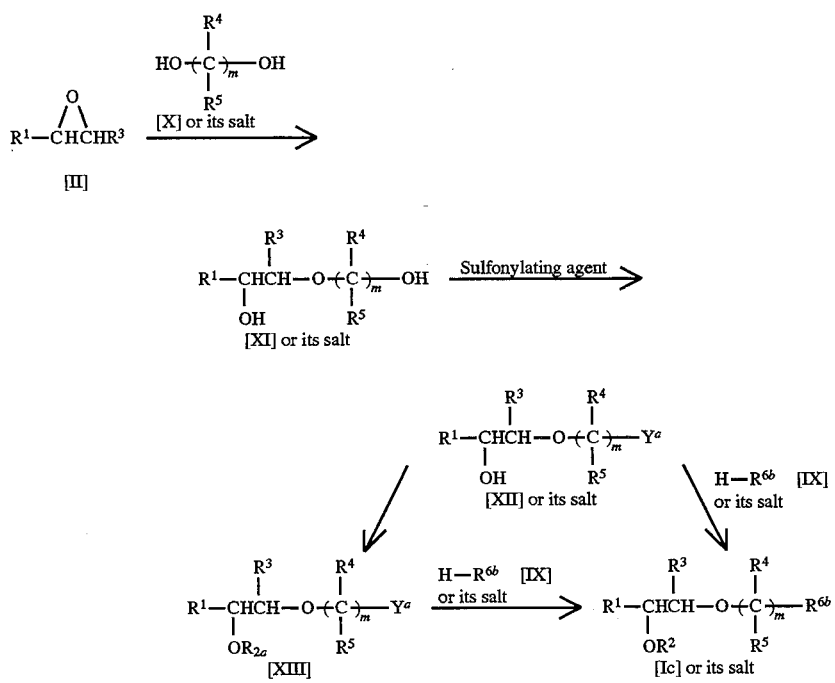

Production Process 4

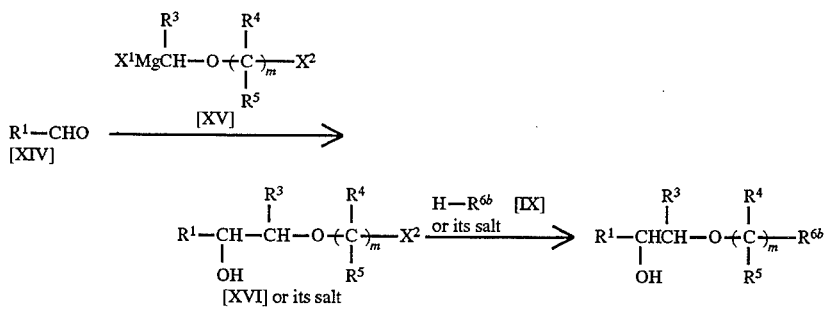

[XVI] or its salt

In the above reaction schemes, $R^1$, $R^2$, $R^3$, $R^4$, $R^5$, $R^6$ and n have the same meanings as defined above; $R^{2a}$ represents the same hydroxyl-protecting group as in the definition of $R^2$; $R^{6a}$ represents the same substituted or unsubstituted nitrogen-containing heterocyclic group as in the definition of $R^6$, provided that the heterocyclic group has a free valence on a carbon atom forming the heterocyclic ring; $R^{6b}$ represents the same substituted or unsubstituted nitrogen-containing heterocyclic group as in the definition of $R^6$, provided that the nitrogen-containing heterocyclic group has a free valence on a nitrogen atom forming the heterocyclic ring, or a substituted or unsubstituted amino group; $R^{13}$ represents the same hydroxyl-protecting group as in the definition of $R^2$; $X^1$ and $X^2$, which may be the same or different, represent halogen atoms, Y represents a removable group such as a halogen atom, a lower alkylsulfonyloxy group, an arylsulfonyloxy group or the like; $Y^a$ represents an arylsulfonyloxy group; and m represents an integer of 1–6.

As the salts of the compounds of the general formulas [III], [IIIa], [IV], [V], [VII], [IX], [X], [XI], [XII], [XVI], [Ia], [Ib], [Ic] and [Id], there can be mentioned the same salts as the salts of the compound of the general formula [I].

Next, each of the above production processes is described.

Production Process 1

A compound of the general formula [II] is reacted with a compound of the general formula [III] or its salt or a compound of the general formula [IIIa] or its salt in the presence or absence of a base to obtain a compound of the general formula [Ia] or its salt.

The solvent to be used in this reaction can be any solvent unless it adversely affects the reaction. There can be mentioned, for example, aromatic hydrocarbons such as benzene, toluene, xylene and the like; sulfoxides such as dimethylsulfoxide and the like; amides such as N,N-dimethylformamide and the like; and ethers such as tetrahydrofuran, dioxane and the like. These solvents can be used alone or in admixture of two or more. It is also possible to use the compound of the general formula [III] or [IIIa] as the solvent.

As the base to be used optionally, there can be mentioned, for example, sodium hydride, metallic sodium and potassium tert-butoxide.

In the reaction, the compound of the general formula [III] or its salt, or the compound of the general formula [IIIa] or its salt is used in an amount of 1–100 moles, preferably 1–10 moles, per mole of the compound of the general formula [II].

The base as an optional component is used in an amount of 0.01–1.2 moles per mole of the compound of the general formula [II].

This reaction can be effected usually at 20°–150° C., preferably 70°–90° C., for 1 minutes to 24 hours, preferably 5 minutes to 5 hours.

Production Process 2

(1) A compound of the general formula [II] is reacted with a compound of the general formula [IV] or its salt in the presence or absence of a base to obtain a compound of the general formula [V] or its salt.

This reaction can be effected in the same manner as described in Production Process 1.

The obtained compound of the general formula [V] or its salt may be used in the subsequent reaction without being isolated.

(2) The compound of the general formula [V] or its salt is subjected to conventional reaction for protection of hydroxyl group to obtain a compound of the general formula [VI].

The obtained compound of the general formula [VI] may be used in the subsequent reaction without being isolated.

Then, the compound of the general formula [VI] is subjected to reaction for selective removal of the hydroxyl-protecting group to obtain a compound of the general formula [VII] or its salt.

The obtained compound of the general formula [VII] or its salt may be used in the subsequent reaction without being isolated.

These reactions can be effected according to per se known methods, for example, the method described in Protective Groups in Organic Synthesis [Theodra W. Green (1981), John Wiley & Sons, Inc.] or a method similar thereto.

The combination of the hydroxyl-protecting groups ($R^{13}$ and $R^{2a}$) to be used in these reactions can be selected appropriately.

(3) The compound of the general formula [VII] or its salt is reacted with a halogenating agent or a sulfonylating agent in a solvent in the presence or absence of a base to obtain a compound of the general formula [VIII].

The solvent to be used in the reaction can be any solvent unless it adversely affects the reaction. There can be mentioned, for example, halogenated hydrocarbons such as methylene chloride, chloroform and the like; ethers such as tetrahydrofuran, dioxane and the like; nitriles such as acetonitrile and the like; and amides such as N,N-dimethylformamide and the like. These solvents can be used alone or in admixture of two or more.

As the base to be used optionally, there can be mentioned, for example, organic and inorganic bases such as triethylamine, diisopropylethylamine, 1,8-diazabicyclo-[5.4.0]undec-7-ene (DBU), pyridine, potassium tert-butoxide, sodium carbonate, potassium carbonate, sodium hydride and the like.

As the halogenating agent, there can be mentioned, for example, phosphorus oxychloride, phosphorus oxybromide, phosphorus trichloride, phosphorus pentachloride, thionyl chloride and the like.

As the sulfonylating agent, there can be mentioned, for example, methanesulfonyl chloride, p-toluenesulfonyl chloride and the like.

Each of the halogenating agent, the sulfonylating agent and the base as an optional component is used in an amount of at least 1 mole, preferably 1–2 moles, per mole of the compound of the general formula [VII] or its salt.

This reaction can be effected usually at −10° to 100° C., preferably 0° to 40° C., for 10 minutes to 30 hours.

The obtained compound of the general formula [VIII] may be used as it is, in the subsequent reaction without being isolated.

(4) The compound of the general formula [VIII] is reacted with a compound of the general formula [IX] or its salt in the presence or absence of a catalyst in the presence or absence of a base to obtain a compound of the general formula [Ib] or its salt.

The solvent to be used in this reaction can be any solvent unless it adversely affects the reaction. There can be mentioned, for example, the same solvents as mentioned in (3) of Production Process 2.

As the catalyst to be used optionally, there can be mentioned, for example, potassium iodide, sodium iodide and the like.

The catalyst is used in an amount of 0.1–1 mole per mole of the compound of the general formula [VIII].

As the base to be used optionally, there can be mentioned, for example, the same bases as mentioned in (3) of Production Process 2.

Each of the compound of the general formula [IX] or its salt and the base as an optional component is used in an amount of at least 1 mole, preferably 1–20 moles, per mole of the compound of the general formula [VIII].

This reaction can be effected usually at 10°–150° C., preferably 20°–100° C. for 10 minutes to 20 hours.

Production Process 3

(1) A compound of the general formula [II] is reacted with a compound of the general formula [X] or its salt in the presence or absence of a base to obtain a compound of the general formula [XI] or its salt.

This reaction can be effected in accordance with the same method as mentioned in Production Process 1.

(2) The compound of the general formula [XI] or its salt is reacted with a sulfonylating agent in a solvent in the presence or absence of a base to obtain a compound of the general formula [XII] or its salt.

The solvent to be used in this reaction can be any solvent unless it adversely affects the reaction. There can be mentioned, for example, the same solvents as mentioned in (3) of Production Process 2.

As the base to be used optionally, there can be mentioned, for example, the same bases as mentioned in (3) of Production Process 2.

As the sulfonylating agent, there can be mentioned, for example, p-toluenesulfonyl chloride and the like.

Each of the sulfonylating agent and the base as an optional component is used in an amount of at least 0.95 mole, preferably 1–2 moles, per mole of the compound of the general formula [XI] or its salt.

This reaction can be effected usually at −10° to 100° C., preferably 0° to 40° C., for 10 minutes to 30 hours.

The obtained compound of the general formula [XII] or its salt may be used in the subsequent reaction without being isolated.

(3) The compound of the general formula [XII] or its salt is subjected to conventional reaction for protection of hydroxyl group to obtain a compound of the general formula [XIII].

The reaction can be effected in accordance with per se known methods, for example, the method described in Protective Groups in Organic Synthesis [Theodra W. Green (1981), John Wiley & Sons, Inc.] or a method similar thereto.

The obtained compound of the general formula [XIII] may be used in the subsequent reaction without being isolated.

(4) The compound of the general formula [XII] or its salt or the compound of the general formula [XIII] is reacted with a compound of the general formula [IX] or its salt is presence or absence of a base to obtain a compound of the general formula [Ic] or its salt. as described in (4) of Production Process 2.

Production Process 4

(1) A compound of the general formula [XIV] is reacted with a compound of the general formula [XV] to obtain a compound of the general formula [XVI] or its salt.

The solvent to be used in this reaction can be any solvent unless it adversely affects the reaction. There can be mentioned, for example, ethers such as diethyl ether, tetrahydrofuran, dioxane and the like; and aromatic hydrocarbons such as benzene, toluene and the like. These solvents can be used alone or in admixture of two or more.

In this reaction, the compound of the general formula [XV] is used in an amount of 0.8–100 moles, preferably 0.8–10 moles, per mole of the compound of the general formula [XIV].

This reaction can be effected usually at −78° to 100° C., preferably −78° to 50° C. for 5 minutes to 24 hours.

The obtained compound of the general formula [XVI] or its salt may be used in the subsequent reaction without being isolated.

Incidentally, the compound of the general formula [XV] to be used in this reaction can be produced according to a per se known method, for example, the method described in Bull. Soc. Chim. Fr., 1967 (5), pp. 1533–40.

(2) The compound of the general formula [XVI] or its salt is reacted with a compound of the general formula [IX] or its salt in the presence or absence of a base to obtain a compound of the general formula [Id] or its salt.

The solvent to be used in this reaction can be any solvent unless it adversely affects the reaction. There can be mentioned, for example, halogenated hydrocarbons such as methylene chloride, chloroform and the like; ethers such as tetrahydrofuran, dioxane and the like; alcohols such as ethanol, propanol, butanol and the like; nitriles such as acetonitrile and the like; and amides such as N,N-dimethylformamide and the like. These solvents can be used alone or in admixture of two or more.

As the base to be used Optionally, there can be mentioned, for example, the same bases as mentioned in (3) of Production Process 2.

Each of the compound of the general formula [IX] or its salt and the base as an optional component is used in an amount of at least 1 mole, preferably 1–20 moles, per mole of the compound of the general formula [XVI] or its salt.

This reaction can be effected usually at 10°–150° C., preferably 20°–100° C., for 10 minutes to 20 hours.

In the above production processes, the reactants or base can also be used as solvent depending on the nature of the reactants or base.

In the above production processes, when the compounds of the general formulas [II], [III], [IIIa], [IV], [V], [VI], [VII], [VIII], [IX], [X], [XI], [XII], [XIII], [XIV], [XV] and

[XVI], have isomers (e.g. optical isomers, geometrical isomers, tautomers), the compounds can be used in any isomer form. Further, the compounds can be used in a hydrate form, a solvate form or any crystal form.

When the compounds of the general formulas [II], [III], [IIIa], [IV], [V], [VI], [VII], [VIII], [IX], [XII], [XIII], [XIV], [XV], [XVI], [I], [Ia], [Ib], [Ic] and [Id] have a hydroxyl group, an amino group or a carboxyl group, it is possible to previously protect these groups with a conventional protective group and to remove, after the reaction, the protective group, if necessary, according to a per se known method.

The compound thus obtained may be subjected to conventional isolation and purification procedures such as column chromatography, crystallization, distillation, extraction and the like.

The 1,2-ethanediol derivative of the general formula [I] or its salt can be converted into other 1,2-ethanediol derivative of the general formula [I] or its salt by subjecting the former compound to appropriate combination of per se known reactions such as oxidation reaction, reduction reaction, addition reaction, acylation reaction, alkylation reaction, sulfonylation reaction, deacylation reaction, substitution reaction, dehydration reaction, hydrolysis reaction and the like.

The compound of the general formula [II] which is the starting material for producing the compound of this invention can be produced by per se known processes, for example, the process described in JACS, vol. 87, p. 1353 (1965) and the process described in Shin Jikken Kagaku Koza, vol. 14, p. 579 (1977), Maruzen.

The compound of this invention, when used as a drug, may be appropriately mixed with excipients such as filler, carrier, diluent and the like and can be formed into tablets, capsules, powders, granules, fine granules, pills, suspensions, emulsions, liquids, syrups, injections, etc. according to conventional methods. These drugs can be administered orally or parenterally. The dosage route, dose and number of administrations can be appropriately varied depending upon the age, weight and symptom of patient, but in the case of oral administration, generally 0.01–500 mg of the present compound can be administered daily to an adult patient in one to several portions.

Next, the pharmacological activities of representative compounds of this invention are described.

The numbers of the test compounds used in the following pharmacological tests refer to the numbers of the compounds shown in Production Examples appearing hereinafter.

1. Effect of test compound on hypoxia

A test compound dissolved in physiological saline (100 mg/kg) was orally administered to a ddY female mouse (5–6 weeks old, each group consisting of 10 mice). After 1 (or 30 minutes*) hour from the administration, each mouse was placed in a 300-ml glass chamber, and a gas mixture consisting of 4% of oxygen and 96% of nitrogen was passed through the chamber at a rate of 5 liters/min. A time from the start of gas passing to the death of each mouse was measured.

To a control mice group was orally administered only physiological saline.

The antihypoxic activity of the test compound was calculated from the following formula:

$$\frac{\text{Mean survival time of mice of administration group}}{\text{Mean survival time of mice of control group}} \times 100 \ (\%)$$

The results are shown in Table 1.

TABLE 1

| Compound No. | Antihypoxic activity (%) | Compound No. | Antihypoxic activity (%) |
|---|---|---|---|
| 1 | 155 | 48 | 160 |
| 2 | 119 | 49 | 151 |
| 3 | 245* | 54 | 137 |
| 9 | 113 | 55 | 207 |
| 14 | 184* | 56 | 182 |
| 15 | 194* | 58 | 133 |
| 16 | 116 | 61 | 184* |
| 19 | 168* | 62 | 127 |
| 23 | 241* | 67 | 247* |
| 27 | 201* | 71 | 147 |
| 33 | 224* | 83 | 177* |
| 34 | 221 | 84 | 175* |
| 36 | 139 | 86 | 130* |
| 37 | 148 | 87 | 179 |
| 42 | 194 | 89 | 156* |
| 46 | 150* | 92 | 169 |
| 47 | 165* | 95 | 164 |
| 96 | 176* | 204 | 176* |
| 97 | 138* | 207 | 136* |
| 98 | 164* | 208 | 242* |
| 100 | 171* | 209 | 148* |
| 102 | 140* | 211 | 177* |
| 104 | 160* | 213 | 149 |
| 119 | 175* | 215 | 197 |
| 120 | 162* | 218 | 157* |
| 121 | 149* | 219 | 222* |
| 122 | 142* | 220 | 183* |
| 123 | 140* | 221 | 183* |
| 125 | 172* | 222 | 152* |
| 126 | 172* | 223 | 149* |
| 129 | 158* | 224 | 155 |
| 131 | 167* | 225 | 157* |
| 132 | 133* | 228 | 144 |
| 134 | 201* | 229 | 123 |
| 137 | 163* | 230 | 177 |
| 139 | 162* | 231 | 246 |
| 151 | 182 | 232 | 150 |
| 152 | 180 | 236 | 177 |
| 153 | 185 | 237 | 149 |
| 167 | 165 | 238 | 123 |
| 180 | 176* | 239 | 150 |
| 181 | 132 | 243 | 159 |
| 187 | 153* | 246 | 128 |
| 188 | 144* | 247 | 124 |
| 195 | 176* | 250 | 145* |
| 197 | 164* | 251 | 186* |
| 203 | 177* | 252 | 190* |
| 256 | 154 | 342 | 157* |
| 259 | 155* | 343 | 160* |
| 260 | 124 | 344 | 268* |
| 261 | 126 | 345 | 185* |
| 271 | 150* | 347 | 162* |
| 272 | 185* | 348 | 251* |
| 279 | 198 | 349 | 209* |
| 282 | 160* | 350 | 147* |
| 283 | 183 | 353 | 132* |
| 289 | 157* | 357 | 189* |
| 302 | 182* | 358 | 211* |
| 303 | 168 | 365 | 155* |
| 309 | 198* | 368 | 135* |
| 312 | 221* | 369 | 143* |
| 313 | 154* | 375 | 156* |
| 320 | 212* | 377 | 221* |
| 325 | 217* | 383 | 293* |
| 327 | 160* | 385 | 161* |
| 330 | 242* | 386 | 169* |
| 332 | 230* | 387 | 228* |
| 334 | 246* | 388 | 213* |
| 336 | 224* | 390 | 248* |

TABLE 1-continued

| Compound No. | Antihypoxic activity (%) | Compound No. | Antihypoxic activity (%) |
| --- | --- | --- | --- |
| 337 | 309* | 394 | 241* |
| 338 | 144* | 396 | 316* |
| 339 | 131* | 398 | 171* |
| 340 | 163* | 405 | 137* |
| 410 | 153* | 419 | 185** |
| 411 | 167* | 421 | 274* |
| 413 | 157* | 422 | 256* |
| 414 | 172* | 423 | 279* |
| 415 | 129* | 428 | 274* |
| 418 | 191** | 429 | 251* |

Note:
*Mice were placed in the chamber after 30 minutes from the administration instead of after 1 hr from the administration.
**25 mg/kg of the test compound was administered to mice instead of 100 mg/kg of the test compound, and mice were placed in the chamber after 30 minutes from the administered instead of after 1 hour from the administration.

2. Effect of test compound on amnesia (1) Electroconvulsive shock (ECS)-induced amnesia A test compound dissolved in physiological saline was intraperitoneally administered to a ddY male mouse (5–6 weeks old, each group consisting of 10 mice). The acquisition trial in passive avoidance task was carried out after 1 hour from the administration. Each mouse was placed in the bright compartment of a two-compartment step-through type passive avoidance apparatus consisting of a bright compartment and a dark compartment (MPA-100M manufactured by Muromachi Kikai). When the mouse entered the dark compartment, the guilotine door of the dark compartment was closed; after 0.5 second, an inescapable footshock (1.6 mA, 3 seconds) was delivered. Immediately thereafter, ECS (25 mA, 0.5 second) was applied through the both eyes of the mouse. After 24 hours, in the retention trial, the mouse was again placed in the bright compartment and the response latency for mouse to enter the dark compartment was measured. If the mouse avoided longer than 300 seconds, a ceiling score of 300 seconds was assigned.

A control mice group to which only physiological saline had been administered intraperitoneally, and response latency was also measured in the same manner.

Antiamnesic activity was taken as a median of the response latencies of the 10 mice and expressed by the following symbols:

−: 0–60 seconds
+: 61–100 seconds
++: 101–150 seconds
+++: 151–300 seconds

The results are shown in Table 2.

TABLE 2

| Compound No. | Dosage (mg/Kg) | Antiamnesic activity |
| --- | --- | --- |
| 2 | 3 | + |
| 3 | 3 | +++ |
| 8 | 3 | + |
| 15 | 3 | +++ |
| 19 | 3 | + |
| 23 | 10 | + |
| 29 | 3 | + |
| 44 | 10 | ++ |

TABLE 2-continued

| Compound No. | Dosage (mg/Kg) | Antiamnesic activity |
| --- | --- | --- |
| 48 | 3 | ++ |
| 52 | 3 | + |
| 53 | 3 | +++ |
| 58 | 10 | ++ |
| 61 | 3 | ++ |
| 67 | 3 | ++ |
| 70 | 3 | ++ |
| 76 | 3 | ++ |
| 78 | 3 | ++ |
| 115 | 3 | ++ |
| 159 | 3 | + |
| 160 | 3 | ++ |
| 170 | 3 | ++ |
| 176 | 3 | ++ |
| 189 | 3 | +++ |
| 228 | 10 | + |
| 229 | 3 | + |
| 235 | 10 | ++ |
| 237 | 3 | ++ |
| 239 | 10 | + |
| 243 | 3 | ++ |
| 252 | 3 | +++ |
| 261 | 3 | + |
| 266 | 3 | ++ |
| 315 | 3 | ++ |
| 316 | 3 | + |
| 319 | 10 | ++ |

(2) Effect of test compound on cycloheximide-induced amnesia

It was reported by Yamazaki et al. [Drugs, Mind and Action, vol. 3, pp. 127–136 (1983)] that cycloheximide interfers with the retrieval process of memory of mouse. Hence, the following test was carried out.

A test was carried out in accordance with the method described in Drugs, Mind and Action, vol. 3, pp. 127–136 (1983) and Folia Pharmacologica Japonica, vol. 89, pp. 243–252 (1987).

As the test apparatus, there was used a step-down type passive avoidance training box. It was a black acrylic resin box of 22 cm×22 cm×21 cm (height) whose floor portion consisted of a stainless steel grid and which had, at one corner of the floor grid, a platform of 7 cm×7 cm×2 cm (height).

Cycloheximide was dissolved in physiological saline, and injected subcutaneously at 120 mg/kg to a ddY male mouse (5–6 weeks old, each group consisting of 10 mice). In an acquisition trial, after 15 minutes from the administration, each mouse was placed on the platform in the above test apparatus. As soon as the mouse stepped down the platform, a 2 mA current was delivered for 2 seconds, immediately after which the mouse was returned to its home cage. A retention test was performed 24 hours after the acquisition. To each mouse which had been treated with cycloheximide was orally administered a test compound dissolved in physiological saline; after 30 minutes from the administration, the mouse was again placed on the platform and the response latency for mouse to step down was measured. If the mouse avoided longer than 300 seconds, a ceiling score of 300 seconds was assigned.

A control mice group to which only physiological saline had been administered orally, and response latency was also measured in the same manner.

Antiamnesic activity was taken as a median of the response latencies of the 10 mice and expressed by the following symbols:

−: 0–60 seconds

+: 61–100 seconds
++: 101–150 seconds
+++: 151–300 seconds

The results are shown in Table 3.

TABLE 3

| Compound No. | Dosage (mg/Kg) | Antiamnesic activity |
|---|---|---|
| 1 | 3 | ++ |
| 7 | 10 | + |
| 9 | 10 | + |
| 14 | 3 | +++ |
| 15 | 3 | +++ |
| 16 | 10 | + |
| 25 | 3 | + |
| 28 | 10 | + |
| 42 | 3 | + |
| 48 | 3 | ++ |
| 49 | 3 | ++ |
| 54 | 3 | ++ |
| 56 | 3 | + |
| 60 | 3 | +++ |
| 65 | 3 | ++ |
| 82 | 3 | ++ |
| 83 | 3 | + |
| 84 | 10 | ++ |
| 100 | 3 | ++ |
| 110 | 10 | ++ |
| 112 | 3 | +++ |
| 113 | 3 | ++ |
| 115 | 3 | +++ |
| 147 | 3 | +++ |
| 151 | 3 | +++ |
| 153 | 3 | ++ |
| 165 | 10 | + |
| 178 | 3 | +++ |
| 181 | 10 | ++ |
| 194 | 3 | + |
| 196 | 3 | +++ |
| 219 | 3 | + |
| 220 | 10 | ++ |
| 221 | 10 | + |
| 228 | 3 | ++ |
| 229 | 10 | ++ |
| 230 | 3 | + |
| 232 | 10 | ++ |
| 233 | 3 | + |
| 234 | 3 | + |
| 235 | 3 | +++ |
| 238 | 3 | + |
| 240 | 3 | + |
| 241 | 3 | ++ |
| 242 | 3 | ++ |
| 244 | 3 | ++ |
| 245 | 10 | ++ |
| 246 | 3 | ++ |
| 248 | 3 | ++ |
| 251 | 3 | +++ |
| 252 | 30 | +++ |
| 257 | 3 | + |
| 260 | 3 | + |
| 261 | 3 | +++ |
| 262 | 3 | + |
| 263 | 10 | + |
| 266 | 30 | + |
| 280 | 10 | + |
| 312 | 10 | + |
| 317 | 3 | ++ |
| 320 | 3 | ++ |
| 324 | 10 | ++ |
| 325 | 10 | ++ |
| 333 | 3 | + |
| 334 | 3 | + |
| 338 | 3 | ++ |
| 339 | 10 | + |
| 340 | 3 | + |
| 341 | 3 | + |
| 343 | 10 | ++ |

TABLE 3-continued

| Compound No. | Dosage (mg/Kg) | Antiamnesic activity |
|---|---|---|
| 346 | 3 | + |
| 350 | 3 | ++ |
| 351 | 3 | + |
| 352 | 3 | ++ |
| 353 | 3 | + |
| 358 | 10 | ++ |
| 360 | 10 | + |
| 365 | 3 | + |
| 367 | 3 | +++ |
| 368 | 3 | + |
| Control | — | — |

3. Inhibitory activity for acetylcholinesterase

A test was conducted in accordance with the method of Ellman et al. [Biochem. Pharmacol., vol. 7, pp. 88–95, 1961].

That is, acetylthiocholine (as a substrate) was added to a phosphate buffer solution containing 5,5'-dithiobis-(2-nitrobenzoic acid) (DTNB), a test compound and a mouse cerebral homogenate (as an acetylcholinesterase source). The resulting mixture was incubated, and the amount of the resulting 5-thio-2-nitrobenzoic acid was photometrically measured at 412 nm.

The inhibitory activity for acetylcholinesterase of the test compound was expressed by the inhibition (%) when the final concentration of the test compound was 10 µg/ml.

The results are shown in Table 4.

TABLE 4

| Compound No. | Inhibition (%) | Compound No. | Inhibition (%) |
|---|---|---|---|
| 6 | 13 | 78 | 90 |
| 30 | 22 | 83 | 93 |
| 34 | 26 | 86 | 50 |
| 37 | 45 | 89 | 44 |
| 38 | 36 | 90 | 52 |
| 40 | 26 | 97 | 38 |
| 47 | 38 | 103 | 36 |
| 48 | 51 | 113 | 45 |
| 54 | 83 | 165 | 24 |
| 55 | 22 | 182 | 38 |
| 58 | 45 | 190 | 76 |
| 60 | 71 | 222 | 83 |
| 61 | 89 | 223 | 74 |
| 62 | 78 | 224 | 36 |
| 65 | 62 | 225 | 43 |
| 67 | 90 | 228 | 30 |
| 70 | 91 | 230 | 25 |
| 71 | 87 | 233 | 59 |
| 72 | 92 | 237 | 44 |
| 73 | 89 | 239 | 22 |
| 241 | 31 | 341 | 61 |
| 246 | 30 | 342 | 67 |
| 247 | 26 | 350 | 42 |
| 260 | 43 | 352 | 26 |
| 302 | 38 | 372 | 30 |
| 319 | 30 | 377 | 23 |
| 322 | 20 | 386 | 47 |
| 329 | 45 | 405 | 59 |
| 336 | 21 | | |

4. Acute toxicity

A test compound dissolved in physiological saline was intravenously administered to a group of 3 ddY male mice (5–6 weeks old) to examine the acute toxicity of the test compound.

As a result, test compound Nos. 1, 2, 3, 6, 8, 9, 15, 16, 25, 30, 33, 34, 38, 40, 42, 44, 46, 52, 53, 54, 65, 67, 70, 71, 112, 119, 120, 126, 132, 147, 151, 159, 160, 170, 176, 178, 182, 190, 194, 209, 219, 220, 221, 229, 235, 236, 240, 251, 256, 279, 283, 309, 312, 313, 315, 316,319, 325, 327,337, 360, 368,369, 375, 377, 385, 390 and 396 gave no death case at 50 mg/kg.

It is easily appreciated from the above test results that the compound of this invention is excellent in antihypoxic activity, antiamnesic activity and inhibitory activity for acetylcholinesterase and has low toxicity.

From the above result, it is also easily appreciated that the cerebral function-improving agent of this invention is useful for treating cerebrovascular dementia, senile dementia, Alzheimer's dementia, sequelae of ischemic encephalopathy and cerebral apoplexy.

Next, the process for producing the compound of this invention is specifically described by way of Production Examples.

In the Production Examples, the mixing ratio of eluant is by volume in all cases and, as the carrier in column chromatography, there was used a silica gel (Kieselgel 60, Art. 7734) manufactured by Merck Co.

The abbreviations used in the Production Examples have the following meanings.

Me: methyl, Et: ethyl, i-Pr: isopropyl, t-Bu: tert-butyl, Ac: acetyl, Ph: phenyl, DPM: diphenylmethyl, Bz: benzyl, Tr: trityl, IPA: isopropyl alcohol, IPE: diisopropyl ether, PTS: p-toluenesulfonic acid.

In the following sentences and tables, the substances in [ ] refer to solvents used in recrystallization.

PRODUCTION EXAMPLE 1

(1) A mixture of 10.8 g of (L)-dibenzoylcystine, 1.6 g of lithium borohydride, 2.4 g of tert-butanol and 180 ml of tetrahydrofuran was refluxed for 1 hour and then cooled to −60° C. Thereto was added 6.1 g of 4-benzyloxyphenacyl bromide. The mixture was stirred for 30 minutes at the same temperature and further for 3 hours at −40° to −30° C. The reaction mixture was added to a mixture of 100 ml of water and 200 ml of diethyl ether. The organic layer was separated, washed with water, a saturated aqueous sodium hydrogencarbonate solution and a saturated aqueous sodium chloride solution in this order, and dried over anhydrous magnesium sulfate. The solvent was removed by distillation under reduced pressure. The residue thus obtained was purified by column chromatography (eluant:toluene) to obtain 2.8 g of (S)-1-(4-benzyloxyphenyl)-2-bromoethanol.

(2) 2.8 g of (S)-1-(4-benzyloxyphenyl)-2-bromoethanol was dissolved in a mixed solvent of 20 ml of methanol and 10 ml of tetrahydrofuran. To the solution was added a solution of 0.8 g of potassium hydroxide dissolved in 4 ml of water, with ice cooling. The mixture was stirred for 5 minutes at the same temperature and further for 10 minutes at room temperature. The reaction mixture was added to a mixture of 50 ml of diethyl ether and 50 ml of ice water. The organic layer was separated. The aqueous layer was extracted with 25 ml of diethyl ether. The extract was combined with the previously separated organic layer. The combined organic layer was washed with water and a saturated aqueous sodium chloride solution in this order, and dried over anhydrous magnesium sulfate. The solvent was removed by distillation under reduced pressure to obtain 1.4 g of (S)-2-(4-benzyloxyphenyl)oxirane.

Melting point: 56°–61° C.

Optical rotation: $[\alpha]_D^{25}=+5.2°$ (C=2, CHCl$_3$)

The following compounds were obtained in the same manner.

o (S)-2-(3-Methylphenyl)oxirane $[\alpha]_D^{25}=+15.7°$ (C=2, CHCl$_3$)

o (S)-2-(4-Phenoxyphenyl)oxirane $[\alpha]_D^{25}=+12.5°$ (C=4, CHCl$_3$)

PRODUCTION EXAMPLE 2

(1) A solution of 23 g of (+)-diisopinocamphenylchloroborane dissolved in 30 ml of tetrahydrofuran was cooled to −25° C. Thereto was added 12 g of 4-benzyloxyphenacyl bromide. The resulting mixture was stirred for 4 hours at −20° to −15° C. The reaction mixture was added to a mixture of 150 ml of diethyl ether and 100 ml of ice water. The organic layer was separated, washed with water and a saturated aqueous sodium chloride solution in this order, and dried over anhydrous magnesium sulfate. The solvent was removed by distillation under reduced pressure. The residue thus obtained was purified by column chromatography (eluant:hexane:toluene =1:2) to obtain 6.8 g of (R)-1-(4-benzyloxyphenyl)-2-bromoethanol.

(2) 6.0 g of (R)-1-(4-benzyloxyphenyl)-2-bromoethanol was dissolved in a mixed solvent of 50 ml of methanol and 25 ml of tetrahydrofuran. Thereto was added a solution of 1.5 g of potassium hydroxide dissolved in 5 ml of water, with ice cooling. The resulting mixture was stirred for 5 minutes at the same temperature and further for 10 minutes at room temperature. The reaction mixture was added to a mixture of 100 ml of diethyl ether and 100 ml of ice water. The organic layer was separated. The aqueous layer was extracted with 50 ml of diethyl ether. The extract was combined with the previously separated organic layer. The combined organic layer was washed with water and a saturated aqueous sodium chloride solution in this order, and dried over anhydrous magnesium sulfate. The solvent was removed by distillation under reduced pressure to obtain 3.7 g of (R)-2-(4-benzyloxyphenyl)oxirane.

Melting point: 58°–67° C.

Optical rotation: $[\alpha]_D^{26}=-14.4°$ (C=2, CHCl$_3$)

The following compounds were obtained in the same manner.

o (R)-2-(3-Methylphenyl)oxirane $[\alpha]_D^{27}=-18.6°$ (C=2, CHCl$_3$)

o (R)-2-(4-Phenoxyphenyl)oxirane $[\alpha]_D^{25}-11.3°$ (C=2, CHCl$_3$)

(3) A solution of 7.5 g of (+)-diisopinocamphenylchloroborane dissolved in 15 ml of tetrahydrofuran was cooled to −25° C. Thereto was added 4 g of 5-bromoacetylbenzo[b]thiophene. The resulting mixture was stirred for 4 hours at −20° C. to −15° C. The reaction mixture was added to a mixture of 80 ml of ethyl acetate and 80 ml of ice water. The organic layer was separated, washed with water and a saturated aqueous sodium chloride solution in this order, and dried over anhydrous magnesium sulfate. The solvent was removed by distillation under reduced pressure. The residue thus obtained was purified by column chromatography (eluant:hexane:ethyl acetate =10:1) to obtain 3.8 g of (R)-1-(benzo[b]thiophen-5-yl)-2-bromoethanol.

(4) 3.5 g of (R)-1-(benzo[b]thiophen-5-yl)-2-bromoethanol was dissolved in a mixed solvent of 20 ml of methanol and 10 ml of tetrahydrofuran. Thereto was added a solution of 1.5 g of potassium hydroxide dissolved in 5 ml of water, with ice cooling. The resulting mixture was stirred for 5 minutes at the same temperature and further for 10 minutes at room temperature. The reaction mixture was added to a mixture of 60 ml of diethyl ether and 60 ml of ice water. The organic layer was separated. The aqueous layer was extracted with 30 ml of diethyl ether. The extract was combined with the previously separated organic layer. The combined organic layer was washed with water and a saturated aqueous sodium chloride solution in this order, and dried over anhydrous magnesium sulfate. The solvent was removed by distillation under reduced pressure to obtain 1.9 g of (R)-2-(benzo[b]thiophen-5-yl)oxirane.

Melting point: 72°–76° C.

Optical rotation: $[\alpha]_D = -8.4°$ (C=2, CHCl$_3$)

The following compounds were obtained in the same manner.

O(S)-2-(benzo[b]thiophen-5-yl)oxirane.

Melting point: 72°–75° C.

$[\alpha]_D = +8.8°$ (C=2, CHCl$_3$).

PRODUCTION EXAMPLE 3

3.4 g of potassium tert-butoxide was added to 31 ml of 2-(N,N-dimethylamino)ethanol. The resulting mixture was heated to 80° C. Thereto was dropwise added 7.7 g of 2-(3-fluorophenyl)oxirane over 40 minutes. The mixture was stirred for 3 hours at the same temperature. The reaction mixture was added to a mixture of 200 ml of ice water and 200 ml of ethyl acetate. The organic layer was separated. To the organic layer was added 50 ml of water. The mixture was adjusted to pH 1 with 6N hydrochloric acid. The aqueous layer was separated and mixed with 100 ml of chloroform. The resulting mixture was adjusted to pH 11 with a 2N aqueous sodium hydroxide solution. The organic layer was separated, washed with water, and dried over anhydrous magnesium sulfate. The solvent was removed by distillation under reduced pressure. The residue thus obtained was purified by column chromatography (eluant:chloroform/ethanol=5/1). The resulting oily product was dissolved in 25 ml of acetone. Hydrogen chloride gas was blown into the solution. The resulting crystals were collected by filtration, washed with acetone and dried to obtain 3.1 g of 2-[2-(N,N-dimethylamino)ethoxy]-1-(3-fluorophenyl)ethanol hydrochloride (compound No. 1).

Melting point: 164°–165° C. [EtOH]

The compounds shown in Table 5 were obtained in the same manner.

In Table 5, $R^1$, $R^2$, $R^3$, $R^{4a}$, $R^{4b}$, $R^6$, na and nb each show a substituent or integer used in the following formula.

TABLE 5

$$R^1-CH-CH-O-(CH)_{na}-(CH)_{nb}-R^6$$
$$\underset{OR^2}{|} \quad \underset{R^3}{|} \quad \underset{R^{4a}}{|} \quad \underset{R^{4b}}{|}$$

| Compound No. | $R^1$ | $R^2$ | $R^3$ | $R^{4a}$ | $R^{4b}$ | $R^6$ | na | nb | Addition salt | Melting point (°C.) |
|---|---|---|---|---|---|---|---|---|---|---|
| 2 | 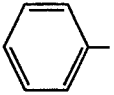 | H | H | H | H | −N(Me)(Me) | 1 | 1 | HCl | 184–185 [EtOH] |
| 3*a | 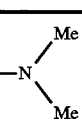 (R-form) | " | " | " | " | " | " | " | " | 174.5–175 [Me$_2$CO—EtOH] |
| 4*b | 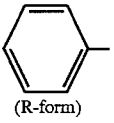 (S-form) | H | H | H | H | −N(Me)(Me) | 1 | 1 | HCl | 174.5–175 [Me$_2$CO—EtOH] |
| 5 | 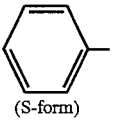 | " | " | " | " | −N(Et)(Et) | " | " | — | Oily |
| 6 | " | " | " | " | " | 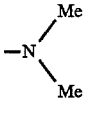 | " | " | HCl | 173–174 [EtOH—Et$_2$O] |
| 7 | " | " | " | " | " | 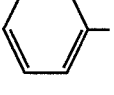 | " | " | " | 163.5–164.5 [EtOH—Et$_2$O] |
| 8 | 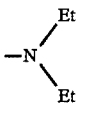 | H | H | H | H |  | 1 | 1 | HCl | 153–154.5 [EtOH—Et$_2$O] |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 9 | " | " | " | " | " | —N(pyrrolidinone) | " | " | — | Oily |
| 10 | " | " | " | " | " | —N(i-Pr)₂ | " | " | " | " |
| 11 | " | " | " | " | " | —N(imidazole) | " | " | " | " |
| 12 | phenyl | H | H | H | H | —NMe₂ | 2 | 1 | — | Oily |
| 13 | " | " | " | " | " | " | 3 | 3 | HCl | Amorphous |
| 14 | o-Me-phenyl | " | " | " | " | " | 1 | 1 | " | 198–199 [EtOH] |
| 15 | m-Me-phenyl | " | " | " | " | " | " | " | " | 165–166 [IPA] |
| 16 | p-Me-phenyl | H | H | H | H | —NMe₂ | 1 | 1 | HCl | 181.5–183 [EtOH] |
| 17 | p-Et-phenyl | " | " | " | " | " | " | " | " | 201.5–203 [IPA] |
| 18 | p-i-Pr-phenyl | " | " | " | " | " | " | " | " | 194.5–196.5 [EtOH] |
| 19 | p-t-Bu-phenyl | " | " | " | " | " | " | " | " | 251–252 [EtOH] |
| 20 | m-Me-phenyl | H | H | H | H | —N(morpholino) | 1 | 1 | HCl | 141–143 [EtOH—Et₂O] |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 21 | " | " | " | " | " | −N(piperidine) | " | " | " | 136.5–137.5 [EtOH—Et₂O] |
| 22 | " | " | " | " | " | −N(i-Pr)₂ | " | " | — | Oily |
| 23 | " | " | " | " | " | −NMe₂ | 2 | 2 | " | " |
| 24 | 3-Me-C₆H₄ | H | H | H | H | −NMe₂ | 1 | 2 | — | Oily |
| 25 | " | " | " | " | " | −N(pyrrolidinone) | " | 1 | " | " |
| 26 | 3,4-Me₂-C₆H₃ | " | " | " | " | −NMe₂ | " | " | HCl | 184–185 [EtOH] |
| 27 | 3,5-Me₂-C₆H₃ | " | " | " | " | " | " | " | " | 158–159 [IPA] |
| 28 | 3-Me-C₆H₄ | H | H | Me | H | −NMe₂ | 1 | 1 | — | Oily |
| 29 | " | " | " | H | Me | " | " | " | " | " |
| 30 | C₆H₅ | " | Me | " | H | " | " | " | HCl | 190–191 [MeOH—Et₂O] |
| 31 | 2-Cl-C₆H₄ | " | H | " | " | " | " | " | " | 203–204 [EtOH] |

TABLE 5-continued $$R^1-\underset{\underset{OR^2}{|}}{CH}-\underset{\underset{R^{4a}}{|}}{CH}-O-(CH)_{na}(\underset{\underset{R^{4a}}{|}}{CH})_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 32 | 3-Cl-C₆H₄ | H | H | H | H | -N(Me)₂ | 1 | 1 | HCl | 170–171 [Me₂CO] |
| 33 | 4-Cl-C₆H₄ | " | " | " | " | " | " | " | " | 188.5–190 [MeOH—Et₂O] |
| 34 | 3,4-Cl₂-C₆H₃ | " | " | " | " | " | " | " | " | 156.5–157.5 [EtOH—Et₂O] |
| 35 | 2,4-Cl₂-C₆H₃ | " | " | " | " | " | " | " | " | 184–184.5 [EtOH] |
| 36 | 3-Cl-C₆H₄ | H | H | H | H | -N(piperidine) | 1 | 1 | HCl | 131–132 [EtOH—Et₂O] |
| 37 | 3,4-Cl₂-C₆H₃ | " | " | " | " | " | " | " | " | 178.5–179.5 [EtOH—Et₂O] |
| 38 | 4-F-C₆H₄ | " | " | " | " | -N(Me)₂ | " | " | " | 171–172 [EtOH] |
| 39 | 2,4-F₂-C₆H₃ | " | " | " | " | " | " | " | " | 182–182.5 [EtOH] |
| 40 | 3-NO₂-C₆H₄ | H | H | H | H | -N(Me)₂ | 1 | 1 | HCl | 228–229.5 [EtOH—Et₂O] |
| 41 | 4-CF₃-C₆H₄ | " | " | " | " | " | " | " | " | 193.5–194.5 [EtOH] |

TABLE 5-continued $$R^1-\underset{OR^2}{\underset{|}{CH}}-\underset{}{\overset{R^3}{\underset{|}{CH}}}-O-(CH_2)_{na}-\underset{R^{4a}}{\overset{R^{4b}}{\underset{|}{(CH)}}}_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 42 | 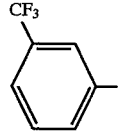 (3-CF₃-C₆H₄) | " | " | " | " | " | " | " | " | 168.5–169.5 [EtOH—Et₂O] |
| 43 | 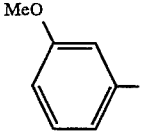 (3-MeO-C₆H₄) | " | " | " | " | " | " | " | " | 146–147 [EtOH] |
| 44 | 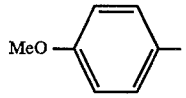 (4-MeO-C₆H₄) | H | H | H | H | —N(Me)₂ | 1 | 1 | HCl | 171–173 [EtOH] |
| 45 |  (3,4,5-(MeO)₃-C₆H₂) | " | " | " | " | " | " | " | PTS | 140–141 [EtOH] |
| 46 | 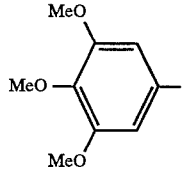 (4-MeS-C₆H₄) | " | " | " | " | " | " | " | HCl | 179.5–181.5 [EtOH—Et₂O] |
| 47 | 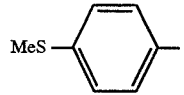 (3-BzO-C₆H₄) | " | " | " | " | " | " | " | " | 169–171 [EtOH] |
| 48 | 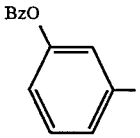 (4-BzO-C₆H₄) | H | H | H | H | —N(Me)₂ | 1 | 1 | HCl | 186–186.5 [EtOH] |
| 49 | 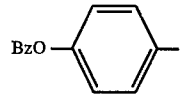 (4-Cl-C₆H₄-CH₂-O-C₆H₄) | " | " | " | " | " | " | " | " | 188–188.5 [EtOH] |
| 50 |  (4-MeO-C₆H₄-CH₂-O-C₆H₄) | " | " | " | " | " | " | " | " | 199–199.5 [MeOH—EtOH] |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 51 | 3,4-(BzO)₂-C₆H₃- | " | " | " | " | " | " | " | — | Oily |
| 52 | 3,4-(OCH₂O)-C₆H₃- | H | H | H | H | -N(Me)Me | 1 | 1 | HCl | 149.5–151 [Me₂CO] |
| 53 | 3-PhO-C₆H₄- | " | " | " | " | " | " | " | " | 140–141 [EtOH—Et₂O] |
| 54 | 4-PhO-C₆H₄- | " | " | " | " | " | " | " | " | 174.5–176.5 [MeCN] |
| 55 | 4-MeO-C₆H₄-C₆H₄- | " | " | " | " | " | " | " | " | 229–231 [MeCN] |
| 56 | 4-Ph-C₆H₄- | H | H | H | H | -N(Me)Me | 1 | 1 | HCl | 217.5–218.5 [EtOH] |
| 57 | 3-Ph-C₆H₄- | " | " | " | " | " | " | " | " | 138–140 [EtOH—Et₂O] |
| 58 | 3-Bz-C₆H₄- | " | " | " | " | " | " | " | " | 153–154 [EtOH] |
| 59 | 4-Bz-C₆H₄- | " | " | " | " | " | " | " | " | 179–181 [EtOH] |
| 60 | C₆H₅- | H | H | H | H | 4-(N-Bz)piperidinyl | 1 | 1 | — | Oily |
| 61 | 3-Me-C₆H₄- | " | " | " | " | " | " | " | " | " |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 62 | 4-F-C₆H₄- | " | " | " | " | " | " | " | " | 50–52 |
| 63 | 4-F-C₆H₄- | | | | | -N(piperidine) | " | " | HCl | 160–161 [EtOH—Et₂O] |
| 64 | 4-F-C₆H₄- | H | H | H | H | -N(morpholine) | 1 | 1 | HCl | 151–152.5 [EtOH—Et₂O] |
| 65 | 2-Me-biphenyl-4-yl | " | " | " | " | -NMe₂ | " | " | " | 223–225 [EtOH—IPA] |
| 66 | 2-F-biphenyl-4-yl | " | " | " | " | " | " | " | " | 215–216 [MeOH—EtOH] |
| 67 | 4-(4-F-C₆H₄-O)-C₆H₄- | " | " | " | " | " | " | " | " | 180.5–181.5 [MeCN] |
| 68 | 4-(3-F-C₆H₄-O)-C₆H₄- | H | H | H | H | -NMe₂ | 1 | 1 | HCl | 168.5–169.5 [IPA] |
| 69 | 4-(4-Cl-C₆H₄-O)-C₆H₄- | " | " | " | " | " | " | " | " | 177.5–178.5 [MeCN] |
| 70 | 4-(2-Cl-C₆H₄-O)-C₆H₄- | " | " | " | " | " | " | " | " | 194.5–195 [MeCN] |
| 71 | 4-(4-MeO-C₆H₄-O)-C₆H₄- | " | " | " | " | " | " | " | " | 162–162.5 [IPA] |
| 72 | 4-(3,5-diMe-C₆H₃-O)-C₆H₄- | H | H | H | H | -NMe₂ | 1 | 1 | HCl | 171–172 [IPA] |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 73 | 2-fluoro-4-phenoxyphenyl | " | " | " | " | " | " | " | " | 162–162.5 [IPA] |
| 74 | 2-phenoxyphenyl | " | " | " | " | " | " | " | " | 147.5–148.5 [Me₂CO—Et₂O] |
| 75 | 4-phenoxyphenyl | " | " | " | " | " | 2 | " | — | Oily |
| 76 | 4-phenoxyphenyl | H | H | H | H | piperidino | 1 | 1 | HCl | 160–160.5 [IPA] |
| 77 | " | " | " | " | " | morpholino | " | " | " | 192.5–193 [MeCN] |
| 78 | " | " | " | " | " | 4-(N-Bz)piperidinyl | " | " | — | Oily |
| 79 | 2-benzoyloxyphenyl | " | " | " | " | NMe₂ | " | " | HCl | 124–125 [MeCN] |
| 80 | 4-benzoyloxyphenyl | H | H | H | H | NMe₂ | 2 | 1 | — | 121.5–123 [AcOEt—Et₂O] |
| 81 | 3-(methoxymethoxy)phenyl-CH₂O-(4-phenyl) | " | " | " | " | " | 1 | " | " | Oily |
| 82*c | 3-hydroxyphenyl-CH₂O-(4-phenyl) | " | " | " | " | " | " | " | HCl | 179–181 [EtOH] |
| 83 | 4-methoxyphenyl-O-(4-phenyl) | " | " | " | " | " | " | " | " | 189.5–190 [IPA] |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 84 | 2-pyridyl-CH₂-O-C₆H₄- | H | H | H | H | -N(Me)Me | 1 | 1 | 2HCl | 157–158 [EtOH] |
| 85 | 2-Me,1-PhO-C₆H₃- | " | " | " | " | " | " | " | HCl | 161–162.5 [IPA] |
| 86 | 3-pyridyl-CH₂-O-C₆H₄- | " | " | " | " | " | " | " | 2HCl | 157.5–159.5 [EtOH] |
| 87 | Ph-CH₂CH₂-O-C₆H₄- | " | " | " | " | " | " | " | HCl | 172–173 [IPA] |
| 88 | BzO-C₆H₄- | H | H | H | H | -N(Et)Et | 1 | 1 | — | Oily |
| 89 | Ph-CH₂CH₂-C₆H₄- | " | " | " | " | -N(Me)Me | " | " | HCl | 222.5–223.5 [EtOH] |
| 90 | 3-Me-C₆H₄- | " | " | " | " | -N(Et)Et | " | " | — | Oily |
| 91 | i-Pr-O-C₆H₄- | " | " | " | " | -N(Me)Me | " | " | HCl | 204.5–205 [EtOH—Me₂CO] |
| 92 | 2-thienyl-CH₂-O-C₆H₄- | H | H | H | H | -N(Me)Me | 1 | 1 | HCl | 168.5–169 [EtOH—AcOEt] |
| 93 | 3,4,5-(MeO)₃-C₆H₂-CH₂-O-C₆H₄- | " | " | " | " | " | " | " | " | 193–194 [EtOH—AcOEt] |
| 94 | CH₂=CH-CH₂-O-C₆H₄- | " | " | " | " | " | " | " | " | 154.5–156 [MeCN] |

TABLE 5-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 95 | 2-furyl-CH₂-O-C₆H₄- | " | " | " | " | " | " | " | " | 168.5–169.5 [EtOH—AcOEt] |
| 96 | 2,6-dichlorophenyl | H | H | H | H | -N(Me)₂ | 1 | 1 | HCl | 197–198 [IPA—AcOEt] |
| 97 | 3-chlorobenzyl-O-C₆H₄- | " | " | " | " | " | " | " | " | 176–178 [EtOH] |
| 98 | 2-OMe-4-(BzO)-C₆H₃- | " | " | " | " | " | " | " | " | 140.5–142 [IPA] |
| 99 | 2-chlorobenzyl-O-C₆H₄- | " | " | " | " | " | " | " | " | 181.5–182.5 [EtOH] |
| 100 | 4-(BzO)-C₆H₄- | H | H | H | H | -N(morpholino)-O | 1 | 1 | HCl | 170–170.5 [EtOH—Me₂CO] |
| 101 | 4-Me-benzyl-O-C₆H₄- | " | " | " | " | -N(Me)₂ | " | " | " | 199–199.5 [EtOH] |
| 102*ᵈ | phenyl | " | " | " | " | -NH₂ | " | " | 1/2 Fumaric acid | 181–182.5 |
| 103*ᵉ | 4-(BzO)-C₆H₄- (R-form) | " | " | " | " | -N(Me)₂ | " | " | HCl | 194–194.5 [EtOH—Me₂CO] |
| 104*ᶠ | 3-Me-phenyl | H | H | H | H | -N(Me)₂ | 1 | 1 | HCl | 164–165 [EtOH—Me₂CO] |

TABLE 5-continued $$R^1-CH-CH-O-(CH)_{na}-(CH)_{nb}-R^6$$
$$\phantom{R^1-CH-}|\phantom{CH-}|\phantom{O-(CH}|_{na}\phantom{-(CH}|_{nb}$$
$$\phantom{R^1-CH-CH-}OR^2\phantom{-O-(}R^{4a}\phantom{)_{na}-(}R^{4b}$$
$$\phantom{R^1-CH-}R^3$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 105*ᵍ | PhO—C₆H₄— (R-form) | " | " | " | " | " | " | " | " | 193–194 [MeCN] |
| 106*ʰ | Me—C₆H₄— (m-tolyl) | " | " | " | " | —N⁺(Me)₃ | " | " | 1/2 1,5-Naphthalene-disulfonic acid | Amorphous |
| 107*ⁱ | BzO—C₆H₄— (S-form) | " | " | " | " | —NMe₂ | " | " | HCl | 195–196 [EtOH—Me₂CO] |
| 108*ʲ | Me—C₆H₄— (S-form) | H | H | H | H | —NMe₂ | 1 | 1 | HCl | 163–164.5 [EtOH—Me₂CO] |
| 109*ᵏ | PhO—C₆H₄— (S-form) | " | " | " | " | " | " | " | " | 187.5–188.5 [MeCN] |
| 110*ʰ | BzO—C₆H₄— | " | " | " | " | —N⁺(Me)₃ | " | " | 1/2 1,5-Naphthalene-disulfonic acid | 168–170 (decomp.) |
| 111 | i-Pr—C₆H₄— (m-isopropylphenyl) | " | " | " | " | —NMe₂ | " | " | — | Oily |
| 112 | BzO—C₆H₄—CH(OH)—CH₂—O—C(Me)₂—NMe₂·HCl | | | | | | | | | 171–173 [EtOH—Et₂O] |

Note:
*ᵃ: Optical rotation: −43.3° (27° C., C = 3, EtOH)
*ᵇ: Optical rotation: +43.3° (24° C., C = 3, EtOH)
*ᶜ: Obtained by treating compound No. 81 with p-toluenesulfonic acid.
*ᵈ: A trityl group was used as an amino-protecting group.
*ᵉ: Optical rotation: −38.9° (28° C., C = 1.5, MeOH)
*ᶠ: Optical rotation: −45.8° (25° C., C = 1.5, MeOH)
*ᵍ: Optical rotation: −38.5° (25° C., C = 1.5, EtOH)
*ʰ: Obtained by reacting 1 mole of a dimethylamino form with 0.5 mole of dimethyl 1,5-naphthalenedisulfonate.
*ⁱ: Optical rotation: +37.3° (23° C., C = 1.5, MeOH)
*ʲ: Optical rotation: +40.2° (23° C., C = 1.5, MeOH)
*ᵏ: Optical rotation: +28.4° (23° C., C = 1.5, EtOH)

PRODUCTION EXAMPLE 4

A mixture of 5.00 g of 1-benzyl-4-hydroxypiperidine, 1.97 g of potassium tert-butoxide and 4 ml of dimethyl sulfoxide was heated to 80° C. Thereto was dropwise added 2.10 g of styrene oxide over 40 minutes. The resulting mixture was stirred for 3 hours at the same temperature. The reaction mixture was added to a mixture of 100 ml of ice water and 80 ml of ethyl acetate. The mixture was adjusted to pH 11.5 with 6N hydrochloric acid. The organic layer was separated, washed with water and a saturated aqueous sodium chloride solution in this order, and dried over anhydrous magnesium sulfate. The solvent was removed by distillation under reduced pressure. The residue thus obtained was purified by column chromatography (eluant:chloroform/ethanol=10/1). The resulting oily product was dissolved in 8 ml of ethanol. To the solution were added 1 ml of a 6N dry hydrogen chloride-ethanol solution and 20 ml of diethyl ether. The mixture was stirred for 30 minutes at room temperature. The resulting crystals were collected by filtration, washed with a mixture of 2 ml of ethanol and 2 ml of diethyl ether, and dried to obtain 930 mg of 2-(1-benzylpiperidin-4-yloxy)-1-phenylethanol hydrochloride (compound No. 113).

Melting point: 193°–195° C.

The compounds shown in Table 6 were obtained in the same manner.

In Table 6, $R^1$, $R^2$, $R^3$, $R^4$, $R^6$ and n each show a substituent or integer used in the following formula:

TABLE 6

$$R^1-CH(OR^2)-CH(R^3)-O-(CH(R^4))_n-R^6$$

| Compound No. | $R^1$ | $R^2$ | $R^3$ | $R^4$ | $R^6$ | n | Addition salt | Melting point (°C.) |
|---|---|---|---|---|---|---|---|---|
| 114 | m-Me-C6H4- | H | H | — | piperidin-4-yl (N-Bz) | 0 | HCl | 180–181.5 [IPA] |
| 115 | " | " | " | — | piperidin-3-yl (N-Bz) | " | " | 202–204 |
| 116 | Ph- | " | " | — | quinuclidin-3-yl | " | — | 119–120 |
| 117 | Ph- | H | H | H | 1-methylpiperidin-4-yl | 1 | HCl | 153–155 [Me₂CO—EtOH] |
| 118 | " | " | " | " | 1-methyl-1,2,3,6-tetrahydropyridin-4-yl | " | " | Oily |
| 119 | " | " | " | " | 1-methylimidazol-4-yl | " | — | 92–95 |
| 120 | " | " | " | " | pyridin-3-yl | " | HCl | Oily |
| 121 | p-BzO-C6H4- | H | H | H | pyridin-3-yl | 1 | — | 78–81 [AcOEt—IPE] |
| 122 | Ph- | " | " | " | pyridin-2-yl | " | HCl | 129.5–131.5 [AcOEt—IPE] |

TABLE 6-continued $$R^1-CH(OR^2)-CH(R^3)-O-(CH(R^4))_n-R^6$$

| Compound No. | R¹ | R² | R³ | R⁴ | R⁶ | n | Addition salt | Melting point (°C.) |
|---|---|---|---|---|---|---|---|---|
| 123 | " | " | " | " | 4-methylpyridine | " | " | 157.5–159.5 |
| 124 | " | " | " | " | N-Me piperidine | " | " | 137–138.5 [Me₂CO] |
| 125 | 3-Me-phenyl | H | H | H | pyridine | 1 | HCl | Oily |
| 126 | 3-Cl-phenyl | " | " | " | " | " | " | " |
| 127 | phenyl | " | " | " | 3-Br-pyridine | " | " | " |
| 128 | " | " | " | " | quinuclidine | | — | " |
| 129*¹ | phenyl (S-form) | H | H | H | pyridine | 1 | — | 61–61.5 [EtOH—IPE] |
| 130*² | phenyl (R-form) | " | " | " | " | " | " | 61–61.5 [EtOH—IPE] |
| 131 | 4-MeO-phenyl | " | " | " | " | " | " | 71.5–72 [EtOH—IPE] |
| 132*³ | phenyl | " | " | " | imidazole | " | " | 118–119.5 |
| 133*³ | phenyl | H | H | H | piperidine (NH) | 1 | HCl | 147.5–149 [IPA—AcOEt] |

TABLE 6-continued $$R^1-CH(OR^2)-CH(R^3)-O-(CH(R^4))_n-R^6$$

| Compound No. | R¹ | R² | R³ | R⁴ | R⁶ | n | Addition salt | Melting point (°C.) |
|---|---|---|---|---|---|---|---|---|
| 134*³ | phenyl (1R-form) | " | " | " | tetrahydro-1,3-thiazine (S, NH) | " | " | Oily |
| 135*³ | phenyl | " | " | " | pyrrolidine (NH) | " | " | 104.5–106.5 [IPA—AcOEt] |
| 136*³ | " | " | " | " | piperidine (HN) | " | " | 220–221 [EtOH—AcOEt] |
| 137*³ | BzO–C₆H₄– | H | H | H | imidazole (NH) | 1 | — | 154–156 [IPA—AcOEt] |
| 138*⁴ | phenyl | " | " | " | piperazine (HN, NH) | " | 2HCl | 241–242 (decomp). |
| 139 | PhO–C₆H₄– (meta) | " | " | " | pyridyl | " | — | 53.5–54.5 [Et₂O] |
| 140 | phenyl | " | " | " | " | 3 | " | Oily |
| 141 | PhO–C₆H₄– | H | H | H | pyridyl | 1 | — | 84.5–85.5 [EtOH—IPE] |
| 142 | Me–C₆H₄– | " | " | " | " | " | " | 65.5–66.5 [EtOH—IPE] |
| 143 | F–C₆H₄– | " | " | " | " | " | " | 68–69 [EtOH—IPE] |

Note:
*¹: Optical rotation: +23.3° (25° C., C = 1, MeOH)
*²: Optical rotation: −22.5° (25° C., C = 1, MeOH)
*³: The reaction was effected using a trityl group as an amino-protecting group.
*⁴: The reaction was effected using a formyl group as an amino-protecting group.

PRODUCTION EXAMPLE 5

(1) A mixture of 4.30 g of 4-benzyl-2-hydroxymethylmorpholine, 930 mg of potassium tert-butoxide and 4 ml of dimethyl sulfoxide was heated to 80° C. Thereto was dropwise added 2.50 g of styrene oxide over 20 minutes. The resulting mixture was stirred for 2 hours at the same temperature. The reaction mixture was added to a mixture of 30 ml of diethyl ether and 30 ml of ice water. The organic layer was separated and mixed with 10 ml of water. The mixture was adjusted to pH 2.0 with 6N hydrochloric acid. The aqueous layer was separated and mixed with 30 ml of diethyl ether. The mixture was adjusted to pH 11 with a 2N aqueous sodium hydroxide solution. The organic layer was separated, washed with a saturated aqueous sodium chloride solution, and dried over anhydrous magnesium sulfate. The solvent was removed by distillation under reduced pressure. The residue was purified by column chromatography (eluant:toluene/ethyl acetate=1/1) to obtain 2.00 g of oily 1-phenyl-2-[(4-benzylmorpholin-2-yl)methoxy]ethanol (compound No. 144).

The compounds shown in Table 7 were obtained in the same manner.

In Table 7, $R^1$, $R^2$, $R^3$, $R^4$, $R^6$ and n each show a substituent or integer used in the following formula:

palladium-carbon and 10 ml of methanol was subjected to hydrogenation for 4 hours at room temperature under atmospheric pressure. After the completion of the reaction, palladium-carbon was removed by filtration. The solvent was removed by distillation under reduced pressure. The residue was purified by column chromatography (eluant:chloroform/methanol=10/1) to obtain 450 mg of an oily product. The oily product was dissolved in 2.5 ml of isopropanol. The solution was mixed with 220 mg of fumaric acid. The mixture was stirred for 1 hour at room temperature. The resulting crystals were collected by filtration, washed with 2 ml of isopropanol and dried to obtain 460 mg of ½ fumarate of 1-phenyl-2-[(morpholin-2-yl)methoxy]ethanol (compound No. 151).

Melting point: 146.5°–147° C. [EtOH]

The compounds shown in Table 8 were obtained in the same manner.

In Table 8, $R^1$, $R^2$, $R^3$, $R^4$, $R^6$ and n each show a substituent or integer used in the following formula:

TABLE 7

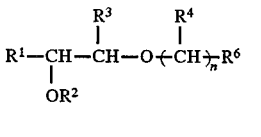

| Compound No. | $R^1$ | $R^2$ | $R^3$ | $R^4$ | $R^6$ | n | Addition salt | Melting point (°C.) |
|---|---|---|---|---|---|---|---|---|
| 145 | Me-C6H4- | H | H | H | O-morpholinyl-N-Bz | 1 | — | Oily |
| 146 | Cl-C6H4- | " | " | " | " | " | " | " |
| 147 | PhO-C6H4- | " | " | " | " | " | " | " |
| 148 | BzO-C6H4- | " | " | " | O-morpholinyl-N-Tr | " | " | " |
| 149 | MeO-C6H4- | H | H | H | O-morpholinyl-N-Tr | 1 | — | Oily |
| 150 | F-C6H4- | " | " | " | " | " | " | " |

(2) A mixture of 1.00 g of 1-phenyl-2-[(4-benzylmorpholin-2-yl)methoxy]ethanol, 500 mg of 5%

TABLE 8

$$R^1-\underset{\underset{OR^2}{|}}{CH}-\underset{\underset{}{|}}{\overset{\overset{R^3}{|}}{CH}}-O-(CH\underset{}{\overset{R^4}{|}})_n-R^6$$

| Compound No. | R¹ | R² | R³ | R⁴ | R⁶ | n | Addition salt | Melting point (°C.) |
|---|---|---|---|---|---|---|---|---|
| 152 | Me-C₆H₄- | H | H | H | morpholin-2-yl-O-CH₂ | 1 | ½ Fumaric acid | 155–156 [EtOH] |
| 153 | Cl-C₆H₄- | " | " | " | " | " | HCl | Amorphous |
| 154 | PhO-C₆H₄- | " | " | " | " | " | ½ Fumaric acid | 142–142.5 [EtOH—Me₂CO] |

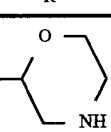

(3) 7 g of 1-(3-methoxyphenyl)-2-[(4-tritylmorpholin-2-yl)methoxy]ethanol was dissolved in 35 ml of acetone. To the solution was added 2.6 ml of a 5.9N dry hydrogen chloride-ethanol solution with ice cooling. The mixture was stirred for 2 hours at room temperature. After the completion of the reaction, the solvent was removed by distillation under reduced pressure. To the residue thus obtained were added 50 ml of water and 30 ml of ethyl acetate. The aqueous layer was separated and washed with ethyl acetate. Thereto was added 50 ml of chloroform. The resulting mixture was adjusted to pH 11 with a 1N aqueous sodium hydroxide solution. The organic layer was separated and dried over anhydrous magnesium sulfate. The solvent was removed by distillation under reduced pressure. The residue thus obtained was purified by column chromatography (eluant:chloroform/methanol=5/1) to obtain 1 g of an oily product. The oily product was dissolved in 3 ml of isopropanol. Thereto was added 430 mg of fumaric acid. The mixture was stirred for 1 hour at room temperature. The resulting crystals were collected by filtration and dried to obtain 800 mg of ½ fumarate of 1-(3-methoxyphenyl)-2-[(morpholin-2-yl)methoxy]ethanol (compound No. 155).

Melting point: 122°–123.5° C. [EtOH]

The compounds shown in Table 9 were obtained in the same manner.

In Table 9, R¹, R², R³, R⁴, R⁶ and n each show a substituent or integer used in the following formula:

TABLE 9

$$R^1-\underset{\underset{OR^2}{|}}{CH}-\underset{\underset{}{|}}{\overset{\overset{R^3}{|}}{CH}}-O-(CH\underset{}{\overset{R^4}{|}})_n-R^6$$

| Compound No. | R¹ | R² | R³ | R⁴ | R⁶ | n | Addition salt | Melting point (°C.) |
|---|---|---|---|---|---|---|---|---|
| 156 | BzO-C₆H₄- | H | H | H | morpholin-2-yl-O-CH₂ | 1 | ½ Fumaric acid | 147–148.5 [EtOH] |
| 157 | F-C₆H₄- | " | " | " | " | " | " | 126–127 [IPA] |

PRODUCTION EXAMPLE 6

(1) 5.1 g of potassium tert-butoxide was added to 105 ml of ethylene glycol mono-tert-butyl ether. The mixture was heated to 80° C. Thereto was dropwise added 35.0 g of 2-(3-chlorophenyl)oxirane over 1 hour. The mixture was stirred for 2 hours at the same temperature. The reaction mixture was added to a mixture of 100 ml of ice water and 100 ml of ethyl acetate. The organic layer was separated, washed with a saturated aqueous sodium chloride solution, and dried over anhydrous magnesium sulfate. The solvent was removed by distillation under reduced pressure. The residue thus obtained was subjected to further distillation under reduced pressure to obtain 37.7 g of colorless oily 1-(3-chlorophenyl)-2-(2-tert-butoxyethoxy)ethanol having a boiling point of 140°–146° C./0.9 mmHg.

(2) 37.0 g of 1-(3-chlorophenyl)-2-(2-tertbutoxyethoxy) ethanol was dissolved in 70 ml of methylene chloride. To the solution were added 12.9 g of pyridine and 16.6 g of acetic anhydride. The resulting mixture was stirred for 24 hours at room temperature. The reaction mixture was added to a mixture of 150 ml of ice water and 100 ml of methylene chloride. The resulting mixture was adjusted to pH 2 with 6N hydrochloric acid. The organic layer was separated, washed with a saturated aqueous sodium hydrogencarbonate solution and water in this order, and dried over anhydrous magnesium sulfate. The solvent was removed by distillation under reduced pressure to obtain 40.0 g of oily 1-acetoxy-1-(3-chlorophenyl)-2-(2-tertbutoxyethoxy)ethane.

(3) 40.0 g of 1-acetoxy-1-(3-chlorophenyl)-2-(2-tert-butoxyethoxy)ethane was dissolved in 40 ml of methylene chloride. To the solution was added 80 ml of trifluoroacetic acid with ice cooling. The mixture was stirred for 12 hours at room temperature. After the completion of the reaction, the solvent was removed by distillation under reduced pressure. The residue was mixed with 100 ml of toluene. The solvent was further removed by distillation under reduced pressure. The residue thus obtained was dissolved in a mixture of 90 ml of ethanol and 10 ml of water. To the solution was added 10.7 g of sodium hydrogencarbonate at room temperature. The mixture was adjusted to pH 6–7 with a saturated aqueous sodium hydrogencarbonate solution, and then concentrated to about a half volume under reduced pressure. To the concentrate was added 100 ml of ethyl acetate. The organic layer was separated. The aqueous layer was extracted with 50 ml of ethyl acetate. The extract was combined with the previously separated organic layer. The combined organic layer was washed with a saturated aqueous sodium chloride solution and dried over anhydrous magnesium sulfate. The solvent was removed by distillation under reduced pressure. The residue was purified by column chromatography (eluant:toluene/ethyl acetate=3/1) to obtain 19.4 g of oily 1-acetoxy-1-(3-chlorophenyl)-2-(2-hydroxyethoxy)ethane.

(4) To a mixture of 19.0 g of 1-acetoxy-1-(3-chlorophenyl)-2-(2-hydroxyethoxy)ethane and 95.0 ml of methylene chloride containing 9.1 ml of methanesulfonyl chloride was dropwise added 16.4 ml of triethylamine with ice cooling over 1 hour. The resulting mixture was stirred for 10 minutes at the same temperature and further for 1 hour at room temperature. The reaction mixture was added to a mixture of 50.0 ml of methylene chloride and 50.0 ml of ice water. The resulting mixture was adjusted to pH 2.0 with 6N hydrochloric acid. The organic layer was separated, washed with water and dried over anhydrous magnesium sulfate. The solvent was removed by distillation under reduced pressure to obtain 24.5 g of oily 1-acetoxy-1-(3-chlorophenyl)-2-(2-methanesulfonyloxyethoxy)ethane.

(5) 1.40 g of 1-acetoxy-1-(3-chlorophenyl)-2-(2-methanesulfonyloxyethoxy)ethane was dissolved in 7 ml of N,N-dimethylformamide. To the solution were added 0.69 ml of N-methylpiperazine and 1.03 g of potassium carbonate. The mixture was stirred for 3 hours at 80° C. The reaction mixture was cooled and added to a mixture of 30 ml of ice water and 30 ml of diethyl ether. The organic layer was separated. The aqueous layer was extracted with 20 ml of diethyl ether. The extract was combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was mixed with 7 ml of methanol and 45 mg of sodium methoxide. The mixture was allowed to stand overnight at room temperature. The solvent was removed by distillation under reduced pressure. To the residue thus obtained were added 20 ml of ethyl acetate and 10 ml of water. The organic layer was separated. The aqueous layer was extracted with 20 ml of ethyl acetate. The extract was combined with the previously separated organic layer. The combined organic layer was washed with a saturated aqueous sodium chloride solution and then purified by column chromatography (eluant:chloroform/methanol=10/1). To the resulting oily product were added 10 ml of ethanol and 1.2 ml of a 6N dry hydrogen chloride-ethanol solution in this order. To the resulting mixture was added 10 ml of diethyl ether. The mixture was stirred for 30 minutes. The resulting crystals were collected by filtration, washed with a mixture of 2 ml of ethanol and 2 ml of diethyl ether, and dried to obtain 770 mg of 1-(3-chlorophenyl)-2-[2-(4-methylpiperazin-1-yl) ethoxy]ethanol dihydrochloride (compound No. 158).

Melting point: 211°–213° C. [MeOH—EtOH]

The compounds shown in Table 10 were obtained in the same manner.

In Table 10, $R^1$, $R^2$, $R^3$, $R^4$, $R^6$ and n each show a substituent or integer used in the following formula:

TABLE 10

$$R^1-CH-CH-O-(CH_2)_n-R^6$$
$$\phantom{R^1-}| \phantom{CH-}| \phantom{CH-}$$
$$\phantom{R^1-}OR^2 \phantom{CH-} R^3 \phantom{CH-} R^4$$

| Compound No. | $R^1$ | $R^2$ | $R^3$ | $R^4$ | $R^6$ | n | Addition salt | Melting point (°C.) |
|---|---|---|---|---|---|---|---|---|
| 159 | 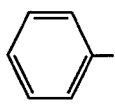 | H | H | H | 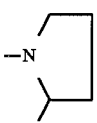 | 2 | — | Oily |

TABLE 10-continued $$R^1-\underset{\underset{OR^2}{|}}{CH}-\underset{\underset{}{|}}{\overset{R^3}{CH}}-O-(CH)_n^{\overset{R^4}{|}}R^6$$

| Compound No. | R¹ | R² | R³ | R⁴ | R⁶ | n | Addition salt | Melting point (°C.) |
|---|---|---|---|---|---|---|---|---|
| 160 | " | " | " | " | -N(Me)-C(=O)-[2-oxopyrrolidin-5-yl] | " | " | 134.5–136.5 [IPA] |
| 161 | " | " | " | " | indolizidinyl amide group | " | " | Oily |
| 162 | " | " | " | " | -N(3-hydroxypiperidin-1-yl) | " | HCl | 138–140 [IPA] |
| 163 | Ph | H | H | H | Me, -N(2,6-dimethylpiperidin-1-yl) | 2 | — | Oily |
| 164 | " | " | " | " | -N(4-Bz-piperidin-1-yl) | " | HCl | 164.5–166.5 |
| 165 | " | " | " | " | -N(1,2,3,4-tetrahydroisoquinolin-2-yl) | " | " | 169–171 [EtOH] |
| 166 | " | " | " | " | -N(4-methylpiperazin-1-yl) | " | 2HCl | 169–171 [CH₂Cl₂—EtOH] |
| 167 | " | " | " | " | -N(4-DPM-piperazin-1-yl) | " | — | 104.5–105.5 [EtOH] |
| 168 | Ph | H | H | H | -N(3,5-dimethylpiperidin-1-yl) | 2 | — | Oily |

TABLE 10-continued $$R^1-CH-CH-O+CH\}_n R^6$$
$$\phantom{R^1-CH-}|\phantom{CH-}|\phantom{O+CH\}_n }|$$
$$\phantom{R^1-}OR^2\phantom{-CH-O+CH\}_n R^6}R^3\phantom{ }R^4$$

| Compound No. | $R^1$ | $R^2$ | $R^3$ | $R^4$ | $R^6$ | n | Addition salt | Melting point (°C.) |
|---|---|---|---|---|---|---|---|---|
| 169*a | " | " | " | " | $-\overset{\oplus}{N}(Me)_3$ | " | 1/2 1,5-Naphtalene disulfonic acid | 208–210 [MeOH—Et₂O] |

Note: *a: 1 mole of a dimethylamino form was reacted with 0.5 mole of dimethyl 1,5-naphthalenedisulfonate, to obtain the desired product.

PRODUCTION EXAMPLE 7

A mixture of 2.0 g of 1-(4-benzyloxyphenyl)-2-[2-(N,N-dimethylamino)ethoxy]ethanol hydrochloride, 500 mg of 10% palladium-carbon and 10 ml of methanol was subjected to hydrogenation for 2 hours at room temperature under atmospheric pressure. After the completion of the reaction, palladium-carbon was removed by filtration. The solvent was removed by distillation under reduced pressure to obtain 1.4 g of 1-(4-hydroxyphenyl)-2-[2-(N,N-dimethylamino)ethoxy]ethanol hydrochloride (Compound No. 170).

Melting point: 169.5°–170.5° C. [EtOH]

The compounds shown in Table 11 were obtained in the same manner.

In Table 11, $R^1$, $R^2$, $R^3$, $R^4$, $R^6$ and n each show a substituent or integer used in the following formula:

TABLE 11

$$R^1-CH-CH-O+CH\}_n R^6$$
$$\phantom{R^1-}OR^2\phantom{-CH-O+CH\}_n R^6}R^3\phantom{ }R^4$$

| Compound No. | $R^1$ | $R^2$ | $R^3$ | $R^4$ | $R^6$ | n | Addition salt | Melting point (°C.) |
|---|---|---|---|---|---|---|---|---|
| 171 | 3-HO-C₆H₄– | H | H | H | –N(Me)₂ | 2 | HCl | 150–152 [EtOH] |
| 172 | " | Ac | " | " | " | " | " | Amorphous |
| 173 | 3,4-(HO)₂-C₆H₃– | H | " | " | " | " | — | Oily |
| 174 | C₆H₅– | " | " | " | –NHMe | " | HCl | 145–147 |
| 175 | C₆H₅– | H | H | H | –N(CH₂CH₂)₂NH (piperazinyl) | 2 | 2HCl | 204.5–206.5 [MeOH] |
| 176 | 3-Me-C₆H₄– | " | " | " | piperidinyl-NH | " | — | Oily |

TABLE 11-continued $$R^1-CH-CH-O(CH_2)_n-R^6$$
$$\phantom{R^1-CH-}|\phantom{CH-}|\phantom{O(CH_2)_n}|$$
$$\phantom{R^1-CH-}OR^2\phantom{-CH-O(CH_2)_n-R^6}$$

with $R^3$ and $R^4$ on the second and third carbons.

| Compound No. | $R^1$ | $R^2$ | $R^3$ | $R^4$ | $R^6$ | n | Addition salt | Melting point (°C.) |
|---|---|---|---|---|---|---|---|---|
| 177 | NH₂–(3-methylphenyl) | " | " | " | –N(Me)(Me) | " | HCl | 151–153 |

PRODUCTION EXAMPLE 8

0.65 ml of pyridine and 0.99 ml of acetic anhydride were added to 1 g of 1-(3-methylphenyl)-2-[2-(morpholin-4-yl) ethoxy]ethanol. The mixture was stirred for 3 hours at room temperature. The reaction mixture was subjected to distillation under reduced pressure to remove the solvent. To the residue were added 20 ml of ethyl acetate and 10 ml of water. The mixture was adjusted to pH 10 with potassium carbonate. The organic layer was separated, washed with water and a saturated aqueous sodium chloride solution in this order, and dried over anhydrous magnesium sulfate. The solvent was removed by distillation under reduced pressure. The residue was purified by column chromatography (eluant:chloroform/ethanol=30/1) to obtain 1 g of oily 1-acetoxy-1-(3-methylphenyl)-2-[2-(morpholin-4-yl) ethoxy]ethane (compound No. 178).

The compounds shown in Table 12 were obtained in the same manner.

In Table 12, $R^1$, $R^2$, $R^3$, $R^4$, $R^6$ and n each show a substituent or integer used in the following formula:

TABLE 12

$$R^1-CH-CH-O(CH_2)_n-R^6$$
$$\phantom{R^1-CH-}|\phantom{CH-}|\phantom{O(CH_2)_n}|$$
$$\phantom{R^1-CH-}OR^2$$

with $R^3$ and $R^4$ substituents.

| Compound No. | $R^1$ | $R^2$ | $R^3$ | $R^4$ | $R^6$ | n | Addition salt | Melting point (°C.) |
|---|---|---|---|---|---|---|---|---|
| 179 | Me–(3-methylphenyl) | Ac | H | H | pyrrolidin-2-one-1-yl | 2 | — | Oily |
| 180 | " | " | " | " | –N(Me)(Me) | " | " | " |
| 181*d | phenyl | H | " | " | –N(Me)(Ac) | " | " | " |
| 182*e | PhSO₂NH–(3-phenyl) | " | " | " | –N(Me)(Me) | " | HCl | 174.5–176.5 [EtOH] |

TABLE 12-continued $$R^1-\underset{\underset{OR^2}{|}}{CH}-\underset{\underset{}{|}}{\overset{\overset{R^3}{|}}{CH}}-O+CH\underset{\overline{n}}{\overset{\overset{R^4}{|}}{)}R^6$$

| Compound No. | R¹ | R² | R³ | R⁴ | R⁶ | n | Addition salt | Melting point (°C.) |
|---|---|---|---|---|---|---|---|---|
| 183 | BzO-〔phenyl〕- | Ac | H | H | -N(Me)(Me) | 2 | HCl | 169.5–170.5 [EtOH] |
| 184 | BzO-〔phenyl〕- | " | " | " | " | " | " | 131.5–132.5 [Me₂CO] |
| 185 | AcO-〔phenyl〕-AcO | " | " | " | " | " | " | Oily |
| 186 | PhO-〔phenyl〕- | " | " | " | " | " | — | Oily |
| 187 | Ph-〔phenyl〕- | " | " | " | " | " | " | 144.5–146.5 [EtOH—Et₂O] |
| 188 | 〔phenyl〕- | Ac | H | H | 〔pyridyl〕 | 1 | HCl | Oily |

Note:
*ᵈ: The indicated compound was obtained by reacting compound No. 174 with acetic anhydride.
*ᵉ: The indicated compound was obtained by reacting compound No. 177 with benzenesulfonyl chloride in pyridine.

PRODUCTION EXAMPLE 9

50 ml of a 1:1 mixture of chloroform and water was added to 3.30 g of 1-acetoxy-1-(3-hydroxyphenyl)-2-[2-(N,N-dimethylamino)ethoxy]ethane hydrochloride. To the mixture was added 750 mg of sodium carbonate with ice cooling. The organic layer was separated and dried with anhydrous magnesium sulfate. The solvent was removed by distillation under reduced pressure. The residue was mixed with 20 ml of benzene. The mixture was heated to 60° C. To the resulting solution was dropwise added a solution of 870 mg of ethyl isocyanate dissolved in 5 ml of benzene in 10 minutes. The mixture was stirred for 40 minutes at the same temperature. After the completion of the reaction, the solvent was removed by distillation under reduced pressure. The residue thus obtained was purified by column chromatography (eluant:chloroform/ethanol=10/1) to obtain an oily product. The oily product was dissolved in 10 ml of ethanol. Hydrogen chloride gas was blown into the solution. The solvent was removed by distillation under reduced pressure to obtain 1.90 g of 1-acetoxy-1-[3-(N-ethylcarbamoyloxy)phenyl]-2-[2-(N,N-dimethylamino)ethoxy]ethane hydrochloride (compound No. 189).

Melting point: 111.5°–113.5° C. [Me₂CO]

In the same manner, there was obtained oily 1-acetoxy-1-[3-(3-chlorophenylcarbamoyloxy)phenyl]-2-[2-(N,N-dimethylamino)ethoxy]ethane hydrochloride (compound No. 190).

PRODUCTION EXAMPLE 10

(1) 9.5 g of potassium tert-butoxide was added to 92 ml of ethylene glycol. The mixture was heated to 80° C. Thereto was dropwise added, in 3 hours, a solution of 34.7 g of 2-(4-benzyloxyphenyl)oxirane dissolved in 220 ml of dimethyl sulfoxide. The resulting mixture was stirred for 30 minutes at the same temperature. The reaction mixture was cooled and added to a mixture of 1 liter of ice water and 600 ml of ethyl acetate. The resulting mixture was adjusted to pH 7 with 6N hydrochloric acid. The organic layer was separated. The aqueous layer was extracted with 200 ml of ethyl acetate. The extract was combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was purified by column chromatography (eluant:chloroform/ethanol=10/1) to obtain 25 g of 1-(4-benzyloxyphenyl)-2-(2-hydroxyethoxy)ethanol.

Melting point: 116.5°–117° C. [MeCN]

(2) 22.7 g of 1-(4-benzyloxyphenyl)-2-(2-hydroxyethoxy) ethanol was dissolved in 140 ml of pyridine. The solution was cooled to −20° C. To the solution was added 19 g of p-toluenesulfonyl chloride. The resulting mixture was heated to 0° C. and stirred for 15 hours at the same temperature. The reaction mixture was added to a mixture of 300 ml of ice water and 200 ml of diethyl ether. The resulting mixture was adjusted to pH 2 with 6N hydrochloric acid. The organic layer was separated. The aqueous layer was extracted with 100 ml of diethyl ether. The extract was combined with the previously separated organic layer. The combined organic layer was washed with 1N hydrochloric acid, water and a saturated aqueous sodium chloride solution in this order, and dried over anhydrous magnesium sulfate. The solvent was removed by distillation under reduced pressure. The residue was purified by column chromatography (eluant:toluene/ethyl acetate=3/1) to obtain 20.5 g of oily 1-(4-benzyloxyphenyl)-2-[2-(p-toluenesulfonyl) oxyethoxy]ethanol.

(3) To a mixture of 20 g of 1-(4-benzyloxyphenyl)-2-[2-(p-toluenesulfonyloxy)ethoxy]ethanol and 40 ml of methylene chloride containing 8.2 g of 3,4-dihydro-2H-pyrane was added 2.3 g of pyridinium p-toluenesulfonate at room temperature. The resulting mixture was refluxed for 30 minutes. The reaction mixture was cooled and added to a mixture of 100 ml of ice water and 100 ml of methylene chloride. The organic layer was separated, washed with water, and dried over anhydrous magnesium sulfate. The solvent was removed by distillation under reduced pressure to obtain 18.6 g of light yellow oily 1-(4-benzyloxyphenyl)-1-(2-tetrahydropyranyloxy)-2-[2-(p-toluenesulfonyloxy)ethoxy] ethane.

(4) A mixture of 2 g of 1-(4-benzyloxyphenyl)-1-(2-tetrahydropyranyloxy)-2-[2-(p-toluenesulfonyloxy)ethoxy] ethane, 5.9 ml of a 40% aqueous methylamine solution and 20 ml of ethanol was refluxed for 2 hours. The reaction mixture was cooled and added to a mixture of 50 ml of ice water and 50 ml of diethyl ether. The organic layer was separated. The aqueous layer was extracted twice each with 20 ml of diethyl ether. The extracts were combined with the previously separated organic layer. The combined organic layer was mixed with 10 ml of water. The mixture was adjusted to pH 1.0 with 6N hydrochloric acid. The aqueous layer was separated and stirred for 30 minutes at room temperature. Thereto was added 30 ml of chloroform. The resulting mixture was adjusted to pH 12 with a 5% aqueous sodium hydroxide solution. The organic layer was separated, washed with water and a saturated aqueous sodium chloride solution in this order, and dried over anhydrous magnesium sulfate. The solvent was removed by distillation under reduced pressure. The residue was mixed with 10 ml of acetone. Hydrogen chloride gas was blown into the mixture with ice cooling. The resulting crystals were collected by filtration, washed with acetone, and dried to obtain 620 mg of 1-(4-benzyloxyphenyl)-2-(2-methylaminoethoxy)ethanol hydrochloride (compound No. 191).

Melting point: 173°–173.5° C. [EtOH]

The compounds shown in Table 13 were obtained in the same manner.

In Table 13, $R^1$, $R^2$, $R^3$, $R^{4a}$, $R^{4b}$, $R^6$, na and nb each show a substituent or integer used in the following formula:

TABLE 13

$$R^1-CH-CH-O+CH)_{na}+CH)_{nb}-R^6$$
with $OR^2$, $R^3$, $R^{4a}$, $R^{4b}$ substituents

| Compound No. | $R^1$ | $R^2$ | $R^3$ | $R^{4a}$ | $R^{4b}$ | $R^6$ | na | nb | Addition salt | Melting point (°C.) |
|---|---|---|---|---|---|---|---|---|---|---|
| 192 | PhO—C₆H₄— | H | H | H | H | —NMeH | 1 | 1 | HCl | 158–158.5 [IPA] |
| 193 | " | " | " | " | " | —N-i-Pr H | " | " | " | 170–170.5 [EtOH] |
| 194 | benzodioxole | " | " | " | " | —NMe₂ | " | " | " | 180–181 [EtOH—AcOEt] |
| 195 | BzO—C₆H₄— | " | " | " | " | —N(piperazinyl)NMe | " | " | 2HCl | 178–180.5 [MeCN—Et₂O] |
| 196 | BzO—C₆H₄— | H | H | H | H | —N-i-Pr H | 1 | 1 | HCl | 174.5–175 [IPA] |
| 197 | " | " | " | " | " | —N(piperazinyl)N-CH=CH-C₆H₅ | " | " | 2HCl | 212.5–213 [MeOH] |

TABLE 13-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 198 | " | " | " | " | " | −N(CH₂CH₂OH)₂ | " | " | — | Oily |
| 199 | " | " | " | " | " | −N(piperazinyl)-CH₂CH₂OH | " | " | 2HCl | 158.5–160.5 [EtOH] |
| 200 | " | " | " | " | " | −N(pyrrolidinyl-3-NH₂) | " | " | — | 55–58 |
| 201 | BzO-C₆H₄- | H | H | H | H | −N(Me)CH₂CH₂OH | 1 | 1 | — | 36–38 |
| 202 | " | " | " | " | " | −N(Me)(Et) | " | " | " | Oily |
| 203 | " | " | " | " | " | −N(Me)(cyclopropyl) | " | " | HCl | 139–141 [IPA—AcOEt] |
| 204 | " | " | " | " | " | −NH(cyclopropyl) | " | " | " | 163–164 [EtOH—MeCN] |
| 205 | " | " | " | " | " | −N(Me)−CH₂COOMe | " | " | — | Oily |
| 206 | 3-Me-C₆H₄- | H | H | H | H | −N=N−N=C(Me) (triazole) | 1 | 1 | — | Oily |
| 207 | " | " | " | " | " | −N(pyrazolyl) | " | " | " | " |
| 208 | " | " | " | " | " | −NH(cyclopropyl) | " | " | HCl | 148.5–149.5 [IPA—AcOEt] |
| 209 | C₆H₅- | " | " | " | " | " | " | " | " | 173.5–175.5 [EtOH—Me₂CO] |
| 210 | " | " | " | " | " | −NH(adamantyl) | " | " | PTS | 198–200 [EtOH—AcOEt] |

TABLE 13-continued $$R^1-\underset{\underset{OR^2}{|}}{CH}-\underset{\underset{R^{4a}}{|}}{\overset{\overset{R^3}{|}}{CH}}-O-(CH)_{na}-(\overset{\overset{R^{4b}}{|}}{CH})_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 211 |  | H | H | H | H | —N-t-Bu H | 1 | 1 | HCl | 161–162.5 [IPA—AcOEt] |
| 212*1 | 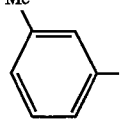 | Me | " | " | " | —N(Me)(Me) | " | " | " | Oily |
| 213*1 | 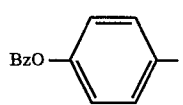 | " | " | " | " | " | " | " | — | " |

Note:
*¹: Methoxylation was effected using diazomethane-boron trifluoride in place of using 3,4-dihydro-2H-pyran, to obtain the desired product.

PRODUCTION EXAMPLE 11

A mixture of 500 mg of 2-[(imidazol-4-yl)methoxy]-1-phenylethanol, 1.1 ml of pyridine, 1.1 ml of triethylamine and 1.1 ml of acetic anhydride was stirred for 1 hour at 100° C. The reaction mixture was cooled to room temperature. The solvent was removed by distillation under reduced pressure. To the residue were added 1.1 ml of methyl iodide and 5 ml of acetonitrile. The mixture was allowed to stand at room temperature for 24 hours. The solvent was removed by distillation under reduced pressure. To the residue thus obtained were added 4 ml of ethanol and 6.8 ml of a 5% aqueous sodium hydroxide solution. The resulting mixture was stirred at room temperature for 6 hour. The solvent was removed by distillation under reduced pressure. To the residue thus obtained were added 30 ml of chloroform and 20 ml of water. The organic layer was separated, washed with water, and dried over anhydrous magnesium sulfate. The solvent was removed by distillation under reduced pressure. The resulting oily product was purified by column chromatography (eluant:chloroform/ethanol=10/1). Diisopropyl ether was added to the resulting white crystals, and the resulting mixture was filtered to obtain 450 mg of 2-[(1-methylimidazol-5-yl)methoxy]-1-phenylethanol (compound No. 214).

Melting point: 102°–105° C.

The following compound was obtained in the same manner.

1-(4-Benzyloxyphenyl)-2-[(1-methylimidazol-5-yl)methoxy]ethanol (compound No. 215)

Melting point: 148.5°–150.5° C. [IPA—AcOEt]

PRODUCTION EXAMPLE 12

1.23 g of N,N'-dicyclohexylcarbodiimide was added, with ice cooling, to a solution of 1.08 g of 2-(2-aminoethoxy)-1-phenylethanol, 730 mg of nicotinic acid, 810 mg of 1-hydroxybenzotriazole and 0.83 ml of triethylamine dissolved in 5 ml of tetrahydrofuran. The resulting mixture was stirred at the same temperature for 5 minutes and further at room temperature for 1 hour. To the reaction mixture was added 11 ml of ethyl acetate. The insolubles were removed by filtration. To the filtrate was added 5 ml of water and the mixture was adjusted to pH 2 with 6N hydrochloric acid. The aqueous layer was separated. The organic layer was extracted with 5 ml of water. The extract was combined with the previously separated aqueous layer. The combined aqueous layer was mixed with 20 ml of chloroform and adjusted to pH 10 with potassium carbonate. The organic layer was separated, washed with water, and dried over anhydrous magnesium sulfate. The solvent was removed by distillation under reduced pressure. The residue thus obtained was purified by column chromatography (eluant:chloroform/ethanol=15/1) to obtain 400 mg of oily 2-(2-nicotinoylaminoethoxy)-1-phenylethanol (compound No. 216).

IR (neat) cm$^{-1}$: $v_{C=O}$ 1635

PRODUCTION EXAMPLE 13

(1) 5 g of (S)-4-benzyl-2-acetoxymethylmorpholine was dissolved in 10 ml of ethanol. To the solution was added a solution of 1 g of sodium hydroxide dissolved in 5 ml of water with ice cooling. The mixture was stirred at room temperature for 10 minutes. The reaction mixture was added to 50 ml of ice water and extracted with 50 ml of chloroform. The organic layer was washed with water and a saturated aqueous sodium chloride solution in this order, and dried over anhydrous magnesium sulfate. The solvent was removed by distillation under reduced pressure. The residue thus obtained was purified by column chromatography (eluant:chloroform/ethanol=30/1) to obtain 3.6 g of oily (S)-4-benzyl-2-hydroxymethylmorpholine.

(2) 3.5 g of (S)-4-benzyl-2-hydroxymethylmorpholine was dissolved in 5 ml of ethanol. To the solution was added 5 ml of a 5.9N dry hydrogen chloride-ethanol solution with ice cooling. The resulting mixture was stirred for 10 minutes at the same temperature. Thereto was added a mixture of 500 mg of 5% palladium-carbon and 10 ml of methanol. The resulting mixture was subjected to hydrogenation for 3 hours at 40° C. After the completion of the reaction, palladium-carbon was removed by filtration. The solvent was removed by distillation under reduced pressure to obtain a yellow oily product. To the oily product were added 20 ml of dry methylene chloride and 4.7 ml of triethylamine. The resulting mixture was stirred at room temperature for 30 minutes. Thereto was dropwise added a solution of 4.7 g of trityl chloride dissolved in 10 ml of methylene chloride in 20 minutes, with ice cooling. The mixture was stirred at room temperature for 3 hours and added to 50 ml of ice water. The organic layer was separated and 20 ml of water was added thereto. The resulting mixture was adjusted to pH 12 with a 1N aqueous sodium hydroxide solution. The organic layer was separated and dried over anhydrous magnesium sulfate. The solvent was removed by distillation under reduced pressure to obtain a yellow oily product. The oily product was mixed with 10 ml of diisopropyl ether. The resulting crystals were collected by filtration to obtain 2.7 g of (S)-4-trityl-2-hydroxymethylmorpholine.

Melting point: 142.0°–142.5° C. [AcOEt—IPE]

Optical rotation: $[\alpha]_D^{27}=-10.9°$ (C=1, CHCl$_3$)

The (2R)-form having the following properties was obtained in the same manner.

Melting point: 142.0°–142.5° C. [AcOEt—IPE]

Optical rotation: $[\alpha]_D^{27}=+10.9°$ (C=1, CHCl$_3$)

(3) The same procedure as in (1) of Production Example 5 was repeated, except that the styrene oxide and the 4-benzyl-2-hydroxymethylmorpholine were replaced by (S)-2-phenyloxirane and (S)-4-trityl-2-hydroxymethylmorpholine, respectively, to obtain oily (1S, 2'S)-1-phenyl-2-[(4-tritylmorpholin-2-yl)methoxy]ethanol (compound No. 217).

(4) In 20 ml of acetone was dissolved (1S,2'S)-1-phenyl-2-[(4-tritylmorpholin-2-yl)methoxy]ethanol. To the solution was added, with ice cooling, 7 ml of a 5.9N dry hydrogen chloride-ethanol solution. The resulting mixture was stirred for 30 minutes at room temperature to effect a reaction. After the completion of the reaction, the solvent was removed by distillation under reduced pressure. The residue thus obtained was added to a mixture of 30 ml of ice water and 30 ml of ethyl acetate. The aqueous layer was separated and washed with 30 ml of ethyl acetate, after which 50 ml of chloroform was added thereto. The resulting mixture was adjusted to pH 11 with a 2N aqueous sodium hydroxide solution. The organic layer was separated, washed with a saturated aqueous sodium chloride solution, and dried over anhydrous magnesium sulfate. The solvent was removed by distillation under reduced pressure to obtain 1.9 g of a yellow oily product. The oily product was dissolved in 10 ml of ethanol. To the solution was added 720 mg of oxalic acid. The resulting mixture was heated to obtain a solution. The solution was allowed to stand overnight at room temperature. The resulting crystals were collected by filtration and dried to obtain 1.8 g of (1S,2'S)-1-phenyl-2-[(morpholin-2-yl)methoxy]ethanol oxalate (compound No. 218).

Melting point: 130°–132° C. [EtOH]

Optical rotation: $[\alpha]_D^{24}=+19.9°$ (C=1, CHCl$_3$)

The following compounds were obtained in the same manner.

(1R,2'S)-1-phenyl-2-[(morpholin-2-yl)methoxy]ethanol maleate (compound No. 219)

Melting point: 136°–136.5° C. [EtOH]

Optical rotation: $[\alpha]_D^{25}=-21.7°$ (C=1, CH$_3$OH)

(1S,2'R)-1-phenyl-2-[(morpholin-2-yl)methoxy]ethanol maleate (compound No. 220)

Melting point: 136°–136.5° C. [EtOH]

Optical rotation: $[\alpha]_D^{25}=+22.2°$ (C=1, CH$_3$OH)

(1R,2'R)-1-phenyl-2-[(morpholin-2-yl)methoxy]ethanol oxalate (compound No. 221)

Melting point: 131°–132.5° C. [EtOH]

Optical rotation: $[\alpha]_D^{25}=-20.4°$ (C=1, CH$_3$OH)

PRODUCTION EXAMPLE 14

(1) 1.19 g of 4-benzylthiobenzaldehyde was dissolved in 20 ml of tetrahydrofuran. The solution was cooled to −10° C. Thereto was dropwise added 10 ml of a tetrahydrofuran solution containing 2M of 2-chloroethoxymethylmagnesium chloride in 10 minutes. The resulting mixture was stirred for 1 hour with ice cooling. The reaction mixture was added to a mixture of 50 ml of ice water, 50 ml of ethyl acetate and 1 g of ammonium chloride. The resulting mixture was adjusted to pH 2 with 6N hydrochloric acid. The organic layer was separated, washed with water and a saturated aqueous sodium chloride solution in this order, and dried over anhydrous magnesium sulfate. The solvent was removed by distillation under reduced pressure. The residue thus obtained was purified by column chromatography [eluant:toluene/ethyl acetate=20/1] to obtain 1.34 g of 1-(4-benzylthiophenyl)-2-(2-chloroethoxy)ethanol.

Melting point: 49.5°–50.5° C. [hexane-IPE]

(2) A mixture of 600 mg of 1-(4-benzylthiophenyl)-2-(2-chloroethoxy)ethanol, 4 ml of a 50% aqueous dimethylamine solution, 310 mg of potassium iodide and 5 ml of ethanol was refluxed for 4 hours. To the reaction mixture was further added 4 ml of a 50% aqueous dimethylamine solution. The resulting mixture was refluxed for 4 hours. The reaction mixture was cooled to room temperature. The solvent was removed by distillation under reduced pressure. To the residue thus obtained were added 30 ml of ethyl acetate and 30 ml of water. The resulting mixture was adjusted to pH 10.5 with potassium carbonate. The organic layer was separated, washed with water and a saturated aqueous sodium chloride solution in this order, and dried over anhydrous magnesium sulfate. The solvent was removed by distillation under reduced pressure. The residue was dissolved in 15 ml of acetone. To the solution was added 0.4 ml of a 5N dry hydrogen chloride-ethanol solution. The resulting crystals were collected by filtration to obtain 590 mg of 1-(4-benzylthiophenyl)-2-[2-(N,N-dimethylamino)ethoxy]ethanol hydrochloride (compound No. 222).

Melting point: 173.5°–174.5° C. [EtOH]

The compounds shown in Table 14 were obtained in the same manner.

In Table 14, $R^1$, $R^2$, $R^3$, $R^{4a}$, $R^{4b}$, $R^6$, na and nb each show a substituent or integer used in the following formula:

TABLE 14

$$R^1-\underset{\underset{OR^2}{|}}{CH}-\underset{\underset{}{|}}{\overset{\overset{R^3}{|}}{CH}}-O-(CH)_{na}-(CH)_{nb}-R^6$$
(with $R^{4a}$ on the first CH in parens and $R^{4b}$ on the second)

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 223 | Bz—S(=O)(=O)—C₆H₄— | H | H | H | H | —N(Me)(Me) | 1 | 1 | HCl | 194–195 [EtOH] |
| 224 | (thiophen-2-yl)-C₆H₄— | " | " | " | " | " | " | " | " | 207–208 [EtOH—AcOEt] |
| 225 | (pyridin-2-yl)-C₆H₄— | " | " | " | " | " | " | " | Maleic acid | 168–170 (decomp.) |
| 226 | Et—C₆H₄— (ortho-Et phenyl) | " | " | " | " | " | " | " | HCl | 159.5–160.5 [EtOH—AcOEt] |
| 227 | CH₂=CH—C₆H₄— | " | " | " | " | " | " | " | " | 141–142 [EtOH—AcOEt] |

PRODUCTION EXAMPLE 15

A mixture of 13.2 g of potassium tert-butoxide and 47.2 ml of 2-(N,N-dimethylamino)ethanol was heated to 80° C. Thereto was dropwise added 40.0 g of 2-(1-naphthyl) oxirane in 3.5 hours. The resulting mixture was stirred for 1.5 hours at 80°–85° C. The reaction mixture was cooled and added to a mixture of 100 ml of ethyl acetate and 100 ml of ice water. The resulting mixture was adjusted to pH 11.5 with 6N hydrochloric acid. The organic layer was separated. The aqueous layer was extracted with 50 ml of ethyl acetate. The extract was combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was subjected to distillation to obtain a fraction having a boiling point of 152°–163° C./0.6–0.8 mmHg. The oily product obtained was dissolved in 200 ml of acetone. Into the solution was blown hydrogen chloride gas with ice cooling. The resulting crystals were collected by filtration, washed with acetone, and dried to obtain 22.7 g of 2-[2-(N,N-dimethylamino)ethoxy]-1-(1-naphthyl)ethanol hydrochloride (compound No. 228).

Melting point: 196°–197° C. [EtOH]

The compounds shown in Table 15 were obtained in the same manner.

In Table 15, $R^1$, $R^2$, $R^3$, $R^{4a}$, $R^{4b}$, $R^6$, na and nb each show a substituent or integer used in the following formula:

TABLE 15
| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 229 |  | H | H | H | H | 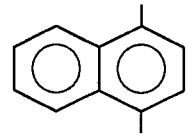 | 1 | 1 | HCl | 193–194 [EtOH] |
| 230 | 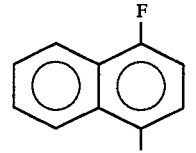 | " | " | " | " | " | " | " | " | 149–150 [Me₂CO—EtOH] |
| 231 | 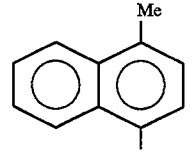 | " | " | " | " | " | " | " | " | 178–179 [Me₂CO—EtOH] |
| 232 | 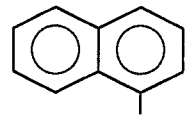 | " | " | " | " | " | " | " | " | 184–185 [Me₂CO—EtOH] |
| 233* | 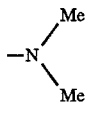 | H | H | H | H | 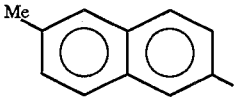 | 2 | 1 | — | Oily |
| 234* | " | " | " | " | " | " | " | 2 | " | " |
| 235 | 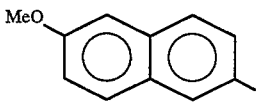 | " | " | " | " | " | 1 | 1 | HCl | 213–214 [IPA] |
| 236 | 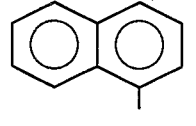 | " | " | " | " | " | " | " | " | 205–205.5 [MeOH—EtOH] |
| 237 | 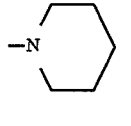 | " | " | " | " |  | " | " | " | 174–174.5 [EtOH—Et₂O] |
| 238 |  | H | H | H | H | 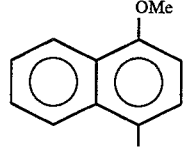 | 1 | 1 | HCl | 156.5–158 [EtOH—Et₂O] |
| 239 | 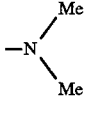 | " | " | " | " | 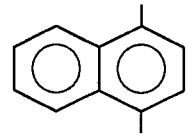 | " | " | " | 157–158 [IPA] |

TABLE 15-continued $$R^1-CH(OR^2)-CH(R^3)-O-(CH(R^{4a}))_{na}-(CH(R^{4b}))_{nb}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 240* | naphthalen-1-yl | " | " | " | " | -N(pyrrolidinone) | 1 | 1 | — | Oily |
| 241* | " | " | " | " | " | -N(Bz)(Me) | " | " | " | " |
| 242* | " | " | " | " | " | -N(pyrrolidinyl-C(O)-N-pyrrolidinyl) | " | " | " | " |
| 243 | naphthalen-1-yl | H | H | H | H | -N(Et)₂ | 1 | 1 | HCl | 155.5–157 [IPA] |
| 244 | 6-Me-naphthalen-1-yl | " | " | " | " | -N(Me)₂ | " | " | " | 151.5–153.5 [IPA] |
| 245 | 6-Cl-naphthalen-2-yl | " | " | " | " | " | " | " | " | 193.5–196.5 [EtOH] |
| 246 | 7-Cl-naphthalen-1-yl | " | " | " | " | " | " | " | " | 166.5–168 [IPA] |
| 247 | 8-Cl-naphthalen-1-yl | " | " | " | " | " | " | " | " | 161–163 [EtOH] |
| 248 | 6-Me-naphthalen-2-yl | H | H | H | H | -N(Et)₂ | 1 | 1 | HCl | 100.5–101.5 [IPA—AcOEt] |
| 249 | naphthalen-1-yl | " | Me | " | " | -N(Me)₂ | " | " | " | 186.5–188 [EtOH—Me₂CO] |
| 250 | " | " | H | Me | " | " | " | " | Fumaric acid | 197–198.5 [EtOH—AcOEt] |

TABLE 15-continued $$R^1-\underset{\underset{OR^2}{|}}{CH}-\underset{\underset{}{|}}{\overset{\overset{R^3}{|}}{CH}}-O\underset{}{(CH)_{na}}\underset{\underset{R^{4a}}{|}}{\overset{\overset{R^{4b}}{|}}{(CH)_{nb}}}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 251 | 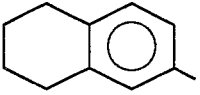 | " | " | H | " | " | " | " | HCl | 199.5–201 [IPA—AcOEt] |
| 252 | 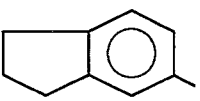 | " | " | " | " | " | " | " | " | 198–199.5 [IPA] |
| 253 | EtO 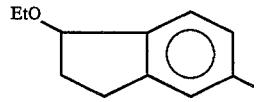 | H | H | H | H | 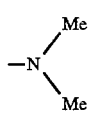 | 1 | 1 | HCl | 157–159 [IPA] |

Note:
*: These compounds were not subjected to a step of converting into a hydrochloride.

PRODUCTION EXAMPLE 16

(1) A mixture of 6.0 g of 2-hydroxymethyl-4-tritylmorpholine, 1.0 g of potassium tert-butoxide and 6 ml of dimethyl sulfoxide was heated to 80° C. Thereto was dropwise added, at 80°–85° C. in 2 hours, a solution of 2.8 g of 2-(2-naphthyl)oxirane dissolved in 6 ml of dimethyl sulfoxide. The resulting mixture was stirred at the same temperature for 3 hours. The reaction mixture was cooled and added to a mixture of 60 ml of ice water and 60 ml of ethyl acetate. The organic layer was separated, washed with water and a saturated aqueous sodium chloride solution in this order, and dried over anhydrous magnesium sulfate. The solvent was removed by distillation under reduced pressure to obtain 9.0 g of oily 1-(2-naphthyl)-2-[(4-tritylmorpholin-2-yl)-methoxy]ethanol (compound No. 254).

In the same manner, there was obtained oily 1-(1-naphthyl)-2-[(4-tritylmorpholin-2-yl)methoxy]ethanol (compound No. 255).

(2) In 50 ml of acetone was dissolved 9.0 g of 1-(2-naphthyl)-2-[(4-tritylmorpholin-2-yl)methoxy]ethanol. To the solution was added 3.5 ml of a 5.9N dry hydrogen chloride-ethanol solution with ice cooling. The mixture was stirred for 2 hours at room temperature to effect reaction. After the completion of the reaction, the solvent was removed by distillation under reduced pressure. To the residue thus obtained were added 50 ml of water and 30 ml of ethyl acetate. The aqueous layer was separated and washed with 30 ml of ethyl acetate. Thereto was added 50 ml of ethyl acetate. The resulting mixture was adjusted to pH 10.5 with potassium carbonate. The organic layer was separated, washed with a saturated aqueous sodium chloride solution, and dried over anhydrous magnesium sulfate. The solvent was removed by distillation under reduced pressure. The residue thus obtained was purified by column chromatography (eluant:chloroform/methanol=5/1) to obtain 1.2 g of an oily product. The oily product was dissolved in 5 ml of isopropanol. To the solution was added 0.5 g of fumaric acid. The mixture was heated to obtain a solution. The solution was allowed to stand at room temperature overnight. The resulting crystals were collected by filtration to obtain 0.9 g of 1-(2-naphthyl)-2-[(morpholin-2-yl)methoxy]ethanol ½ fumarate (compound No. 256).

Melting point: 141°–144° C. [EtOH]

In the same manner, there was obtained amorphous 1-(1-naphthyl)-2-[(morpholin-2-yl)methoxy]ethanol hydrochloride (compound No. 257).

PRODUCTION EXAMPLE 17

(1) A mixture of 4.5 g of potassium tert-butoxide and 45 ml of ethylene glycol was heated to 80° C. Thereto was dropwise added 13.7 g of 2-(1-naphthyl)oxirane in 1 hour. The resulting mixture was stirred for 1 hour at the same temperature. The reaction mixture was cooled and added to a mixture of 50 ml of ethyl acetate and 50 ml of ice water. The organic layer was separated. The aqueous layer was extracted twice each with 20 ml of ethyl acetate. The extracts were combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was purified by column chromatography (eluant:toluene/ethyl acetate=⅓) to obtain 8.3 g of 2-(2-hydroxyethoxy)-1-(1-naphthyl)ethanol.

Melting point: 91°–92° C. [IPE]

In the same manner, there was obtained 2-(2-hydroxyethoxy)-1-(2-naphthyl)ethanol.

Melting point: 105°–106° C. [AcOEt]

(2) 8.3 g of 2-(2-hydroxyethoxy)-1-(1-naphthyl)ethanol was dissolved in 50 ml of pyridine. The solution was cooled to −25° C. Thereto was added 6.8 g of p-toluenesulfonyl chloride. The resulting mixture was allowed to stand at 0°–5° C. for 24 hours and further at room temperature for 4 hours. The reaction mixture was added to a mixture of 103 ml of 6N hydrochloric acid, 50 ml of ice water and 100 ml of diethyl ether. The resulting mixture was adjusted to pH 2.0 with 6N hydrochloric acid. The organic layer was separated. The aqueous layer was extracted with 20 ml of diethyl ether. The extract was combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was purified by column chromatography (eluant:toluene/ethyl acetate=10/1) to obtain 6.3 g of colorless, oily 1-(1-naphthyl)-2-[2-(p-toluenesulfonyloxy)ethoxy]ethanol.

In the same manner, there was obtained colorless, oily 1-(2-naphthyl)-2-[2-(p-toluenesulfonyloxy)ethoxy]ethanol.

(3) 0.82 g of pyridinium p-toluenesulfonate was added to a solution of 6.3 g of 1-(1-naphthyl)-2-[2-(p-toluenesulfonyloxy)ethoxy]ethanol and 2.97 ml of 3,4-dihydro-2H-pyran dissolved in 63 ml of methylene chloride at room temperature. The resulting mixture was stirred at the same temperature for 20 minutes and further at 35°–40° C. for 10 minutes. The reaction mixture was cooled, washed with water, and dried over anhydrous magnesium sulfate. The solvent was removed by distillation under reduced pressure. The residue thus obtained was purified by column chromatography (eluant:toluene/ethyl acetate=10/1) to obtain 7.53 g of colorless, oily 1-(1-naphthyl)-1-(tetrahydropyran-2-yloxy)-2-[2-(p-toluenesulfonyloxy)ethoxy]ethane.

In the same manner, there was obtained colorless, oily 1-(2-naphthyl)-1-(tetrahydropyran-2-yloxy)-2-[2-(p-toluenesulfonyloxy)ethoxy]ethane.

(4) A mixture of 7.5 g of 1-(1-naphthyl)-1-(tetrahydropyran-2-yloxy)-2-[2-(p-toluenesulfonyloxy)ethoxy]ethane, 2.65 ml of N-methylpiperazine, 3.96 g of potassium carbonate and 38 ml of N,N-dimethylformamide was stirred for 2 hours at 90°–100° C. The reaction mixture was cooled and added to a mixture of 100 ml of diethyl ether and 100 ml of ice water. The organic layer was separated. The aqueous layer was extracted twice each with 25 ml of diethyl ether. The extracts were combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was purified by column chromatography (eluant:chloroform/ethanol=10/1) to obtain 3.36 g of colorless, oily 2-[2-(4-methylpiperazin-1-yl)ethoxy]-1-(1-naphthyl)-1-(tetrahydropyran-2-yloxy)ethane (compound No. 258).

(5) In 30 ml of acetone was dissolved 3.3 g of 2-[2-(4-methylpiperazin-1-yl)ethoxy]-1-(1-naphthyl)-1-(tetrahydropyran-2-yloxy)ethane. To the solution were added 3.46 g of p-toluenesulfonic acid monohydrate and 7 ml of water at room temperature. The resulting mixture was stirred at the same temperature for 30 minutes and further at 40° C. for 1 hour. The reaction mixture was added to a mixture of 60 ml of chloroform and 60 ml of ice water. The mixture was adjusted to pH 11 with a 10% aqueous sodium hydroxide solution. The organic layer was separated. The aqueous layer was extracted with 20 ml of chloroform. The extract was combined with the previously separated organic layer. The combined organic layer was washed with water and dried over anhydrous magnesium sulfate. The solvent was removed by distillation under reduced pressure. The residue thus obtained was dissolved in 40 ml of acetone. Hydrogen chloride gas was blown into the solution with ice cooling. The resulting solution was stirred at room temperature for 30 minutes. Thereto was added 40 ml of diethyl ether. The resulting mixture was stirred at the same temperature for 30 minutes. The resulting crystals were collected by filtration, washed with acetone, and dried to obtain 2.35 g of 2-[2-(4-methylpiperazin-1-yl)ethoxy]-1-(1-naphthyl)ethanol dihydrochloride (compound No. 259).

Melting point: 230.5°–231.5° C. [MeOH]

PRODUCTION EXAMPLE 18

The same procedure as in (4) and (5) of Production Example 17 was repeated, except that the N-methylpiperazine was replaced by N-(p-fluorobenzoyl)piperidine, to obtain 2-{2-[4-(p-fluorobenzoyl)piperidin-1-yl]ethoxy}-1-(1-naphthyl)ethanol hydrochloride (compound No. 260).

Melting point: 204.5°–205.5° C. [MeOH]

PRODUCTION EXAMPLE 19

In 20 ml of ethanol was dissolved 2 g of 1-(1-naphthyl)-1-(tetrahydropyran-2-yloxy)-2-[2-(p-toluenesulfonyloxy)ethoxy]ethane. To the solution was added 6.60 g of a 40% aqueous methylamine solution at room temperature. The mixture was refluxed for 1 hour. The reaction mixture was cooled and added to a mixture of 20 ml of ice water and 50 ml of diethyl ether. The organic layer was separated. The aqueous layer was extracted with 20 ml of diethyl ether. The extract was combined with the previously separated organic layer. To the combined organic layer was added 15 ml of water and the resulting mixture was adjusted to pH 1.5 with 6N hydrochloric acid. The aqueous layer was separated. The organic layer was extracted twice each with 10 ml of water. The extracts were combined with the previously separated aqueous layer. The combined aqueous layer was mixed with 25 ml of chloroform and adjusted to pH 11 with a 10% aqueous sodium hydroxide solution. The organic layer was separated. The aqueous layer was extracted twice each with 10 ml of chloroform. The extracts were combined with the previously separated organic layer. The combined organic layer was dried over anhydrous magnesium sulfate. The solvent was removed by distillation under reduced pressure to obtain 1.27 g of an oily product. The oily product was dissolved in 10 ml of acetone. Into the solution was blown hydrogen chloride gas with ice cooling. Thereto was added 10 ml of diethyl ether. The resulting crystals were collected by filtration to obtain 0.72 g of 2-[2-(N-methylamino)ethoxy]-1-(1-naphthyl)ethanol hydrochloride (compound No. 261).

Melting point: 137.5°–139° C. [IPA]

The compounds shown in Table 16 were obtained in the same manner.

In Table 16, $R^1$, $R^2$, $R^3$, $R^{4a}$, $R^{4b}$, $R^6$, na and nb each show a substituent or integer used in the following formula:

TABLE 16

$$R^1-\underset{\underset{OR^2}{|}}{CH}-\underset{\underset{R^{4a}}{|}}{\overset{R^3}{CH}}-O+CH_2)_{\overline{na}}(\overset{R^{4b}}{\underset{|}{CH}})_{\overline{nb}}-R^6$$

| Compound No. | R¹ | R² | R³ | R⁴ᵃ | R⁴ᵇ | R⁶ | na | nb | Addition salt | Melting point (°C.) |
|---|---|---|---|---|---|---|---|---|---|---|
| 262 | 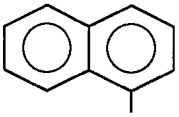 | H | H | H | H | 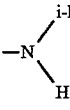 i-Pr | 1 | 1 | HCl | 180–181 [EtOH] |
| 263 | " | " | " | " | " | 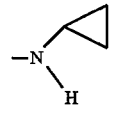 | " | " | — | 159.5–162 |
| 264 | " | " | " | " | " | 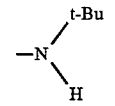 t-Bu | " | " | 1/2 Maleic acid | 184–185 [IPA-AcOEt] |
| 265 | 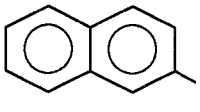 | H | H | H | H | 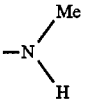 Me | " | " | HCl | 170–171 [EtOH] |
| 266 | " | " | " | " | " | 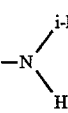 i-Pr | " | " | " | 180.5–181.5 [IPA-EtOH] |

PRODUCTION EXAMPLE 20

A mixture of 3.5 g of potassium tert-butoxide, 9.4 g of N-tritylethanolamine and 50 ml of dimethyl sulfoxide was heated to 85° C. Thereto was added 5.3 g of 2-(1-naphthyl) oxirane. The resulting mixture was stirred at the same temperature for 5 minutes. The reaction mixture was cooled and added to a mixture of 100 ml of ethyl acetate and 150 ml of ice water. The organic layer was separated. The aqueous layer was extracted with 50 ml of ethyl acetate. The extract was combined with the previously separated organic layer. The combined organic layer was washed with water and a saturated aqueous sodium chloride solution in this order, and dried over anhydrous magnesium sulfate. The solvent was removed by distillation under reduced pressure. To the residue thus obtained were added 80 ml of a 50% aqueous formic acid solution and 40 ml of tetrahydrofuran. The resulting mixture was stirred at 50°–60° C. for 1 hour. The reaction mixture was cooled. The solvent was removed by distillation under reduced pressure. To the residue thus obtained were added 60 ml of ethyl acetate and 60 ml of water. The resulting mixture was adjusted to pH 2 with 6N hydrochloric acid. The aqueous layer was separated. The organic layer was extracted twice each with 15 ml of water. The extracts were combined with the previously separated aqueous layer. To the combined aqueous layer was added 100 ml of chloroform and the resulting mixture was adjusted to pH 10.5 with potassium carbonate. The organic layer was separated, washed with water, and dried over anhydrous magnesium sulfate. The solvent was removed by distillation under reduced pressure. To the residue thus obtained was added 10 ml of diisopropyl ether. The resulting crystals were collected by filtration and dried to obtain 1.8 g of 2-(2-aminoethoxy)-1-(1-naphthyl)ethanol (compound No. 267).

Melting point: 89.5°–92° C. [CHCl₃—Et₂O]

PRODUCTION EXAMPLE 21

7 ml of water and 7 ml of dioxane were added to 0.7 g of 2-(2-aminoethoxy)-1-(1-naphthyl)ethanol to obtain a solution. To the solution was added 0.32 g of potassium carbonate. The resulting mixture was heated to 50° C. Thereto was added 0.35 g of 2-chloropyrimidine. The resulting mixture was refluxed for 3 hours. Thereto were added 0.32 g of potassium carbonate and 0.35 a of 2-chloropyrimidine. The resulting mixture was further refluxed for 2.5 hours. The reaction mixture was cooled and added to a mixture of 20 ml of ethyl acetate and 20 ml of ice water. The organic layer was separated. The aqueous layer was extracted with 10 ml of ethyl acetate. The extract was combined with the previously separated organic layer. To the combined organic layer was added 15 ml of water and the resulting mixture was adjusted to pH 1.5 with 6N hydrochloric acid. The aqueous layer was separated. The organic layer was extracted with 10 ml of water. The extract was combined with the previously separated aqueous layer. To the combined aqueous layer was added 50 ml of methylene chloride and the resulting mixture was adjusted to pH 10.5 with potassium carbonate. The organic layer was separated, washed with water, and dried over anhydrous magnesium sulfate. The solvent was removed by distillation under reduced pressure. The residue thus obtained was purified by column chromatography (eluant:chloroform/ethanol=20/1) to obtain an oily product. To the oily product were added 4 ml of ethanol and 0.21 g of maleic acid. The resulting mixture was stirred at room temperature for 1 hour. To the reaction mixture was added 2 ml of diethyl ether. The resulting mixture was stirred at the same temperature for 1 hour. The resulting crystals were collected by filtration and dried to obtain 0.53 g of 1-(1-naphthyl)-2-{2-[(pyrimidin-2-yl)amino]ethoxy}ethanol maleate (compound No. 268).

Melting point: 101.5°–103° C. [EtOH—AcOEt]

PRODUCTION EXAMPLE 22

0.62 g of N,N'-dicyclohexylcarbodiimide was added to a mixture of 0.7 g of 2-(2-aminoethoxy)-1-(1-naphthyl)ethanol, 0.37 g of nicotinic acid, 0.41 g of 1-hydroxybenzotriazole, 0.42 ml of triethylamine and 4 ml of tetrahydrofuran with ice cooling. The resulting mixture was stirred at the same temperature for 5 minutes and further at room temperature for 1 hour. To the reaction mixture was added 6 ml of ethyl acetate. The insolubles were removed by filtration. To the filtrate were added 15 ml of ethyl acetate and 20 ml of water. The resulting mixture was adjusted to pH 2 with 6N hydrochloric acid. The aqueous layer was separated. The organic layer was extracted twice each with 10 ml of water. The extracts were combined with the previously separated aqueous layer. To the combined aqueous layer was added 30 ml of chloroform and the resulting mixture was adjusted to pH 10.5 with potassium carbonate. The organic layer was separated, washed with water, and dried over anhydrous magnesium sulfate. The solvent was removed by distillation under reduced pressure. The residue thus obtained was purified by column chromatography (eluant:chloroform/ethanol=10/1) to obtain an oily product. The oily product was dissolved in 7 ml of acetone. To the solution was added 0.43 ml of a 5N dry hydrogen chloride-ethanol solution. The resulting mixture was stirred at room temperature for 1 hour. To the reaction mixture was added 3 ml of diethyl ether. The resulting mixture was stirred at the same temperature for 1 hour. The resulting crystals were collected by filtration and dried to obtain 0.67 g of 1-(1-naphthyl)-2-[2-(nicotinoylamino)ethoxy]ethanol hydrochloride (compound no. 269).

Melting point: 162.5°–163.5° C. [EtOH—AcOEt]

PRODUCTION EXAMPLE 23

The same procedure as in (1) of Production Example 16 was repeated, except that the 2-(2-naphthyl)oxirane and the 2-hydroxymethyl-4-tritylmorpholine were replaced by 2-(1-naphthyl)oxirane and 1,4-diformyl-2-piperazinyl methanol, respectively, to obtain oily 2-[(1,4-diformylpiperazin-2-yl)methoxy]-1-(1-naphthyl)ethanol (compound No. 270).

The compounds shown in Table 17 were obtained in the same manner.

In Table 17, $R^1$, $R^2$, $R^3$, $R^4$, $R^6$ and n each show a substituent or integer used in the following general formula:

TABLE 17

$$R^1-CH-CH-O-(CH_2)_n-R^6$$
$$\phantom{R^1-CH-}|\phantom{CH-O-}|\phantom{(CH_2)_n-}|$$
$$\phantom{R^1-CH}OR^2\phantom{CH-O-}R^3\phantom{(}R^4$$

| Compound No. | $R^1$ | $R^2$ | $R^3$ | $R^4$ | $R^6$ | n | Melting point (°C.) |
|---|---|---|---|---|---|---|---|
| 271 | 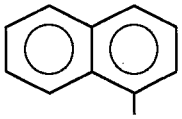 | H | H | H | 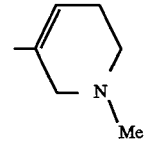 | 1 | 98–100 [AcOEt] |
| 272 | 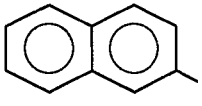 | " | " | " | 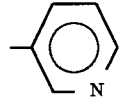 | " | 83–85 [AcOEt-IPE] |
| 273 | 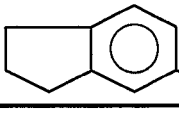 | " | " | " | " | " | 72–73.5 [AcOEt-IPE] |

PRODUCTION EXAMPLE 24

In 1.5 ml of methanol was dissolved 250 mg of 2-[(1,4-diformylpiperazin-2-yl)methoxy]-1-(1-naphthyl)ethanol. To the solution was added 1.5 ml of a 5N dry hydrogen chloride-ethanol solution. The mixture was allowed to stand at room temperature overnight. The resulting crystals were collected by filtration, washed with ethanol, and dried to obtain 180 mg of 1-(1-naphthyl)-2-[(piperazin-2-yl)methoxy]ethanol dihydrochloride (compound No. 274).

Melting point: 199°–201° C. (decomp.)

PRODUCTION EXAMPLE 25

The compound obtained in the same manner as in (1) of Production Example 16 was reacted with hydrogen chloride gas in the same manner as in the production of the hydrochloride of Production Example 22, to obtain the compounds shown in Table 18.

In Table 18, $R^1$, $R^2$, $R^3$, $R^4$, $R^6$ and n each show a substituent or integer used in the following general formula:

TABLE 18

$$R^1-\underset{OR^2}{\underset{|}{CH}}-\underset{R^4}{\underset{|}{CH}}-O(CH_2)_n R^6$$
       $R^3$

| Compound No. | $R^1$ | $R^2$ | $R^3$ | $R^4$ | $R^6$ | n | Addition salt | Melting point (°C.) |
|---|---|---|---|---|---|---|---|---|
| 275 | 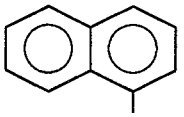 | H | H | H | 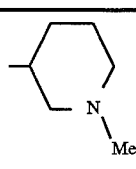 | 1 | HCl | 162–164 [EtOH—Et$_2$O] |
| 276 | " | " | " | " | 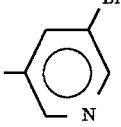 | " | " | 143–146 |
| 277 | " | " | " | — | 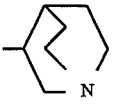 | 0 | " | 151.5–154 [EtOH—Et$_2$O] |
| 278 | " | " | " | H | 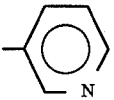 | 1 | " | 154–156 [EtOH—IPA] |

PRODUCTION EXAMPLE 26

The compounds shown in Table 19 were obtained in the same manner as in (1) and (2) of Production Example 16.

In Table 19, $R^1$, $R^2$, $R^3$, $R^4$, $R^6$ and n each show a substituent or integer used in the following general formula:

PRODUCTION EXAMPLE 27

2-(Imidazol-5-yl)methoxy-1-(1-naphthyl)ethanol was reacted with methyl iodide to obtain oily 2-(1-methylimidazol-5-yl)methoxy-1-(1-naphthyl)ethanol (compound No. 283).

TABLE 19

$$R^1-\underset{OR^2}{\underset{|}{CH}}-\underset{R^4}{\underset{|}{CH}}-O(CH_2)_n R^6$$
       $R^3$

| Compound No. | $R^1$ | $R^2$ | $R^3$ | $R^4$ | $R^6$ | n | Addition salt | Melting point (°C.) |
|---|---|---|---|---|---|---|---|---|
| 279 | 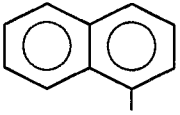 | H | H | H | 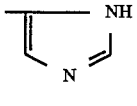 | 1 | — | Oily |
| 280 | " | " | " | " | " | " | 1/2 Fumaric acid | 167.5–170 [EtOH] |
| 281 | 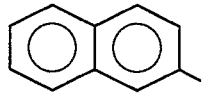 | " | " | " | " | " | — | 122–123 [Me$_2$CO—AcOEt] |
| 282 | 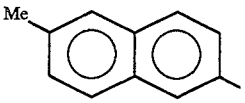 | " | " | " | " | " | — | 138–139 [Me$_2$CO—AcOEt] |

PRODUCTION EXAMPLE 28

(1) 6.0 g of 6-benzyloxy-2-naphthaldehyde was dissolved in 60 ml of tetrahydrofuran. The solution was cooled to $-30°$ C. Thereto was dropwise added, in 10 minutes, 30 ml of a tetrahydrofuran solution containing 1.6M of 2-chloroethoxymethylmagnesium chloride. The resulting mixture was stirred for 1 hour with ice cooling. The reaction mixture was added to a mixture of 100 ml of ice water, 100 ml of ethyl acetate and 3.6 g of ammonium chloride. The mixture was adjusted to pH 2 with 6N hydrochloric acid. The organic layer was separated, washed with water and a saturated aqueous sodium chloride solution in this order, and dried over anhydrous magnesium chloride. The solvent was removed by distillation under reduced pressure. The residue thus obtained was purified by column chromatography (eluant:toluene/ethyl acetate=20/1) to obtain a solid. To the solid was added 10 ml of diisopropyl ether. The resulting mixture was stirred at room temperature for 1 hour. The resulting crystals were collected by filtration and dried to obtain 4.7 g of 1-(6-benzyloxy-2-naphthyl)-2-(2-chloroethoxy)ethanol.

Melting point: 86°–87.5° C. [IPE]

(2) A mixture of 4.5 g of 1-(6-benzyloxy-2-naphthyl)-2-(2-chloroethoxy)ethanol, 1 g of potassium iodide, 10 ml of a 50% aqueous dimethylamine solution and 20 ml of ethanol was refluxed for 3 hours. To the reaction mixture was added 10 ml of a 50% aqueous dimethylamine solution. The resulting mixture was further refluxed for 6 hours. The reaction mixture was cooled and concentrated to about a half volume under reduced pressure. To the concentrate were added 100 ml of ethyl acetate and 100 ml of water. The mixture was adjusted to pH 10.5 with potassium carbonate. The organic layer was separated, washed with water and a saturated aqueous sodium chloride solution in this order, and dried over anhydrous magnesium sulfate. The solvent was removed by distillation under reduced pressure. To the residue thus obtained was added 30 ml of diethyl ether. The resulting crystals were collected by filtration and dried to obtain 3.9 g of 1-(6-benzyloxy-2-naphthyl)-2-[2-(N,N-dimethylamino)ethoxy]ethanol (compound No. 284).

Melting point: 100°–100.5° C. [EtOH—$H_2O$]

1-(6-Benzyloxy-2-naphthyl)-2-[2-(N,N-dimethylamino)ethoxy]ethanol was treated in the same manner as in Production Example 22, to obtain 1-(6-benzyloxy-2-naphthyl)-2-[2-(N,N-dimethylamino)ethoxy]ethanol hydrochloride (compound No. 285).

Melting point: 220°–220.5° C. [EtOH]

PRODUCTION EXAMPLE 29

In 12 ml of pyridine was suspended 3.0 g of 1-(6-benzyloxy-2-naphthyl)-2-[2-(N,N-dimethylamino)ethoxy]ethanol. To the suspension was added 1.6 ml of acetic anhydride. The resulting mixture was stirred at room temperature for 24 hours. After the completion of the reaction, the solvent was removed by distillation under reduced pressure. To the residue thus obtained were added 60 ml of ethyl acetate and 60 ml of water. The mixture was adjusted to pH 10.5 with potassium carbonate. The organic layer was separated. The aqueous layer was extracted with 30 ml of ethyl acetate. The extract was combined with the previously separated organic layer. The combined organic-layer was washed with water and a saturated aqueous sodium chloride solution in this order, and dried over anhydrous magnesium sulfate. The solvent was removed by distillation under reduced pressure. The residue thus obtained was dissolved in 30 ml of acetone. To the solution was added 1.5 ml of a 5N dry hydrogen chloride-ethanol solution. The resulting mixture was stirred at room temperature for 1 hour. The resulting crystals were collected by filtration and dried to obtain 2.6 g of 1-acetoxy-1-(6-benzyloxy-2-naphthyl)-2-[2-(N,N-dimethylamino)ethoxy]ethane hydrochloride (compound No. 286).

Melting point: 157°–158° C. [MeCN]

PRODUCTION EXAMPLE 30

A mixture of 2.0 g of 1-acetoxy-1-(6-benzyloxy-2-naphthyl)-2-[2-(N,N-dimethylamino)ethoxy]ethane hydrochloride, 0.5 g of 5% palladium-carbon and 40 ml of ethanol was subjected to hydrogenation at room temperature under atmospheric pressure. After the completion of the reaction, the palladium-carbon was removed by filtration. The solvent was removed by distillation under reduced pressure. Acetone was added to the residue thus obtained. The resulting crystals were collected by filtration and dried to obtain 0.76 g of 1-acetoxy-1-(6-hydroxy-2-naphthyl)-2-[2-(N,N-dimethylamino)ethoxy]ethane hydrochloride (compound No. 287).

Melting point: 150.5°–151.5° C. [EtOH]

PRODUCTION EXAMPLE 31

A mixture of 360 mg of 1-acetoxy-1-(6-hydroxy-2-naphthyl)-2-[2-(N,N-dimethylamino)ethoxy]ethane hydrochloride, 10 ml of water and 15 ml of chloroform was adjusted to pH 9 with a saturated aqueous sodium hydrogencarbonate solution. The organic layer was separated. The aqueous layer was extracted twice each with 10 ml of chloroform. The extracts were combined with the previously separated organic layer. The combined organic layer was washed with saturated aqueous sodium chloride solution and dried over anhydrous magnesium sulfate. The solvent was removed by distillation under reduced pressure. The residue thus obtained was dissolved in 6 ml of benzene. To the solution was added 0.12 ml of ethyl isocyanate. The resulting mixture was stirred for 4 hours at 80° C. The reaction mixture was cooled. The solvent was removed by distillation under reduced pressure. The residue thus obtained was purified by column chromatography (eluant:chloroform/ethanol=20/1) to obtain an oily product. The oily product was treated in the same manner as in Production Example 22 to obtain, as an amorphous, 150 mg of 1-acetoxy-1-[6-(N-ethylcarbamoyl)oxy-2-naphthyl]-2-[2-(N,N-dimethylamino)ethoxy]ethane hydrochloride (compound No. 288).

PRODUCTION EXAMPLE 32

2-[2-(N,N-dimethylamino)ethoxy]-1-(8-nitro-1-naphthyl)ethanol was obtained in the same manner as in (1) and (2) of Production Example 27. This compound was reacted with oxalic acid in the same manner as in (2) of Production Example 16 to obtain 2-[2-(N,N-dimethylamino)ethoxy]-1-(8-nitro-1-naphthyl)ethanol oxalate (compound No. 289).

Melting point: 150°–158.5° C.

PRODUCTION EXAMPLE 33

A mixture of 150 mg of 2-[2-(N,N-dimethylamino)ethoxy]-1-(8-nitro-1-naphthyl)ethanol oxalate, 150 mg of 5% palladium-carbon and 3 ml of methanol was subjected to hydrogenation at room temperature for 30 minutes under atmospheric pressure. After the completion of the reaction, the palladium-carbon was removed by filtration. The filtrate was subjected to distillation under reduced pressure to remove the solvent. The residue thus obtained was added to a mixture of 30 ml of ice water and 30 ml of chloroform. The mixture was adjusted to pH 11 with a 2N aqueous sodium hydroxide solution. The organic layer was separated, washed with water and a saturated aqueous sodium chloride solution in this order, and dried over anhydrous magnesium sulfate. The solvent was removed by distillation under reduced pressure. The residue thus obtained was dissolved in 1 ml of ethanol. Thereto was added 0.2 ml of a 5.9N dry hydrogen chloride-ethanol solution. The resulting crystals were collected by filtration and dried to obtain 110 mg of 1-(8-amino-1-naphthyl)-2-[2-(N,N-dimethylamino)ethoxy] ethanol dihydrochloride (compound No. 290).

Melting point: 195°–198° C. (decomp.) [AcOEt—EtOH]

PRODUCTION EXAMPLE 34

Triethylamine was added to 1-(8-amino-1-naphthyl)-2-[2-(N,N-dimethylamino)ethoxy]ethanol hydrochloride. The resulting mixture was reacted with methanesulfonyl chloride to obtain oily 2-[2-(N,N-dimethylamino)ethoxy]-1-(8-methylsulfonylamino-1-naphthyl)ethanol hydrochloride (compound No. 291).

PRODUCTION EXAMPLE 35

The same procedure as in (1) and (2) of Production Example 28 was repeated, except that the 6-benzyloxy-2-naphthaldehyde was replaced by 4-(N,N-dimethylamino)-1-naphthaldehyde, to obtain oily 1-[4-(N,N-dimethylamino)-1-naphthyl]-2-[2-(N,N-dimethylamino)ethoxy]ethanol dihydrochloride (compound No. 292).

PRODUCTION EXAMPLE 36

13 ml of ethanol was added to 1.3 g of 1-[4-N,N-dimethylamino)-1-naphthyl]-2-[2-(N,N-dimethylamino) ethoxy]ethanol dihydrochloride. The resulting mixture was refluxed for 1 hour. The reaction mixture was cooled. The solvent was removed by distillation under reduced pressure. To the residue thus obtained was added a mixture of 20 ml of ethyl acetate and 20 ml of water. The resulting mixture was adjusted to pH 10 with potassium carbonate. The organic layer was separated, washed with a saturated aqueous sodium chloride solution, and dried over anhydrous magnesium sulfate. The solvent was removed by distillation under reduced pressure to obtain 1.3 g of oily 1-ethoxy-1-[4-(N,N-dimethylamino)-1-naphthyl]-2-[2-(N,N-dimethylamino)ethoxy]ethane (compound No. 293).

PRODUCTION EXAMPLE 37

(1) 9.6 g of 5-bromo-1-hydroxyindane was dissolved in 100 ml of dry methylene chloride. To the solution were added, at room temperature, 570 mg of pyridinium p-toluenesulfonate and 4.5 ml of 3,4-dihydro-2H-pyran. The resulting mixture was stirred at the same temperature for 3 hours. The reaction mixture was added to ice water. The organic layer was separated, washed with a saturated aqueous sodium chloride solution, and dried over anhydrous magnesium sulfate. The solvent was removed by distillation under reduced pressure. The residue thus obtained was purified by column chromatography (eluant:toluene/ethyl acetate=15/1) to obtain 13.1 g of oily 5-bromo-1-(tetrahydropyran-2-yloxy)indane.

(2) 8.1 g of 5-bromo-1-(tetrahydropyran-2-yloxy)indane was dissolved in 100 ml of anhydrous tetrahydrofuran under a nitrogen atmosphere. To the solution was dropwise added 20 ml of a 1.5N n-butyllithiumhexane solution at −65° C. in 10 minutes. The resulting mixture was stirred at the same temperature for 5 minutes. Thereto was added 2.3 ml of anhydrous N,N-dimethylformamide. The reaction mixture was heated to room temperature and added to a mixture of 100 ml of ice water, 100 ml of diethyl ether and 2 g of ammonium chloride. The organic layer was separated, washed with water and a saturated aqueous sodium chloride solution in this order, and dried over anhydrous magnesium sulfate. The solvent was removed by distillation under reduced pressure. The residue thus obtained was purified by column chromatography (eluant:toluene/ethyl acetate=15/1) to obtain 6.5 g of 5-formyl-1-(tetrahydropyran-2-yloxy) indane.

(3) The same procedure as in (1) and (2) of Production Example 28 was repeated, except that the 6-benzyloxy-2-naphthaldehyde was replaced by 5-formyl-1-(tetrahydropyran-2-yloxy) indane, to obtain oily 2-[2-(N,N-dimethylamino)ethoxy]-1-[1-(tetrahydropyran-2-yloxy) indan-5-yl]ethanol (compound No. 294).

(4) A mixture of 2.5 g of 2-[2-(N,N-dimethylamino) ethoxy]-1-[1-(tetrahydropyran-2-yloxy)indan-5-yl]ethanol, 8 ml of acetic anhydride and 0.64 ml of pyridine was stirred at room temperature for 1 hour. The reaction mixture was added to a mixture of 50 ml of ice water and 50 ml of diethyl ether. The organic layer was separated and dried over anhydrous magnesium sulfate. The solvent was removed by distillation under reduced pressure. The residue thus obtained was purified by column chromatography (eluant:chloroform/methanol=10/1) to obtain 1.9 g of oily 1-acetoxy-2-[2-(N,N-dimethylamino)ethoxy]-1-[1-(tetrahydropyran-2-yloxy)indan- 5-yl]ethane (compound No. 295).

(5) 1.8 g of 1-acetoxy-2-[2-(N,N-dimethylamino)ethoxy] -1-[1-(tetrahydropyran-2-yloxy)indan-5-yl]ethane was added to 30 ml of a 4:2:1 mixed solution of acetic acid, tetrahydrofuran and water. The resulting mixture was stirred at 70° C. for 2 hours. The reaction mixture was cooled and added to a mixture of 100 ml of water and 100 ml of diethyl ether. The resulting mixture was adjusted to pH 8.5 with potassium carbonate. The organic layer was separated and dried over anhydrous magnesium sulfate. The solvent was removed by distillation under reduced pressure. The residue thus obtained was purified by column chromatography (eluant:chloroform/ethanol=10/1) to obtain 1.0 g of oily 1-acetoxy-1-[(1-hydroxy) indan-5-yl]-2-[2-(N,N-dimethylamino)ethoxy]ethane (compound No. 296).

(6) In 5 ml of pyridine was dissolved 1.0 g of 1-acetoxy-1-[(1-hydroxy)indan-5-yl]-2-[2-(N,N-dimethylamino) ethoxy]ethane. To the solution was added 0.3 ml of methanesulfonyl chloride at room temperature. The resulting mixture was stirred at the same temperature overnight. The reaction mixture was added to a mixture of 50 ml of ice water and 50 ml of diethyl ether. The resulting mixture was adjusted to pH 8.5 with potassium carbonate. The organic layer was separated and dried over anhydrous magnesium sulfate. The solvent was removed by distillation under reduced pressure. The residue thus obtained was purified by column chromatography (eluant:chloroform/methanol=10/1) to obtain 80 mg of oily 1-acetoxy-1-(1H-inden-6-yl)-2-[2-(N,N-dimethylamino)ethoxy]ethane (compound No. 297).

(7) In 0.5 ml of methanol was dissolved 80 mg of 1-acetoxy-1-(1H-inden-6-yl)-2-[2-(N,N-dimethylamino) ethoxy]ethane. To the solution was added 80 mg of a 28% sodium methoxide-methanol solution with ice cooling. The resulting mixture was stirred at room temperature for 20 minutes. The solvent was removed by distillation under reduced pressure. The residue thus obtained was purified by column chromatography (eluant:chloroform/methanol=20/1) to obtain a yellow oily product. The oily product was dissolved in 0.1 ml of ethanol. To the solution was added 0.1 ml of a 5.9N dry hydrogen chloride-ethanol solution at room temperature. The resulting crystals were collected by filtration to obtain 20 mg of 1-(1H-inden-6-yl)-2-[2-(N,N-dimethylamino)ethoxy]ethanol hydrochloride (compound No. 298).

Melting point: 168°–171° C. (decomp.) [AcOEt—EtOH]

Note: In the above name of the Compound No. 297 and 298 obtained, respectively, the term "inden-6-yl" was used because it is not clear yet to which carbon of the indene the carbon of the ethoxy group bonds.

PRODUCTION EXAMPLE 38

In the same manner as in the production of hydrochloride in (5) of Production Example 37 and Production Example 22, 2-[(1-hydroxy)indan-5-yl]-2-[2-(N,N-dimethylamino)ethoxy]ethanol hydrochloride (compound No. 299) was obtained.

Melting point: 150°–152° C. [IPA]

PRODUCTION EXAMPLE 39

2-[2-(N,N-dimethylamino)ethoxy]-1-(1-naphthyl)ethanol hydrochloride was reacted with acetic anhydride in pyridine in the presence of triethylamine to obtain oily 1-acetoxy-2-[2-(N,N-dimethylamino)ethoxy]-1-(1-naphthyl)ethane (compound No. 300).

PRODUCTION EXAMPLE 40

The compound obtained from 2-[2-(6-methylnaphthyl)]oxirane in the same manner as in (1) of Production Example 16 was reacted with hydrogen chloride gas in the same manner as in the production of hydrochloride in Production Example 22, to obtain oily 2-[2-(N-methyl-2,3-dihydropyridin-6H-5-yl)methoxy]-1-[2-(6-methylnaphthyl)]ethanol (compound No. 301).

PRODUCTION EXAMPLE 41

The compounds shown in Table 20 were obtained in the same manner as in (1) and (2) of Production Example 28.

In Table 20, $R^1$, $R^2$, $R^3$, $R^4$, $R^6$ and n each show a substituent or integer used in the following formula:

TABLE 20

$$R^1-CH-CH-O(CH_2)_n-R^6$$
$$\phantom{R^1-CH}| \phantom{CH-}| \phantom{O(CH_2)_n-}|$$
$$\phantom{R^1-}OR^2 \phantom{CH-O(CH_2)_n-}R^4$$

with $R^3$ on the second CH.

| Compound No. | $R^1$ | $R^2$ | $R^3$ | $R^4$ | $R^6$ | n | Addition salt | Melting point (°C.) |
|---|---|---|---|---|---|---|---|---|
| 302 | naphthyl | H | H | H | –N⌒N–Bz | 2 | 2HCl | 237–238 (decomp.) [EtOH—H₂O] |
| 303 | 1-methylnaphthyl | " | " | " | –N(Me)Me | " | HCl | 191–191.5 [IPA] |
| 304 | 1-methylnaphthyl | " | " | " | –N⌒N–(pyridyl with 2 N) | " | 2HCl | 175–176.5 (decomp.) [EtOH] |
| 305 | " | " | " | " | –N⌒N–(pyridyl) | " | " " | 122–124 [EtOH] |
| 306 | naphthyl | H | H | H | –N(Me)H | 3 | — | 119–120 [AcOEt] |
| 307 | " | " | " | " | –N(i-Pr)H | " | HCl | 139–140.5 [EtOH—AcOEt] |

TABLE 20-continued $$R^1-CH(OR^2)-CH(R^3)-O-(CH_2)_n-R^6 \text{ with } R^4$$

| Compound No. | R¹ | R² | R³ | R⁴ | R⁶ | n | Addition salt | Melting point (°C.) |
|---|---|---|---|---|---|---|---|---|
| 308 | " | " | " | " | 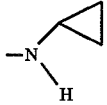 | " | " | 111.5–112 [EtOH—AcOEt] |
| 309 | 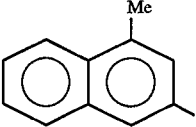 | " | " | " |  | 2 | " | 186–187 [EtOH—AcOEt] |
| 310 | 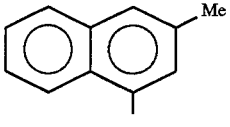 | H | H | H | 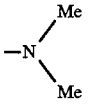 | 2 | HCl | 160–161.5 [EtOH—AcOEt] |
| 311 | 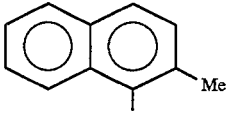 | " | " | " | " | " | " | 149–150 [EtOH-Me₂CO] |

PRODUCTION EXAMPLE 42

1.7 g of potassium tert-butoxide was added to 31 ml of 2-(N,N-dimethylamino)ethanol. The resulting mixture was heated to 80° C. To the solution was dropwise added, at 80°–85° C. in 1.5 hours, a solution of 5.2 g of 2-(benzo[b]thiophen-5-yl)oxirane dissolved in 8 ml of dimethyl sulfoxide. The resulting mixture was stirred at the same temperature for 1 hour. The reaction mixture was cooled and added to a mixture of 60 ml of ethyl acetate and 60 ml of ice water. The organic layer was separated. The aqueous layer was extracted with 30 ml of ethyl acetate. The extract was combined with the previously separated organic layer. To the combined organic layer was added 50 ml of ice water and the resulting mixture was adjusted to pH 1.5 with 6N hydrochloric acid. The aqueous layer was separated and 50 ml of chloroform was added thereto. The resulting mixture was adjusted to pH 10.5 with potassium carbonate. The organic layer was separated, washed with water and dried over anhydrous magnesium sulfate. The solvent was removed by distillation under reduced pressure. The resulting oily product was dissolved in 50 ml of acetone. To the solution was added 4.3 ml of a 5N dry hydrogen chloride-ethanol solution. The resulting mixture was stirred at room temperature for 1 hour and 20 ml of diethyl ether was then added thereto. The resulting mixture was further stirred for 1 hour. The resulting crystals were collected by filtration and dried to obtain 3.3 g of 1-(benzo[b]thiophen-5-yl)-2-[2-(N,N-dimethylamino)ethoxy]ethanol hydrochloride (compound No. 312).

Melting point: 191.5°–192.5° C. [EtOH—Me₂CO]

The compounds shown in Table 21 were obtained in the same manner.

In Table 21, R¹, R², R³, R⁴, R⁶ and n each show a substituent or integer used in the following formula:

TABLE 21

$$R^1-\underset{\underset{OR^2}{|}}{CH}-\underset{\underset{}{|}}{\overset{R^3}{CH}}-O(\underset{\underset{}{}}{\overset{R^4}{CH}})_n R^6$$

| Compound No. | R¹ | R² | R³ | R⁴ | R⁶ | n | Addition salt | Melting point (°C.) |
|---|---|---|---|---|---|---|---|---|
| 313 | 2-thienyl | H | H | H | −N(Me)Me | 2 | HCl | 139–141 |
| 314 | 3-thienyl | " | " | " | " | " | " | 165.5–166 [EtOH—Et₂O] |
| 315 | 3-pyridyl | " | " | " | " | " | 2HCl | 143–146 [EtOH] |
| 316 | 3-furyl | " | " | " | " | " | HCl | 128.5–130 [EtOH] |
| 317 | 4-quinolyl | H | H | H | −N(Me)Me | 2 | 2HCl | 185–185.5 [EtOH—IPA] |
| 318 | 2-furyl | " | " | " | " | " | HCl | 128–130 |
| 319 | 6-quinolyl | " | " | " | " | " | Fumaric acid | 136–136.5 [IPA] |
| 320 | benzo[b]thienyl | " | " | " | " | " | HCl | 166.5–167.5 [IPA—AcOEt] |
| 321 | 2,3-dihydrobenzofuranyl | " | " | " | " | " | " | 168.5–169.5 [IPA] |
| 322 | 2-oxoindolinyl | H | H | H | −N(Me)Me | 2 | HCl | 169–170 |
| 323 | 1-methylindolyl | " | " | " | " | " | — | Oily |
| 324 | benzo[b]thienyl | " | " | " | " | " | " | 188.5–189 [EtOH—AcOEt] |

TABLE 21-continued $$R^1-CH-CH-O-(CH_2)_n-R^6$$
$$\phantom{R^1-CH-}\vert\phantom{CH-O-}\vert$$
$$\phantom{R^1-CH-}OR^2\phantom{-O-}R^3\phantom{xx}R^4$$

| Compound No. | R¹ | R² | R³ | R⁴ | R⁶ | n | Addition salt | Melting point (°C.) |
|---|---|---|---|---|---|---|---|---|
| 325 | benzofuran | " | " | " | " | " | " | 168–169.5 [IPA—AcOEt] |
| 326 | 2-oxo-tetrahydroquinoline | " | " | " | " | " | " | 169–172 [EtOH] |
| 327 | benzothiophene | H | H | H | —N(morpholine)O | 2 | HCl | 166.5–167.5 [EtOH—Me₂CO] |
| 328 | N-Bz-indoline | " | " | " | —NMe₂ | " | — | Oily |
| 329* | indoline (NH) | " | " | " | " | " | 2HCl | " |
| 330 | benzothiophene | " | " | " | —N(piperidine) | " | HCl | 167.5–169 |
| 331 | N-Me-tetrahydroquinoline | " | " | " | —NMe₂ | " | 2HCl | Oily |
| 332 | 2,3-dihydrobenzothiophene | H | H | H | —NMe₂ | 2 | HCl | 207.5–210 [EtOH] |
| 333 | benzothiophene | " | " | " | " | " | " | 190.5–192 [EtOH—IPA] |
| 334 | benzothiophene | " | " | " | " | " | " | 171–172 [IPA—AcOEt] |
| 335 | benzothiophene | " | " | " | —N(2-pyrrolidinone) | " | — | Oily |

TABLE 21-continued $$R^1-\underset{\underset{OR^2}{|}}{CH}-\underset{\underset{}{|}}{\overset{R^3}{CH}}-O{\leftarrow}CH{\rightarrow}_{\overline{n}}R^6$$
(with $R^4$ on the second CH)

| Compound No. | $R^1$ | $R^2$ | $R^3$ | $R^4$ | $R^6$ | n | Addition salt | Melting point (°C.) |
|---|---|---|---|---|---|---|---|---|
| 336 | " | " | " | " |  -N(Me)Me | 3 | — | 81.5–85 |
| 337 | 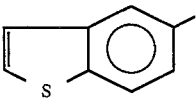 benzo[b]furan-5-yl | H | H | H | -N(Me)Me | 4 | HCl | 105–107 [EtOH—AcOEt] |
| 338 |  benzo[b]furan-5-yl with OH | | | | -N(Me)Me with Me on carbon | | Fumaric acid | 123–124.5 [EtOH—AcOEt] |

Note:
*: This compound can be obtained by subjecting compound No. 328 to conventional hydrogenation reaction.

PRODUCTION EXAMPLE 43

A mixture of 1.6 g of 3-pyridinemethanol, 1.7 g of potassium tert-butoxide and 23 ml of dimethyl sulfoxide was heated to 80° C. Thereto was added 2.4 g of 2-(benzo[b]furan-5-yl)oxirane. The resulting mixture was stirred at 85°–90° C. for 15 minutes. The reaction mixture was added to a mixture of 50 ml of ice water and 50 ml of ethyl acetate. The resulting mixture was adjusted to pH 1 with 6N hydrochloric acid. The aqueous layer was separated and 30 ml of ethyl acetate was added thereto. The resulting mixture was adjusted to pH 9.5 with potassium carbonate. The organic layer was separated, washed with water and a saturated aqueous sodium chloride solution in this order, and dried over anhydrous magnesium sulfate. The solvent was removed by distillation under reduced pressure. The residue thus obtained was purified by column chromatography (eluant:chloroform/ethanol=50/1) to obtain 0.56 g of 1-(benzo[b]furan-5-yl)-2-(pyridin-3-ylmethoxy)ethanol (compound No. 339).

Melting point: 85°–86° C. [IPE—EtOH]

The compounds shown in Table 22 were obtained in the same manner.

In Table 22, $R^1$, $R^2$, $R^3$, $R^4$, $R^6$ and n each show a substituent or integer used in the following formula:

TABLE 22

$$R^1-\underset{\underset{OR^2}{|}}{CH}-\underset{\underset{}{|}}{\overset{R^3}{CH}}-O{\leftarrow}CH{\rightarrow}_{\overline{n}}R^6$$
(with $R^4$ on the second CH)

| Compound No. | $R^1$ | $R^2$ | $R^3$ | $R^4$ | $R^6$ | n | Addition salt | Melting point (°C.) |
|---|---|---|---|---|---|---|---|---|
| 340 | 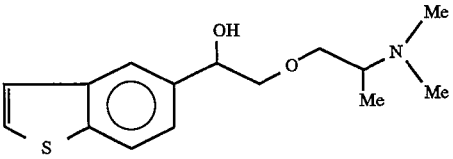 | H | H | H |  pyridyl | 1 | — | 106.5–107.5 [AcOEt—IPE] |
| 341 | 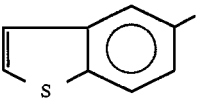 | " | " | " | " | " | HCl | Oily |

TABLE 22-continued $$R^1-CH(OR^2)-CH(R^3)(R^4)-O-(CH_2)_n-R^6$$

| Compound No. | R¹ | R² | R³ | R⁴ | R⁶ | n | Addition salt | Melting point (°C.) |
|---|---|---|---|---|---|---|---|---|
| 342 | benzo[b]thiophen-5-yl | " | " | " | piperidin-4-yl (N—Bz) | 2 | — | " |
| 343 | benzo[b]thiophen-5-yl | H | H | H | morpholin-2-yl (O, NH) | 1 | — | 121.5–125 [AcOEt] |
| 344 | " | " | " | " | 1-methylpiperidin-4-yl | " | " | 127–129.5 [EtOH—IPE] |
| 345 | " | " | " | " | 1-methyl-1,2,3,6-tetrahydropyridin-4-yl | " | " | 95.5–98 [AcOEt] |
| 346 | " | " | " | " | pyridin-3-yl | 0 | HCl | 181–185 [EtOH—AcOEt] |

PRODUCTION EXAMPLE 44

(1) A mixture of 5.7 g of potassium tert-butoxide and 57 ml of ethylene glycol was heated to 80° C. Thereto was added, in 1.5 hours, a solution of 18 g of 2-(benzo[b]thiophen-5-yl)oxirane dissolved in 30 ml of dimethyl sulfoxide. The resulting mixture was stirred at the same temperature for 30 minutes. The reaction mixture was added to a mixture of 120 ml of ice water and 80 ml of ethyl acetate. The organic layer was Separated. The aqueous layer was extracted twice each with 30 ml of ethyl acetate. The extracts were combined with the previously separated organic layer. The combined organic layer was washed with water and a saturated aqueous sodium chloride solution in this order, and dried over anhydrous magnesium sulfate. The solvent was removed by distillation under reduced pressure. The residue was purified by column chromatography (eluant:chloroform/ethanol=20/1) to obtain 9.1 g of 1-(benzo[b]thiophen-5-yl)-2-(2-hydroxyethoxy)ethanol.

Melting point: 119°–120.5° C. [EtOH—AcOEt]

(2) In 54 ml of pyridine was dissolved 9.0 g of 1-(benzo[b]thiophen-5-yl)-2-(2-hydroxyethoxy)ethanol. To the solution was added, at −25° C., 7.2 g of p-toluenesulfonyl chloride. The mixture was allowed to stand at 0°–5° C. for 24 hours and further at room temperature for 4 hours. The reaction mixture was added to a mixture of 103 ml of 6N hydrochloric acid, 50 ml of ice water and 100 ml of diethyl ether. The resulting mixture was adjusted to pH 2.0 with 6N hydrochloric acid. The organic layer was separated. The aqueous layer was extracted with 30 ml of diethyl ether. The extract was combined with the previously separated organic layer. The combined organic layer was washed with water and a saturated aqueous sodium chloride solution in this order, and dried over anhydrous magnesium sulfate. The solvent was removed by distillation under reduced pressure. The residue was purified by column chromatography (eluant:toluene/ethyl acetate=10/1) to obtain 7.7 g of colorless oily 1-(benzo[b]thiophen-5-yl)-2-[2-(p-toluenesulfonyloxy)ethoxy]ethanol.

(3) 0.97 g of pyridinium p-toluenesulfonate was added, at room temperature, to a solution of 7.6 g of 1-(benzo[b]thiophen-5-yl)-2-[2-(p-toluenesulfonyloxy)ethoxy]ethanol and 3.5 ml of 3,4-dihydro-2H-pyran dissolved in 40 ml of methylene chloride. The mixture was stirred at the same temperature for 20 minutes and further at 40 for 30 minutes. The reaction mixture was washed with water and dried over anhydrous magnesium sulfate. The solvent was removed by distillation under reduced pressure to obtain 8.7 g of colorless, oily 1-(benzo[b]thiophen-5-yl)-1-(2-tetrahydropyranyloxy)-2-[2-(p-toluenesulfonyloxy)ethoxy]ethane.

(4) In 15 ml of ethanol was dissolved 1.5 g of 1-(benzo[b]thiophen-5-yl)-1-(2-tetrahydropyranyloxy)-2-[2-(p-toluenesulfonyloxy)ethoxy]ethane. To the solution was added 4.9 ml of a 40% aqueous methylamine solution. The resulting mixture was refluxed for 1 hour. The reaction mixture was added to a mixture of 20 ml of ice water and 20 ml of diethyl ether. The organic layer was separated. The aqueous layer was extracted with 20 ml of diethyl ether. The extract was combined with the previously separated organic layer. To the combined organic layer was added 20 ml of water. The resulting mixture was adjusted to pH 1.5 with 6N hydrochloric acid and stirred at room temperature for 20 minutes. The aqueous layer was separated. The organic layer was extracted with 10 ml of water. The extract was combined with the previously separated aqueous layer. To the combined aqueous layer was added 30 ml of methylene chloride. The resulting mixture was adjusted to pH 11 with a 10% aqueous sodium hydroxide solution. The organic layer was separated. The aqueous layer was extracted with 15 ml of methylene chloride. The extract was combined with the previously separated organic layer and the combined organic layer was dried over anhydrous magnesium sulfate. The solvent was removed by distillation under reduced pressure. The residue thus obtained was dissolved in 7 ml of acetone. To the solution was added 0.5 ml of a 5N dry hydrogen chloride-ethanol solution. The resulting mixture was stirred at room temperature for 1 hour. To the reaction mixture was added 7 ml of diethyl ether. The resulting crystals were collected by filtration to obtain 0.5 g of 1-(benzo[b]thiophen-5-yl)-2-(N-methylaminoethoxy) ethanol hydrochloride (compound No. 347).

Melting point: 201.5°–202.5° C. [EtOH—Me$_2$CO]

The compounds shown in Table 23 were obtained in the same manner.

In Table 23, $R^1$, $R^2$, $R^3$, $R^4$, $R^6$ and n each show a substituent or integer used in the following formula:

PRODUCTION EXAMPLE 45

(1) The same procedure as in Production Example 43 was repeated, except that the 2-(benzo[b]furan-5-yl)oxirane and the 3-pyridinemethanol were replaced by 2-(benzo[b]thiophen-5-yl)oxirane and 1,4-diformyl-2-piperazinemethanol, respectively, to obtain oily 1-(benzo[b]thiophen-5-yl)-2-[(1,4-diformylpiperazin-2-yl)methoxy]ethanol (compound No. 354).

(2) In 1.5 ml of methanol was dissolved 270 mg of 1-(benzo[b]thiophen-5-yl)-2-[(1,4-diformylpiperazin-2-yl)methoxy]ethanol. To the solution was added 1.5 ml of a 5N dry hydrogen chloride-ethanol solution. The resulting mixture was allowed to stand at room temperature overnight. The resulting crystals were collected by filtration, washed with ethanol, and dried to obtain 150 mg of 1-(benzo[b]thiophen-5-yl)-2-[(piperazin-2-yl)methoxy]ethanol dihydrochloride (compound No. 355).

Melting point: 216°–218° C. (decomp.)

PRODUCTION EXAMPLE 46

(1) A mixture of 10 g of 2-(N-tritylamino)ethanol, 3.7 g of potassium tert-butoxide and 30 ml of dimethyl sulfoxide was heated to 85° C. Thereto was added a solution of 5.8 g of 2-(benzo[b]thiophen-5-yl)oxirane dissolved in 10 ml of dimethyl sulfoxide. The resulting mixture was stirred at the same temperature for 5 minutes. The reaction mixture was

TABLE 23

$$R^1-CH(OR^2)-CH(R^3)-O-(CH_2)_n-R^6 \text{ with } R^4$$

| Compound No. | $R^1$ | $R^2$ | $R^3$ | $R^4$ | $R^6$ | n | Addition salt | Melting point (°C.) |
|---|---|---|---|---|---|---|---|---|
| 348 | benzo[b]thiophen-5-yl | H | H | H | -N-cyclopropyl (H) | 2 | HCl | 196.5–197.5 [EtOH—Me$_2$CO] |
| 349 | " | " | " | " | -N(CH$_2$CH$_2$)$_2$N—Me | " | 2HCl | 232–234 [MeOH—Me$_2$CO] |
| 350 | " | " | " | " | -N(piperidyl)-C(=O)-C$_6$H$_4$-F | " | HCl | 219.5–220 [EtOH—AcOEt] |
| 351 | benzo[b]thiophen-5-yl | H | H | H | -N(Me)(Bz) | 2 | Oxalic acid | 138–149 [EtOH–AcOEt] |
| 352 | " | " | " | " | -N(CH$_2$CH$_2$)$_2$N-(pyrimidin-2-yl) | " | HCl | 170.5–171.5 [EtOH—AcOEt] |
| 353 | " | " | " | " | -NH-adamantyl | " | " | 222.5–223 [EtOH—AcOEt] | added to a mixture of 150 ml of ice water and 100 ml of ethyl acetate. The organic layer was separated. The aqueous layer was extracted with 30 ml of ethyl acetate. The extract was combined with the previously separated organic layer. The combined organic layer was washed with water and a saturated aqueous sodium chloride solution in this order, and dried over anhydrous magnesium sulfate. The solvent was removed by distillation under reduced pressure. To the residue thus obtained were added 70 ml of a 50% aqueous formic acid solution and 30 ml of tetrahydrofuran. The resulting mixture was stirred at 50°–60° C. for 1 hours. The solvent was removed by distillation under reduced pressure. To the residue thus obtained were added 50 ml of ethyl acetate and 30 ml of water. The resulting mixture was adjusted to pH 2 with 6N hydrochloric acid. The aqueous layer was separated. The organic layer was extracted twice each with 10 ml of water. The extracts were combined with the previously separated aqueous layer. To the combined aqueous layer was added 50 ml of methylene chloride and the resulting mixture was adjusted to pH 10.5 with potassium carbonate. The organic layer was separated, washed with water, and dried over anhydrous magnesium sulfate. The solvent was removed by distillation under reduced pressure to obtain 1.2 g of 1-(benzo[b]thiophen-5-yl)-2-(2-aminoethoxy)ethanol (compound No. 356.

Melting point: 87°–90.5° C. [EtOH—IPE]

(2) 1.1 g of 1-(benzo[b]thiophen-5-yl)-2-(2-aminoethoxy)ethanol was dissolved in 10 ml of ethanol. To the solution was added 290 mg of fumaric acid. The resulting mixture was stirred at room temperature for 30 minutes. To the reaction mixture was added 7 ml of diethyl ether. The resulting mixture was stirred at the same temperature for 1 hour. The resulting crystals were collected by filtration and dried to obtain 1.2 g of 1-(benzo[b]thiophen-5-yl)-2-(2-aminoethoxy)ethanol ½ fumarate (compound No. 357).

Melting point: 204.5°–205.5° C. [MeOH—EtOH]

PRODUCTION EXAMPLE 47

The same procedure as in Production Example 46 was repeated, except that the 2-(N-tritylamino)ethanol was replaced by (1-tritylimidazol-4-yl)methanol, to obtain 1-(benzo[b]thiophen-5-yl)-2-[(imidazolyl)methoxy]ethanol (compound No. 358) having a melting point of 128°–129° C. [AcOEt].

In the above name of the compound obtained, the term "(imidazolyl)methoxy" was used because it is not clear yet to which carbon of the 4- and 5-position carbons of the imidazolyl group the carbon of the methoxy group bonds.

PRODUCTION EXAMPLE 48

0.46 g of 1-(benzo[b]thiophen-5-yl)-2-(2-aminoethoxy)ethanol was dissolved in a mixture of 5 ml of water and 5 ml of dioxane. Thereto was added 0.21 g of sodium carbonate. The resulting mixture was heated to 50° C. Thereto was added 0.22 g of 2-chloropyrimidine. The resulting mixture was refluxed for 3 hours. The reaction mixture was added to a mixture of 30 ml of ice water and 30 ml of ethyl acetate. The organic layer was separated. The aqueous layer was extracted with 10 ml of ethyl acetate. The extract was combined with the previously separated organic layer. To the combined organic layer was added 20 ml of water and the resulting mixture was adjusted to pH 1.5 with 6N hydrochloric acid. The aqueous layer was separated. The organic layer was extracted with 10 ml of water. The extract was combined with the previously separated aqueous layer. To the combined aqueous layer was added 50 ml of methylene chloride and the resulting mixture was adjusted to pH 10.5 with potassium carbonate. The organic layer was separated, washed with water, and dried over anhydrous magnesium sulfate. The solvent was removed by distillation under reduced pressure. The residue thus obtained was purified by column chromatography (eluant:chloroform/ethanol=20/1) to obtain an oily product. To the oily product were added 2 ml of ethanol and 70 mg of maleic acid. The resulting mixture was stirred at room temperature for 1 hour. To the reaction mixture was added 2 ml of diethyl ether. The resulting crystals were collected by filtration and dried to obtain 0.28 g of 1-(benzo[b]thiophen-5-yl)-2-{[2-(pyrimidin-2-yl)amino]ethoxy}ethanol ½ maleate (compound No. 359).

Melting point: 113.5°–114.5° C. [IPA—AcOEt]

PRODUCTION EXAMPLE 49

0.39 g of N,N'-dicyclohexylcarbodiimide was added, with ice cooling, to a mixture of 0.45 g of 1-(benzo[b]thiophen-5-yl)-2-(2-aminoethoxy)ethanol, 0.23 g of nicotinic acid, 0.26 g of 1-hydroxybenzotriazole, 0.26 ml of triethylamine and 3 ml of tetrahydrofuran. The resulting mixture was stirred at the same temperature for 5 minutes and further at room temperature for 2 hours. To the reaction mixture were added 20 ml of water and 20 ml of ethyl acetate. The insolubles were removed by filtration. The filtrate was adjusted to pH 1.5 with 6N hydrochloric acid. The aqueous layer was separated. The organic layer was extracted twice each with 5 ml of water. The extracts were combined with the previously separated aqueous layer. To the combined aqueous layer was added 30 ml of chloroform and the resulting mixture was adjusted to pH 10.5 with potassium carbonate. The organic layer was separated, washed with water, and dried over anhydrous magnesium sulfate. The solvent was removed by distillation under reduced pressure. The residue thus obtained was purified by column chromatography (eluant:chloroform/ethanol=10/1). The resulting oily product was dissolved in 3 ml of ethanol. To the solution was added 0.24 ml of a 5N dry hydrogen chloride-ethanol solution. The resulting mixture was stirred at room temperature for 1 hour. To the reaction mixture was added 1.5 ml of diethyl ether. The resulting mixture was stirred at the same temperature for 1 hour. The resulting crystals were collected by filtration and dried to obtain 0.31 g of 1-(benzo[b]thiophen-5-yl)-2-[2-(nicotinoylamino)ethoxy]ethanol hydrochloride (compound No. 360).

Melting point: 152°–153° C. [EtOH—AcOEt]

PRODUCTION EXAMPLE 50

(1) 1.6 g of 4-methyl-2-formylthiazole was dissolved in 30 ml of tetrahydrofuran. The solution was cooled to −30° C. Thereto was dropwise added, in 10 minutes, 10 ml of a tetrahydrofuran solution containing 1.6M of 2-chloroethoxymethylmagnesium chloride. The mixture was stirred for 1 hour with ice cooling. The reaction mixture was added to a mixture of 50 ml of ice water, 50 ml of ethyl acetate and 2 g of ammonium chloride. The resulting mixture was adjusted to pH 2 with 6N hydrochloric acid and stirred at the same temperature for 5 minutes. The reaction mixture was adjusted to pH 6 with a saturated aqueous sodium hydrogencarbonate solution. The organic layer was separated, washed with water and a saturated aqueous sodium chloride solution in this order, and dried over anhydrous magnesium sulfate. The solvent was removed by distillation under reduced pressure. The residue thus obtained was purified by column chromatography (eluant:toluene/ethyl acetate=4/1) to obtain 1.3 g of oily 1-(4-methyl-2-thiazolyl)-2-(2-chloroethoxy)ethanol.

(2) A mixture of 1.2 g of 1-(4-methyl-2-thiazolyl)-2-(2-chloroethoxy)ethanol, 3 ml of a 50% aqueous dimethylamine solution, 0.45 g of potassium iodide and 20 ml of ethanol was refluxed for 3 hours. To the reaction mixture was added 3 ml of a 50% aqueous dimethylamine solution. The resulting mixture was refluxed for 3 hours. The solvent was removed by distillation under reduced pressure. To the residue thus obtained were added 30 ml of ethyl acetate and 30 ml of water. The resulting mixture was adjusted to pH 1.5 with 6N hydrochloric acid. The aqueous layer was separated and washed with 10 ml of ethyl acetate. Thereto was added 30 ml of ethyl acetate. The resulting mixture was adjusted to pH 10.5 with potassium carbonate. The organic layer was separated, washed with 10 ml of water and 10 ml of a saturated aqueous sodium chloride solution in this order, and dried over anhydrous magnesium sulfate. The solvent was removed by distillation under reduced pressure. The residue thus obtained was dissolved in 6 ml of ethanol. To the solution were added 0.6 ml of a 5N dry hydrogen chloride-ethanol solution and 6 ml of diethyl ether. The mixture was stirred at room temperature for 1 hour. The resulting crystals were collected by filtration, washed with 2 ml of a 1:1 mixture of diethyl ether and ethanol, and dried to obtain 390 mg of 1-(4-methyl-2-thiazolyl)-2-[2-(N,N-dimethylamino)ethoxy]ethanol hydrochloride (compound No. 361).

Melting point: 159°–160° C. [IPA—AcOEt]

The compounds shown in Table 24 were obtained in the same manner.

In Table 24, $R^1$, $R^2$, $R^3$, $R^4$, $R^6$ and n each show a substituent or integer used in the following formula:

TABLE 24

$$R^1-\underset{OR^2}{\underset{|}{CH}}-\underset{|}{\overset{R^3}{CH}}-O-(\underset{|}{\overset{R^4}{CH}})_n-R^6$$

| Compound No. | $R^1$ | $R^2$ | $R^3$ | $R^4$ | $R^6$ | n | Addition salt | Melting point (°C.) |
|---|---|---|---|---|---|---|---|---|
| 362 | benzimidazole-Tr | H | H | H | -N(Me)Me | 2 | — | Oily |
| 363*[1] | benzimidazole-H | " | " | " | " | " | 2HCl | 185–186.5 [EtOH—AcOEt] |
| 364 | indole-SO₂Ph | " | " | " | " | " | — | Oily |
| 365*[2] | indole-H | H | H | H | -N(Me)Me | 2 | — | Oily |
| 366 | Me-benzothiazole | " | " | " | " | " | HCl | 175–176 [EtOH—AcOEt] |
| 367 | N-Ph imidazole | " | " | " | " | " | 2HCl | Oily |
| 368 | Cl-thiophene-Me | " | " | " | " | " | HCl | 182.5–183 [EtOH—AcOEt] |
| 369 | benzofuran | H | H | H | —NH₂ | 2 | ½ Fumaric acid | 170–173 |

TABLE 24-continued $$R^1-\underset{\underset{OR^2}{|}}{CH}-\underset{\underset{}{|}}{\overset{\overset{R^3}{|}}{CH}}-O\underset{n}{(CH}\underset{}{\overset{\overset{R^4}{|}}{)}}R^6$$

| Compound No. | R¹ | R² | R³ | R⁴ | R⁶ | n | Addition salt | Melting point (°C.) |
|---|---|---|---|---|---|---|---|---|
| 370 | 3-methoxy-2-pyridyl (pyridine with OMe) | " | " | " | −N(Me)Me | " | 2HCl | 116–117 [EtOH—Me₂CO] |
| 371 | 2-pyridyl | " | " | " | " | " | " | 179–179.5 [EtOH—AcOEt] |
| 372 | 1-Bz-imidazol-2-yl | " | " | " | " | " | " | 155–156 [EtOH—AcOEt] |
| 373 | 4-pyridyl | H | H | H | −N(Me)Me | 2 | 2HCl | 184–186 [EtOH—AcOEt] |
| 374 | 6-chloro-3-fluoro-2-methoxy-pyridyl | " | " | " | " | " | HCl | 196–197 [MeOH] |
| 375 | benzothiophen-2-yl | " | " | " | −N(Me)H | " | " | 193–193.5 [EtOH—AcOEt] |
| 376*³ | 3-fluoro-2-methoxy-pyridyl | " | " | " | −N(Me)Me | " | " | 162–163 [IPA] |
| 377 | 6-chloro-3-fluoro-2-(methylamino)pyridyl | H | H | H | −N(Me)Me | 2 | HCl | 153.5–154 [IPA] |
| 378 | 3-fluoro-2-(methylamino)pyridyl | " | " | " | " | " | 2HCl | 176–179 |
| 379 | benzofuran-2-yl | " | " | " | −N(Et)Et | " | — | Oily |
| 380 | 1H-benzimidazol-2-yl (quinoxaline-NH) | " | " | " | −N(Me)Me | " | " | " |

TABLE 24-continued $$R^1-CH-CH-O-(CH)_n-R^6$$
$$\phantom{R^1-CH-}|\phantom{CH-O-(CH)_n-R^6}|\phantom{R^6}$$
$$\phantom{R^1-CH-}OR^2\phantom{CH-O-(CH)_n-}R^4$$

with $R^3$ on the middle CH and $R^4$ on the $(CH)_n$.

| Compound No. | R¹ | R² | R³ | R⁴ | R⁶ | n | Addition salt | Melting point (°C.) |
|---|---|---|---|---|---|---|---|---|
| 381 | benzothiophen-2-yl | H | H | H | —NH—cyclopropyl | 2 | HCl | 194.5–195 [EtOH—AcOEt] |
| 382 | 5-methylbenzothiophen-2-yl | " | " | " | —N(H)(Me) | 3 | — | 109–111 [AcOEt] |
| 383 | " | " | " | " | —NH—cyclopropyl | " | HCl | 133.5–134.5 [EtOH—AcOEt] |
| 384 | " | " | " | " | —NH—i-Pr | " | " | 136.5–139.5 [EtOH—AcOEt] |
| 385 | 5-Me-benzothiophen-2-yl | H | H | H | —N(Me)(Me) | 2 | HCl | 193–193.5 [EtOH—AcOEt] |
| 386 | 6-BzO-benzofuran-2-yl | " | " | " | " | " | " | 171.5–172 [EtOH—AcOEt] |
| 387 | 5-methylbenzothiophen-2-yl | " | " | " | —N(piperidinyl) | 3 | " | 137.5–139.5 [EtOH—AcOEt] |
| 388 | " | " | " | " | —N(Et)(Et) | 2 | " | 138.5–139 [EtOH—AcOEt] |
| 389 | 5-Me-benzothiophen-2-yl | H | H | H | —NH—i-Pr | 2 | HCl | 184–184.5 [EtOH—AcOEt] |
| 390 | " | " | " | " | —N(Me)(Me) | 3 | — | 68.5–69.5 [Hexane] |
| 391 | " | " | " | " | —N(piperazinyl)—Bz | 2 | 2HCl | 250–252.5 (decomp.) [MeOH—H₂O] |
| 392 | " | " | " | " | —N(piperazinyl)-(2-pyridyl) | " | " | 155–157 [EtOH] |

TABLE 24-continued $$R^1-CH-CH-O+CH\frac{}{n}R^6$$
with substituents $R^3$, $R^4$ on the CH groups and $OR^2$ on the first CH.

| Compound No. | R¹ | R² | R³ | R⁴ | R⁶ | n | Addition salt | Melting point (°C.) |
|---|---|---|---|---|---|---|---|---|
| 393 | 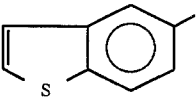 | H | H | H |  -NH-Me | 3 | — | 65–67.5 [IPA—IPE] |
| 394 | " | " | " | " | 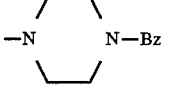 -N\_\_N—Bz | 2 | 2HCl | 234–234.5 [MeOH—AcOEt] |
| 395 | " | " | " | " |  -NH-Me | " | HCl | 178–180.5 [IPA—AcOEt] |
| 396 | 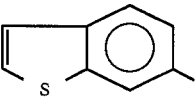 | " | " | " |  -N(Me)Me | 3 | — | 52–53 [IPE] |
| 397 | 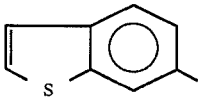 | H | H | H |  -NH-Me | 3 | — | 81.5–83 [IPA—IPE] |
| 398 | " | " | " | " | " | 2 | HCl | 196–198 [EtOH—AcOEt] |
| 399 | " | " | " | " | 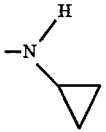 -NH-cyclopropyl | " | " | 190–192.5 [EtOH—AcOEt] |
| 400 | 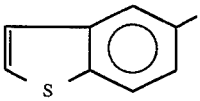 | " | " | " |  -N⁺(Me)₃ | " | ½ 1,5-naphthalene-disulfonic acid | Amorphous |
| 401 | 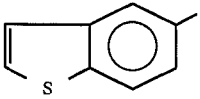 | Ac | H | H |  -N(Me)Me | 2 | HCl | Oily |
| 402 | 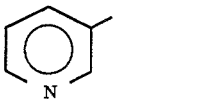 | H | " | " | 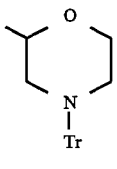 morpholine-N-Tr | 1 | — | " |
| 403 | " | " | " | " | 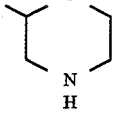 morpholine-NH | " | ½ Maleic acid | 110–117 |

Note:
*¹: This compound can be obtained by subjecting compound No. 362 to hydrolysis reaction using hydrochloric acid.
*²: This compound can be obtained by subjecting compound No. 364 to hydrolysis reaction using sodium hydroxide.
*³: This compound can be obtained by subjecting compound No. 374 to conventional hydrogenation reaction.

PRODUCTION EXAMPLE 51

(1) A mixture of 9.2 g of 1-(2-thienyl)-2-[2-(N,N-dimethylamino)ethoxy]ethanol and 18 ml of acetic anhydride was refluxed for 10 minutes. The reaction mixture was dropwise added to a mixture of 7.8 ml of concentrated nitric acid and 27 ml of acetic anhydride at 0° C. in 30 minutes. The resulting mixture was stirred at the same temperature for 2 hours. The reaction mixture was added to a saturated aqueous sodium hydrogen-carbonate solution with the pH of the resulting mixture having been adjusted to 7 with a 40% aqueous sodium hydroxide solution. The resulting mixture was adjusted to pH 10 with a 40% aqueous sodium hydroxide solution and 300 ml of chloroform was added thereto. The organic layer was separated and 300 ml of water was added thereto. The resulting mixture was adjusted to pH 2 with 6N hydrochloric acid. The aqueous layer was separated and 300 ml of chloroform was added thereto. The resulting mixture was adjusted to pH 10 with a 40% aqueous sodium hydroxide solution. The organic layer was separated, washed with water, and dried over anhydrous magnesium sulfate. The solvent was removed by distillation under reduced pressure to obtain 10.4 g of oily 1-(5-nitro-2-thienyl)-1-acetoxy-2-[2-(N,N-dimethylamino)ethoxy]ethane (compound No. 404).

(2) In 10 ml of methanol was dissolved 320 mg of 1-(5-nitro-2-thienyl)-1-acetoxy-2-[2-(N,N-dimethylamino)ethoxy]ethane. To the solution was added 1.27 ml of a 1N aqueous sodium hydroxide solution. The resulting mixture was stirred at room temperature for 1 hour. To the reaction mixture were added 40 ml of chloroform and 40 ml of water. The organic layer was separated and 30 ml of water was added thereto. The resulting mixture was adjusted to pH 2 with 6N hydrochloric acid. The aqueous layer was separated and 30 ml of chloroform was added thereto. The resulting mixture was adjusted to pH 11 with a 10% aqueous sodium hydroxide solution. The organic layer was separated, washed with water, and dried over anhydrous magnesium sulfate. The solvent was removed by distillation under reduced pressure. To the residue thus obtained were added 3 ml of methanol and 1 ml of a 5N dry hydrogen chloride-ethanol solution. The solvent was removed by distillation under reduced pressure. To the residue thus obtained was added 5 ml of ethanol. The resulting crystals were collected by filtration and dried to obtain 170 mg of 1-(5-nitro-2-thienyl)-2-[2-(N,N-dimethylamino)ethoxy]ethanol (compound No. 405).

Melting point: 189°–191.5° C. (decomp.)

PRODUCTION EXAMPLE 52

(1) In 10 ml of pyridine was dissolved 3.4 g of 2-[2-(N,N-dimethylamino)ethoxy]-1-(6-benzyloxybenso[b]furan-2-yl) ethanol. To the solution was added 1.8 ml of acetic anhydride. The resulting mixture was stirred at room temperature for 17.5 hours. The solvent was removed by distillation under reduced pressure. To the residue thus obtained were added 40 ml of ethyl acetate and 40 ml of water. The resulting mixture was adjusted to pH 7 with sodium hydrogencarbonate. The organic layer was separated. The aqueous layer was extracted with 20 ml of ethyl acetate. The extract was combined with the previously separated organic layer. The combined organic layer was washed with water and a saturated aqueous sodium chloride solution in this order, and dried over anhydrous magnesium sulfate. The solvent was removed by distillation under reduced pressure. The residue thus obtained was purified by column chromatography (eluant:chloroform/ethanol=1/1) to obtain 3.25 g of oily 1-acetoxy-1-(6-benzyloxybenzo[b]furan-2-yl)-2-[2-(N,N-dimethylamino)ethoxy]ethane (compound No. 406).

IR (neat) cm$^{-1}$: $v_{C=O}$ 1740

(2) A mixture of 3.2 g of 1-acetoxy-1-(6-benzyloxybenzo[b]furan-2-yl)-2-[2-(N,N-dimethylamino)ethoxy]ethane, 0.6 g of 5% palladium-carbon, 0.67 ml of concentrated hydrochloric acid and 30 ml of methanol was subjected to hydrogenation at room temperature under atmospheric pressure for 1.5 hours. After the completion of the reaction, the palladium-carbon was removed by filtration. The solvent was removed by distillation under reduced pressure. To the residue thus obtained were added 20 ml of chloroform and 20 ml of water. The resulting mixture was adjusted to pH 7 with sodium hydrogencarbonate. The organic layer was separated. The aqueous layer was extracted with 10 ml of chloroform. The extract was combined with the previously separated organic layer. The combined organic layer was washed with 5 ml of water, and dried over anhydrous magnesium sulfate. The solvent was removed by distillation under reduced pressure. The residue thus obtained was purified by column chromatography (eluant:chloroform/methanol=7/1) to obtain 1.57 g of oily 1-acetoxy-1-(6-hydroxybenzo[b]furan-2-yl)-2-[2-(N,N-dimethylamino)ethoxy]ethane (compound No. 407).

IR (neat) cm$^{-1}$: $v_{C=O}$ 1740

(3) In 3.5 ml of benzene was dissolved 0.65 g of 1-acetoxy-1-(6-hydroxybenzo[b]furan-2-yl)-2-[2-(N,N-dimethylamino)ethoxy]ethane. To the solution was added 0.33 ml of ethyl isocyanate. The resulting mixture was stirred for 30 minutes at 80° C. The solvent was removed by distillation under reduced pressure. The residue thus obtained was purified by column chromatography (eluant:chloroform/ethanol=6/1) to obtain an oily product. The oily product was treated with dry hydrogen chloride according to a conventional method to obtain 0.58 g of oily 1-acetoxy-1-(6-N-ethylcarbamoyloxybenzo[b]furan-2-yl)-2-[2-(N,N-dimethylamino)ethoxy]ethane hydrochloride (compound No. 408).

IR (neat) cm$^{-1}$: $v_{C=O}$ 1730

Next, this invention is specifically described by way of Examples. However, this invention is in no way restricted to these Examples.

PRODUCTION EXAMPLE 53

The compounds shown in Table 25 were obtained in the same manner as in Production Example 50.

In Table 25, $R^1$, $R^2$, $R^3$, $R^4$, $R^6$ and n each show a substituent or integer used in the following formula:

Example 1

(Tablets)

Tablets each containing 50 mg of 1-(4-benzyloxyphenyl)-2-[2-(N,N-dimethylamino)ethoxy]ethanol hydrochloride (compound No. 48) were prepared using the following recipe according to the following method:

| Per tablet: | | |
|---|---|---|
| Compound No. 48 | 50 mg | ① |
| Lactose | 20 mg | |
| Kollidon CL (BASF's product) | 15 mg | |
| Corn starch | 30 mg | |
| AVICEL PH 101 (Asahi Kasei's product) | 50 mg | |
| Polyvinylpyrrolidone K-90 | 5 mg | |
| Light silica | 3 mg | ② |
| Magnesium stearate | 2 mg | |
| Total | 175 mg | |

The components ① were kneaded with an aqueous solution containing 8% of Polyvinylpyrrolidone K-90. The kneaded product was dried at 40° C. and mixed with the components ②. The resulting mixture was made into round tablets each weighing 175 mg and having

PRODUCTION EXAMPLE 54

The compounds shown in Table 26 were obtained in the same manner as in

PRODUCTION EXAMPLE 42.

In Table 26, $R^1$, $R^2$, $R^3$, $R^4$, $R^6$ and n each show a substituent or integer used in the following formula:

TABLE 25

$$R^1-\underset{\underset{OR^2}{|}}{CH}-\underset{\underset{}{|}}{\overset{\overset{R^3}{|}}{CH}}-O(CH_2)_n-R^6 \text{ with } R^4$$

| Compound No. | $R^1$ | $R^2$ | $R^3$ | $R^4$ | $R^6$ | n | Addition salt | Melting point (°C.) |
|---|---|---|---|---|---|---|---|---|
| 409 | benzothiophenyl | H | H | H | $-N(Et)_2$ | 2 | ½ fumaric acid | 162.5 ~ 163 [EtOH] |
| 410 | benzothiophenyl | " | " | " | " | " | " | 131 ~ 132.5 [EtOH] |
| 411 | benzothiophenyl | " | " | " | " | 3 | — | 59.5 ~ 60.5 [IPA] |
| 412 | benzothiophenyl | H | H | H | $-N(Et)_2$ | 2 | ½ fumaric acid | 131 ~ 132 [EtOH] |
| 413 | benzothiophenyl | " | " | " | $-N(iPr)_2$ | " | HCl | 167 ~ 168 |
| 414 | " | " | " | " | $-N(Et)_2$ | 4 | " | oily |
| 415 | benzothiophenyl | " | " | " | " | 2 | " | 152 ~ 153 [EtOH—AcOEt] |

TABLE 26
$$R^1-CH(OR^2)-CH(R^3)-O-(CH_2)_n-CH(R^4)-R^6$$
| Compound No. | R¹ | R² | R³ | R⁴ | R⁶ | n | Addition salt | Melting point (°C.) |
|---|---|---|---|---|---|---|---|---|
| 416 | *a 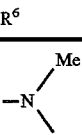 (S form) | H | H | H | —N(Me)(Me) | 2 | HCl | 180 ~ 180.5 [EtOH—Me₂CO] |
| 417 | 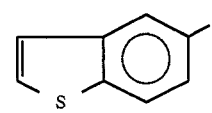 (R form) | " | " | " | " | " | " | 179 ~ 180 |
| 418 | *b 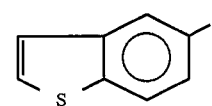 (S form) | " | " | " | —N(Et)(Et) | " | " | 119.5 ~ 120.5 [EtOH—AcOEt] |
| 419 | 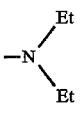 (R form) | H | H | H | —N(Et)(Et) | 2 | HCl | 120 ~ 120.5 |
| 420 | *c 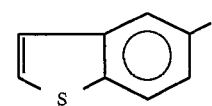 (S form) | " | " | " | —N(piperidine) | " | " | 175 ~ 176 [EtOH—AcOEt] |
| 421 | 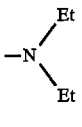 (R form) | " | " | " | " | " | " | 174 ~ 175.5 |
| 422 | *d 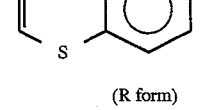 (S form) | " | " | " | —N(Me)(Me) | 3 | " | 148.5 ~ 150 [EtOH—AcOEt] |
| 423 | 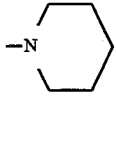 (R form) | H | H | H | —N(Me)(Me) | 3 | HCl | 148.5 ~ 150 |

TABLE 26-continued $$R^1-CH-CH-O(CH)_n-R^6$$
$$\phantom{R^1-CH-}|\phantom{CH-O}|\phantom{CH)_n-R^6}$$
$$\phantom{R^1-CH-}OR^2\phantom{-O(CH)_n-R^6}$$

with substituents $R^3$ on the middle CH and $R^4$ on the (CH)$_n$ group.

| Compound No. | R¹ | R² | R³ | R⁴ | R⁶ | n | Addition salt | Melting point (°C.) |
|---|---|---|---|---|---|---|---|---|
| 424 | *e (benzothiophene, S form) | " | " | " | −N(Et)(Et) | " | — | 75.5 ~ 76.5 [IPA] |
| 425 | (benzothiophene, R form) | " | " | " | " | " | " | 75.5 ~ 76.5 |
| 426 | *e (benzothiophene, S form) | " | " | " | −N(piperidine) | " | HCl | 144 ~ 145.5 [IPA] |
| 427 | (benzothiophene, R form) | H | H | H | −N(piperidine) | 3 | HCl | 151 ~ 152 [EtOH-AcOEt] |
| 428 | *g (benzothiophene, R form) | " | " | " | −N(Me)(Me) | 4 | " | 151 ~ 152 [EtOH—AcOEt] |
| 429 | (benzothiophene, R form) | " | " | " | " | " | " | 150.5 ~ 151 |
| 430 | *h (benzothiophene, R form) | " | " | " | −N(Et)(Et) | " | " | oily |

TABLE 26-continued $$R^1-CH-CH-O(CH_2)_n-R^6$$
with $R^3$, $R^4$ on the middle CH groups and $OR^2$ below

| Compound No. | R¹ | R² | R³ | R⁴ | R⁶ | n | Addition salt | Melting point (°C.) |
|---|---|---|---|---|---|---|---|---|
| 431 | benzothiophene (R form) | H | H | H | –N(Et)(Et) | 4 | HCl | oily |

Note:
*a: Optical rotation: +48.5° (25° C., C = 1.5, MeOH)
*b: Optical rotation: +47.8° (25° C., C = 1.5, MeOH)
*c: Optical rotation: +42.4° (25° C., C = 1.5, MeOH)
*d: Optical rotation: +47.4° (25° C., C = 1.5, MeOH)
*e: Optical rotation: +19.1° (25° C., C = 1.5, MeOH)
*f: Optical rotation: +41.2° (25° C., C = 1.5, MeOH)
*g: Optical rotation: +32.6° (25° C., C = 1.5, MeOH)
*h: Optical rotation: +22.9° (25° C., C = 1.5, MeOH)

a diameter of 8 mm.

Example 2

(Capsules)

Capsules each containing 50 mg of 2-[2-(N,N-dimethylamino)ethoxy]-1-[4-(4-phenyloxy)phenyl]ethanol hydrochloride (compound No. 54) were prepared using the following recipe according to the following method:

| Per capsule: | | |
|---|---|---|
| Compound No. 54 | 50 mg | ① |
| Lactose | 20 mg | ① |
| Corn starch | 53 mg | ① |
| Kollidon CL (BASF's product) | 2 mg | ① |
| Polyvinylpyrrolidone K-90 | 5 mg | ① |
| AVICEL PH 302 (Asahi Kasei's product) | 18 mg | ② |
| Magnesium stearate | 2 mg | ② |
| Total | 150 mg | |

The components ① were kneaded with an aqueous solution containing 8% of Polyvinylpyrrolidone K-90. The kneaded product was dried at 40° C. and mixed with the components ②. The resulting mixture was charged into No. 3 gelatin capsules in an amount of 150 mg per capsule to obtain capsules.

Example 3

(Liquid)

A liquid containing 25 mg of 2-[2-(N,N-dimethylamino)ethoxy]-1-(3-trifluoromethylphenyl)ethanol hydrochloride (compound No. 42) was prepared using the following recipe according to the following method:

| Per ampule: | |
|---|---|
| Compound No. 42 | 25 mg |
| Methyl paraoxybenzoate | 1 mg |
| Total | 26 mg |

The above components were dissolved in physiological saline and the total volume of the solution was made into 1 ml. The solution was filtered aseptically and charged into an ampule to obtain a liquid.

Example 4

(Injection)

An injection containing 25 mg of 2-[2-(N,N-dimethylamino)ethoxy]-1-(3-fluorophenyl)ethanol hydrochloride (compound No. 1) was prepared using the following recipe according to the following method:

| | |
|---|---|
| Compound No. 1 | 25 mg |
| Manitol | 75 mg |
| Total | 100 mg |

The above components were dissolved in 1.5 ml of distilled water prepared for injection. The solution was filtered aseptically, charged into a 3-ml minivial, and freeze-dried to obtain an injection.

Example 5

(fine granules)

Fine granules each containing 50 mg of 2-(1-benzylpiperidin-4-yloxy)-1-phenylethanol hydrochloride (compound No. 112) were prepared using the following recipe according to the following method:

| | |
|---|---|
| Compound No. 112 | 50 mg |
| α-Starch | 200 mg |
| Purified sucrose | 250 mg |
| Lactose | 470 mg |
| Polyvinylpyrrolidone K-90 | 30 mg |
| Total | 1000 mg |

①

The components ① were subjected to granulation under high speed stirring with an aqueous solution containing 8% of Polyvinylpyrrolidone K-90. The granules obtained were sieved through a 32-mesh screen and dried to obtain fine granules.

Example 6

(Tablets)

2-[2-(N,N-dimethylamino)ethoxy]-1-(3-methylphenyl) ethanol hydrochloride (compound No. 15), 2-[(1-methylimidazol-5-yl)methoxy]-1-(4-benzyloxyphenyl) ethanol (compound No. 215), 2-[2-(N,N-dimethylamino) ethoxy]-1-(1-naphthyl) ethanol hydrochloride (compound No. 228), 2-[2-(N,N-dimethylamino)ethoxy]-1-(2-naphthyl) ethanol hydrochloride (compound No. 229), 2-[2-(N,N-dimethylamino)ethoxy]-1-(benzo[b]thiophen-5-yl)ethanol hydrochloride (compound No. 312), 2-[(N-methyl-1H-1,2,5,6-tetrahydropyridin-3-yl)methyl]-1-(benzo[b]-thiophen-5-yl)ethanol (compound No. 345), 2-(2-aminoethoxy)-1-(benzo[b]thiophen-5-yl)ethanol ½ fumarate (compound No. 357), 2-[2-(N,N-diethylamino)ethoxy]-1-(benzo[b]thiophen-5-yl)ethanol hydrochloride (compound No. 388) and 2-[2-(4-benzylpiperazin-1-yl)ethyl]-1-(benzo[b]furan-5-yl)ethanol dihydrochloride (compound No. 394) were processed as in Example 1 to obtain tablets each containing 50 mg of one of the above compounds.

Example 7

(Capsules)

2-[2-(N,N-dimethylamino)ethoxy]-1-(3-methylphenyl) ethanol hydrochloride (compound No. 15), 2-[(1-methylimidazol-5-yl)methoxy]-1-(4-benzyloxyphenyl) ethanol (compound No. 215), 2-[2-(N,N-dimethylamino) ethoxy]-1-(1-naphthyl)ethanol hydrochloride (compound No. 228), 2-[2-(N,N-dimethylamino)ethoxy]-1-(2-naphthyl) ethanol hydrochloride (compound No. 229), 2-[2-(N,N-dimethylamino)ethoxy]-1-(benzo[b]thiophen-5-yl)ethanol hydrochloride (compound No. 312), 2-[(N-methyl-1H-1,2,5,6-tetrahydropyridin-3-yl) methyl]- 1-(benzo[b]thiophen-5-yl)ethanol (compound No. 345), 2-(2-aminoethoxy)-1-(benzo[b]thiophen-5-yl)ethanol ½ fumarate (compound No. 357), 2-[2-(N,N-diethylamino)ethoxy]-1-(benzo[b] thiophen-5-yl) ethanol hydrochloride (compound No. 388) and 2-[2-(4-benzylpiperazin-1-yl)ethyl]-1-(benzo[b]furan-5-yl)ethanol dihydrochloride (compound No. 394) were processed as in Example 2 to obtain capsules each containing 50 mg of one of the above compounds.

What is claimed is:

1. A 1,2-ethanediol derivative represented by the following formula or a salt thereof:

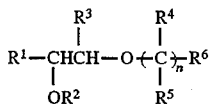

wherein $R^1$ represents a substituted or unsubstituted heterocyclic group selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl, indazolyl, furyl, thienyl, pyranyl, isobenzofuranyl, oxazolyl, benzofuranyl, indolyl, benzimidazolyl, benzoxazolyl, benzothiazolyl, quinoxalyl, dihydroquinoxalyl, 2,3-dihydrobenzopyrrolyl, 2,3-dihydro-4H-1-thianaphthyl, 2,3-dihydrobenzofuranyl, benzo[b] dioxanyl, imidazo[2,3-a]pyridyl, benzo[b]piperazinyl, chromenyl, isothiazolyl, isoxazolyl, oxadiazolyl, pyridazinyl, isoindolyl and isoquinolyl; $R^2$ represents a hydrogen atom, a lower alkyl group or a hydroxyl-protecting group; $R^3$ represents a hydrogen atom or a lower alkyl group; $nR^4$'s and $nR^5$'s are the same as or different from one another and represent hydrogen atoms or lower alkyl groups; $R^6$ represents an ammonio group or a substituted or unsubstituted amino or nitrogen-containing heterocyclic group, the nitrogen-containing heterocyclic group being selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl groups; and n represents 0 or an integer of 1 to 6, wherein the substituent on $R^1$ is selected from the group consisting of halogen atoms, substituted or unsubstituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonyl amino and heterocyclic groups, protected amino groups, protected or unprotected hydroxyl groups, nitro group, oxo group and lower alkylenedioxy groups; the substituted lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino or heterocyclic group as the substituent of $R^1$ and the substituted nitrogen-containing heterocyclic group as $R^6$ have each at least one substituent selected from the group consisting of halogen atoms, protected or unprotected hydroxyl groups, protected or unprotected amino groups, protected or unprotected carboxyl groups, unsubstituted lower alkyl groups, lower alkyl groups substituted by a protected or unprotected hydroxyl group, unsubstituted or halogen-substituted aryl groups, unsubstituted or halogen-substituted aroyl groups, unsubstituted lower alkoxy groups, lower alkoxy groups substituted by a lower alkoxy group, lower acyl groups, ar-lower alkyl groups, ar-lower alkenyl groups, heterocyclic groups, heterocyclic-CO-groups, oxo group, lower alkylsulfonyl groups and arylsulfonyl groups; and the substituted amino group as the substituent of $R^1$ and the substituted amino group as $R^6$ have each at least one substituent selected from the group consisting of protected or unprotected hydroxyl groups, unsubstituted lower alkyl groups, lower alkyl groups substituted by a protected or unprotected carboxyl or hydroxyl group, cycloalkyl groups, aryl groups, lower acyl groups, ar-lower alkyl groups, heterocyclic groups, unsubstituted or oxo-substituted heterocyclic-CO-groups, adamantyl group, lower alkylsulfonyl groups and arylsulfonyl groups.

2. The 1,2-ethanediol derivative or salt thereof according to claim 1, wherein $R^1$ represents a benzofuranyl group; $R^2$ represents a hydrogen atom; $R^3$ represents a hydrogen atom; $nR^4$'s and $nR^5$'s represent hydrogen atoms; $R^6$ represents a pyridyl group, a piperidinyl group which may optionally be substituted by a lower alkyl group, a 1,2,5,6-tetrahydropyridyl group which may optionally be substituted by a lower alkyl group, an imidazolyl group, a phenyl-$C_{1-4}$ alkyl group substituted piperazinyl group or an amino group which may optionally be substituted by a lower alkyl or cycloalkyl group; and n represents an integer of 1 to 4.

3. 1-(Benzo[b]furan-5-yl)-2-[2-(N,N-dimethylamino) ethoxy]ethanol or a salt thereof.

4. A method of treating cerebrovascular dementia, senile dementia, Alzheimer's dementia, sequelae of ischemic encephalopathy or cerebral apoplexy in a patient, comprising:

administering to a patient in need a therapeutically effective amount of a 1,2-ethanediol derivative represented by the following formula or a salt thereof:

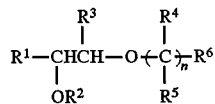

wherein $R^1$ represents a substituted or unsubstituted heterocyclic group selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl, indazolyl, furyl, thienyl, pyranyl, isobenzofuranyl, oxazolyl, benzofuranyl, indolyl, benzimidazolyl, benzoxazolyl, benzothiazolyl, quinoxalyl, dihydroquinoxalyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl and isoquinolyl; $R^2$ represents a hydrogen atom, a lower alkyl group or a hydroxyl-protecting group; $R^3$ represents a hydrogen atom or a lower alkyl group; $n^4$'s and $nR^5$'s are the same as or different from one another and represent hydrogen atoms or lower alkyl groups; $R^6$ represents an ammonio group or a substituted or unsubstituted amino or nitrogen-containing heterocyclic group, the nitrogen-containing heterocyclic group being selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl groups; and n represents 0 or an integer of 1 to 6, wherein the substituent on $R^1$ is selected from the group consisting of halogen atoms, substituted or unsubstituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino and heterocyclic groups, protected amino groups, protected or unprotected hydroxyl groups, nitro group, oxo group and lower alkylenedioxy groups; the substituted lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino or heterocyclic group as the substituent of $R^1$ and the substituted nitrogen-containing heterocyclic group as $R^6$ have each at least one substituent selected from the group consisting of halogen atoms, protected or unprotected hydroxyl groups, protected or unprotected amino groups, protected or unprotected carboxyl groups, unsubstituted lower alkyl groups, lower alkyl groups substituted by a protected or unprotected hydroxyl group, unsubstituted or halogen-substituted aryl groups, unsubstituted or halogen-substituted aroyl groups, unsubstituted lower alkoxy groups, lower alkoxy groups substituted by a lower alkoxy group, lower acyl groups, ar-lower alkyl groups, ar-lower alkenyl groups, heterocyclic groups, heterocyclic-CO-groups, oxo group, lower alkylsulfonyl groups and arylsulfonyl groups; and the substituted amino group as the substituent of $R^1$ and the substituted amino group as $R^6$ have each at least one substituent selected from the group consisting of protected or unprotected hydroxyl groups, unsubstituted lower alkyl groups, lower alkyl groups substituted by a protected or unprotected carboxyl or hydroxyl groups, cycloalkyl groups, aryl groups, lower acyl groups, ar-lower alkyl groups, heterocyclic groups, unsubstituted or oxo-substituted heterocyclic-CO-groups, adamantyl group, lower alkylsulfonyl groups and arylsulfonyl groups.

5. The method according to claim 4, wherein $R^1$ presents the substituted or unsubstituted furyl, thienyl, pyridyl, quinolyl, 2,3-dihydrobenzofuranyl, indolyl, benzofuranyl, 1,2,3,4-tetrahydroquinolinyl or imidazolyl group; $R^6$ represents an ammonio group or a substituted or unsubstituted amino or nitrogen-containing heterocyclic group, the nitrogen-containing heterocyclic group being selected from the group consisting of pyrrolinyl, piperidyl, piperazinyl, imidazolyl, pryidyl, morpholinyl, thiomorpholinyl, tetrahydropyridyl, quinuclidinyl and tetrazolyl, the substituent on $R^1$ is selected from the group consisting of halogen atoms; lower alkyl groups; lower alkenyl groups; phenyl groups which may optionally be substituted by a halogen atom or a lower alkyl or lower alkoxy group; phenyl-$C_{1-4}$ alkyl groups; lower alkoxy groups which may optionally be substituted by a pyridyl, furyl or thienyl group; phenyl-$C_{1-4}$ alkoxy groups which may optionally be substituted by a halogen atom or a lower alkyl, hydroxyl or lower alkoxy group; a phenoxy group; phenylaminocarbonyloxy groups which may optionally be substituted by a halogen atom; lower alkylaminocarbonyloxy groups; lower alkylthio groups; a phenylsulfonylamino group; amino groups which may optionally be substituted by a lower alkyl group; a hydroxyl group; a nitro group; an oxo group; phenyl-$C_{1-4}$ alkylthio groups; phenyl-$C_{1-4}$ alkylsulfonyl groups; a thienyl group; a pyridyl group; and lower alkylenedioxy groups; the substituent on $R^6$, when $R^6$ is a substituted amino group, is selected from the group consisting of lower alkyl groups which may optionally be substituted by a hydroxyl group; lower acyl groups; cycloalkyl groups; phenyl-$C_{1-4}$alkyl groups; a pyrimidinyl group; a pyridinecarbonyl group and an adamantyl group; and the substituent on $R^6$, when $R^6$ is a substituted nitrogen-containing heterocyclic group, is selected from the group consisting of halogen atoms; a hydroxyl group; lower alkyl groups which may optionally be substituted by a hydroxyl group; an amino group; lower acyl groups which may optionally be substituted by a pyrrolidinyl group; phenyl-$C_{1-4}$alkyl groups; phenyl-$C_{2-4}$alkenyl groups; aroyl groups which are substituted by a halogen atom; a pyridyl group and an oxo group.

6. The method to claim 5, wherein $R^1$ represents a benzofuranyl group, $R^2$ represents a hydrogen atom; $R^3$ represents a hydrogen atom; $nR^4$'s and $nR^5$'s represent hydrogen atoms; $R^6$ represents a pyridyl group; a piperadinyl group which may optionally be substituted by a lower alkyl group; 1,2,5,6-tetrahydropyridyl group which may optionally be substituted by a lower alkyl group; an imidazolyl group; a phenyl-$C_{1-4}$ alkyl group-substituted piperazinyl group or an amino group which may optionally be substituted by a lower alkyl group or a cycloalkyl group; and n represents an integer of 1 to 4.

7. The method according to claim 4, wherein the derivative or salt is 1-(benzo[b]furan-5-yl)-2-(2-(N,N-dimethylamino)ethoxy]ethanol or a salt thereof.

8. A cerebral function-improving agent comprising a 1,2-ethanediol derivative represented by the following formula or a salt thereof:

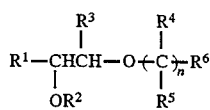

wherein $R^1$ represents a substituted or unsubstituted heterocyclic group selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl, indazolyl, furyl, thienyl, pyranyl, isobenzofuranyl, oxazolyl, benzofuranyl, indolyl, benzimidazolyl, benzoxazolyl, benzothiazolyl, quinoxalyl, dihydroquinoxalyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl and isoquinolyl; $R^2$ represents a hydrogen atom, a lower alkyl group or a hydroxyl-protecting group; $R^3$ represents a hydrogen atom or a lower alkyl group; $nR^4$'s and $nR^5$'s are the same as or different from one another and represent hydrogen atoms or lower alkyl groups; $R^6$ represents an ammonio group or a substituted or unsubstituted amino or nitrogen-containing heterocyclic group, the nitrogen-containing heterocyclic group being selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl groups; and n represents 0 or an integer of 1 to 6, wherein the substituent on $R^1$ is selected from the group consisting of halogen atoms, substituted or unsubstituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino and heterocyclic groups, protected amino groups, protected or unprotected hydroxyl groups, nitro group, oxo group and lower alkylenedioxy groups; the substituted lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino or heterocyclic group as the substituent of $R^1$ and the substituted nitrogen-containing heterocyclic group as $R^6$ have each at least one substituent selected from the group consisting of halogen atoms, protected or unprotected hydroxyl groups, protected or unprotected amino groups, protected or unprotected carboxyl groups, unsubstituted lower alkyl groups, lower alkyl groups substituted by a protected or unprotected hydroxyl group, unsubstituted or halogen-substituted aryl groups, unsubstituted or halogen-substituted aroyl groups, unsubstituted lower alkoxy groups, lower alkoxy groups substituted by a lower alkoxy group, lower acyl groups, ar-lower alkyl groups, ar-lower alkenyl groups, heterocyclic groups, heterocyclic-CO-groups, oxo groups, lower alkylsulfonyl groups and arylsulfonyl groups; and the substituted amino group as the substituent of $R^1$ and the substituted amino group as $R^6$ have each at least one substituent selected from the group consisting of protected or unprotected hydroxyl groups, unsubstituted lower alkyl groups, lower alkyl groups substituted by a protected or unprotected carboxyl or hydroxyl group, cycloalkyl groups, aryl groups, lower acyl groups, ar-lower alkyl groups, heterocyclic groups, unsubstituted or oxo-substituted heterocyclic-CO-groups, adamantyl group, lower alkylsulfonyl groups and arylsulfonyl groups; in combination with a pharmaceutically acceptable inert excipient, diluent or carrier.

9. A method of treating cerebrovascular dementia, senile dementia, Alzheimer's dementia, sequelae of ischemic encephalopathy or cerebral apoplexy in a patient, comprising:

administering to a patient in need a therapeutically effective amount of a 1,2-ethanediol derivative represented by the following formula or a salt thereof:

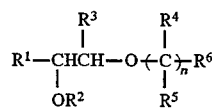

wherein $R^1$ represents a substituted or unsubstituted heterocyclic group selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl, indazolyl, furyl, thienyl, pyranyl, isobenzofuranyl, oxazolyl, benzofuranyl, indolyl, benzimidazolyl, benzoxazolyl, benzothiazolyl, quinoxalyl, dihydroquinoxalyl, 2,3-dihydrobenzopyrrolyl, 2,3-dihydro-4H-1-thianaphthyl, 2,3-dihydrobenzofuranyl, benzo[b]dioxanyl, imidazo[2,3-a]pyridyl, benzo[b] piperazinyl, chromenyl, isothiazolyl, isoxazolyl, oxadiazolyl, pyridazinyl, isoindolyl and isoquinolyl; $R^2$ represents a hydrogen atom, a lower alkyl group or a hydroxyl-protecting group; $R^3$ represents a hydrogen atom or a lower alkyl group; $nR^4$'s and $nR^5$'s are the same as or different from one another and represent hydrogen atoms or lower alkyl groups; $R^6$ represents an ammonio group or a substituted or unsubstituted amino or nitrogen-containing heterocyclic group, the nitrogen-containing heterocyclic group being selected from the group consisting of pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl groups; and n represents 0 or an integer of 1 to 6, wherein the substituent on $R^1$ is selected from the group consisting of halogen atoms, substituted or unsubstituted amino, lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonyl amino and heterocyclic groups, protected amino groups, protected or unprotected hydroxyl groups, nitro group, oxo group and lower alkylenedioxy groups; the substituted lower alkyl, aryl, ar-lower alkyl, lower alkoxy, ar-lower alkoxy, aryloxy, carbamoyloxy, lower alkylthio, lower alkenyl, lower alkenyloxy, ar-lower alkylthio, ar-lower alkylsulfonyl, arylsulfonyl, lower alkylsulfonylamino, arylsulfonylamino or heterocyclic group as the substituent of $R^1$ and the substituted nitrogen-containing heterocyclic group as $R^6$ have each at least one substituent selected from the group consisting of halogen atoms, protected or unprotected hydroxyl groups, protected or unprotected amino groups, protected or unprotected carboxyl groups, unsubstituted lower alkyl groups, lower alkyl groups substituted by a protected or unprotected hydroxyl group, unsubstituted or halogen-substituted aryl groups, unsubstituted or halogen-substituted aroyl groups, unsubstituted lower alkoxy groups, lower alkoxy groups substituted by a lower alkoxy group, lower acyl groups, ar-lower alkyl groups, ar-lower alkenyl groups, heterocyclic groups, heterocyclic-CO-groups, oxo group, lower alkylsulfonyl groups and arylsulfonyl groups; and the substituted amino group as the substituent of $R^1$ and the substituted amino group as $R^6$ have each at least one substituent selected from the group consisting of protected or unprotected hydroxyl groups, unsubstituted lower alkyl groups, lower alkyl groups substituted by a protected or unprotected carboxyl or hydroxyl group, cycloalkyl groups, aryl groups, lower acyl groups, ar-lower alkyl groups, heterocyclic groups, unsubstituted or oxo-substituted heterocyclic-CO-groups, adamantyl group, lower alkylsulfonyl groups and arylsulfonyl groups.

10. A 1,2-ethanediol derivative of the formula:

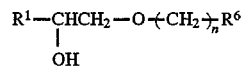

wherein $R^1$ represents a benzofuranyl group; and $R^6$ represents a pyridyl group, a piperidinyl group which may optionally be substituted by a lower alkyl group, a 1,2,5,6-tetrahydropyridyl group which may optionally be substituted by a lower alkyl group, an imidazolyl group, a phenyl-$C_{1-4}$alkyl group-substituted piperazinyl group or an amino group which may optionally be substituted by a lower alkyl or cycloalkyl group; and n represents an integer of 1 to 4.

* * * * *